US009796670B2

(12) United States Patent
Patel et al.

(10) Patent No.: US 9,796,670 B2
(45) Date of Patent: Oct. 24, 2017

(54) N-(4-HYDROXY-4-METHYL-CYCLOHEXYL)-4-PHENYL-BENZENE-SULFONAMIDES AND N-(4-HYDROXY-4-METHYL-CYCLOHEXYL)-4-(2-PYRIDYL) BENZENESULFONAMIDES AND THEIR THERAPEUTIC USE

(71) Applicant: PIMCO 2664 LIMITED, London (GB)

(72) Inventors: Lisa Patel, London (GB); Stephen Allan Smith, Essex (GB); Iain Robert Greig, Aberdeen (GB); Samuel Cameron Williams, London (GB)

(73) Assignee: PIMCO 2664 LIMITED, London (GB)

( * ) Notice: Subject to any disclaimer, the term of this patent is extended or adjusted under 35 U.S.C. 154(b) by 0 days.

(21) Appl. No.: 15/484,256

(22) Filed: Apr. 11, 2017

(65) Prior Publication Data
US 2017/0217881 A1  Aug. 3, 2017

Related U.S. Application Data

(63) Continuation of application No. 14/899,422, filed as application No. PCT/GB2014/051921 on Jun. 24, 2014, now Pat. No. 9,624,167.

(30) Foreign Application Priority Data

Jun. 26, 2013  (GB) .................................. 1311361.8

(51) Int. Cl.
C07C 311/20 (2006.01)
C07D 213/61 (2006.01)

(52) U.S. Cl.
CPC .......... *C07C 311/20* (2013.01); *C07D 213/61* (2013.01); *C07C 2101/14* (2013.01)

(58) Field of Classification Search
None
See application file for complete search history.

(56) References Cited

U.S. PATENT DOCUMENTS

| 4,119,784 | A | 10/1978 | Conrow et al. |
| 4,948,809 | A | 8/1990 | Witte et al. |
| 5,760,028 | A | 6/1998 | Jadhav et al. |
| 6,159,995 | A | 12/2000 | Thorwart et al. |
| 6,451,824 | B1 | 9/2002 | Thorwart et al. |
| 6,849,635 | B2 | 2/2005 | Dhanak et al. |
| 7,560,597 | B2 | 7/2009 | Greig et al. |
| 7,572,825 | B2 | 8/2009 | Ralston et al. |
| 7,598,289 | B2 | 10/2009 | Ralston et al. |
| 7,745,424 | B2 | 6/2010 | Ralston et al. |
| 7,964,643 | B2 | 6/2011 | Ralston et al. |
| 8,207,167 | B2 | 6/2012 | Greig et al. |
| 8,435,968 | B2 | 5/2013 | Greig et al. |
| 8,524,778 | B2 | 9/2013 | Greig et al. |
| 8,822,507 | B2 | 9/2014 | Greig et al. |
| 9,050,329 | B1 | 6/2015 | Greig et al. |
| 9,302,984 | B2 | 4/2016 | Greig et al. |
| 9,616,037 | B2 | 4/2017 | Greig et al. |
| 9,624,167 | B2 | 4/2017 | Patel et al. |
| 2003/0144292 | A1 | 7/2003 | Natchus et al. |

(Continued)

FOREIGN PATENT DOCUMENTS

| DE | 10 46 220 | 12/1958 |
| DE | 3000519 A1 | 8/1980 |

(Continued)

OTHER PUBLICATIONS

Akahoshi et al., 2008, "Promoter polymorphisms in the IRF3 gene confer protection against systemic lupus erythematosus", Lupus, vol. 17, pp. 568-574.
Annex to UK Search Report for GB 0705400.0—Jul. 9, 2007.
Argus et al. (1958) "Distribution studies with sulphur 35-labeled disulfonamides in tumor-bearing and tumor-free mice" Brit. J. Cancer 12:636-644.
Armour K.J., et al., 2001, "Inhibition of bone resorption in vitro and prevention of ovariectomy-induced bone loss in vivo by flurbiprofen nitroxybutylester (HCT1026), " Arthritis and Rheumatism, vol. 44, No. 9, pp. 2185-2192.
Astry et al., 2011, "A cytokine-centric view of the pathogenesis and treatment of autoimmune arthritis", J Interferon Cytokine Res., vol. 31, pp. 927-940.

(Continued)

*Primary Examiner* — Heidi Reese
(74) *Attorney, Agent, or Firm* — Swanson & Bratschun, L.L.C.

(57) ABSTRACT

The present invention pertains generally to the field of therapeutic compounds. More specifically the present invention pertains to certain substituted N-(4-hydroxy-4-methyl-cyclohexyl)-4-phenyl-benzenesulfonamide and N-(4-hydroxy-4-methyl-cyclohexyl)-4-(2-pyridyl) benzenesulfonamide compounds (collectively referred to herein as HMC compounds) that are useful, for example, in the treatment of disorders (e.g., diseases) including, inflammation and/or joint destruction and/or bone loss; disorders mediated by excessive and/or inappropriate and/or prolonged activation of the immune system; inflammatory and autoimmune disorders, for example, rheumatoid arthritis; psoriasis; psoriatic arthritis; chronic obstructive pulmonary disease (COPD); asthma; atherosclerosis; inflammatory bowel disease; ankylosing spondylitis; multiple sclerosis; systemic lupus erythematosus; Sjogren's syndrome; a disorder associated with bone loss, such as bone loss associated with excessive osteoclast activity in rheumatoid arthritis, osteoporosis, cancer-associated bone disease, or Paget's disease; cancer, such as a haematological malignancy, such as multiple myeloma, leukemia, or lymphoma, or a solid tumor cancer, such as bladder cancer, breast cancer (female and/or male), colon cancer, renal cell carcinoma, kidney cancer, lung cancer, pancreatic cancer, gastric cancer, prostate cancer, brain cancer, skin cancer, thyroid cancer, basal cell ameloblastoma, or melanoma; a disorder associated with fibrosis, such as systemic sclerosis or scleroderma; or a rare vasculitide, such as Behçet's disease. The present invention also pertains to pharmaceutical compositions comprising such compounds, and the use of such compounds and compositions, for example, in therapy.

33 Claims, 3 Drawing Sheets

(56) References Cited

U.S. PATENT DOCUMENTS

| | | |
|---|---|---|
| 2005/0119305 A1 | 6/2005 | Naka et al. |
| 2005/0227987 A1 | 10/2005 | Vicker et al. |
| 2006/0030543 A1 | 2/2006 | Malecha et al. |
| 2007/0191370 A1 | 8/2007 | Devasagayaraj et al. |
| 2008/0119555 A1 | 5/2008 | Ralston et al. |
| 2008/0255240 A1 | 10/2008 | Christiansen et al. |
| 2010/0286266 A1 | 11/2010 | Greig et al. |
| 2011/0172189 A1 | 7/2011 | Greig et al. |
| 2011/0190302 A1 | 8/2011 | Greig et al. |
| 2013/0245018 A1 | 9/2013 | Greig et al. |
| 2015/0141472 A1 | 5/2015 | Greig et al. |
| 2015/0266815 A1 | 9/2015 | Greig et al. |
| 2016/0145206 A1 | 5/2016 | Patel et al. |
| 2016/0206578 A1 | 7/2016 | Greig et al. |

FOREIGN PATENT DOCUMENTS

| | | |
|---|---|---|
| EP | 0877018 A1 | 5/1998 |
| EP | 0 960 882 | 12/1999 |
| EP | 0 877 019 | 12/2001 |
| EP | 0 988 018 | 3/2003 |
| EP | 1 431 267 | 6/2004 |
| EP | 1 491 190 | 12/2004 |
| EP | 1659113 A1 | 5/2006 |
| GB | 597810 | 2/1948 |
| JP | 11246527 | 9/1999 |
| JP | 2001-504809 | 4/2001 |
| WO | WO 96/37492 | 11/1996 |
| WO | WO 97/16433 | 5/1997 |
| WO | WO 97/33887 | 9/1997 |
| WO | WO 98/03166 | 1/1998 |
| WO | WO 98/16503 | 4/1998 |
| WO | WO 98/23608 | 6/1998 |
| WO | WO 98/43962 | 10/1998 |
| WO | WO 98/50342 | 11/1998 |
| WO | WO 99/37621 | 7/1999 |
| WO | WO 99/42443 | 8/1999 |
| WO | WO 99/59992 A1 | 11/1999 |
| WO | WO 01/16137 | 3/2001 |
| WO | WO 01/90077 | 11/2001 |
| WO | WO 02/060867 | 8/2002 |
| WO | WO 02/074298 | 9/2002 |
| WO | WO 03/037321 | 5/2003 |
| WO | WO 2004/022561 | 3/2004 |
| WO | WO 2004/039784 | 5/2004 |
| WO | WO 2004/073619 | 9/2004 |
| WO | WO 2004/098582 | 11/2004 |
| WO | WO 2004/106290 A1 | 12/2004 |
| WO | WO 2005/025554 | 3/2005 |
| WO | WO 2005/060963 A1 | 7/2005 |
| WO | WO 2005/080367 | 9/2005 |
| WO | WO 2005/085189 A2 | 9/2005 |
| WO | WO 2005/105712 A1 | 11/2005 |
| WO | WO 2005/118528 | 12/2005 |
| WO | WO 2006/046916 | 5/2006 |
| WO | WO 2006/134467 A1 | 12/2006 |
| WO | WO 2007/008541 A2 | 1/2007 |
| WO | WO 2007/026962 A1 | 3/2007 |
| WO | WO 2007/056341 | 5/2007 |
| WO | WO 2008/114022 | 9/2008 |
| WO | WO 2010/025235 | 3/2010 |
| WO | WO 2010/027500 | 3/2010 |
| WO | WO 2010/032009 A1 | 3/2010 |
| WO | WO 2010/032010 A1 | 3/2010 |
| WO | WO 2014/207445 | 12/2014 |

OTHER PUBLICATIONS

Augstein, J., et al., 1965, "Some cardiovascular effects of a series of aryloxyalkylamines 1", J. Med. Chem., vol. 8, pp. 356-367.
Baud et al., 1999, "Signaling by proinflammatory cytokines: oligomerization of TRAF2 and TRAF6 is sufficient for JNK and IKK activation and target gene induction via an amino-terminal effector domain", Genes Dev., vol. 13, pp. 1297-1308.
Baud et al., 2009, "Is NFκB a good target for cancer therapy? Hopes and pitfalls", Nat. Rev. Drug Disc., vol. 8, pp. 33-40.
Billiau, 2010, "Etanercept improves linear growth and bone mass acquisition in MTX-resistant polyarticular-course juvenile idiopathic arthritis", Rheumatology (Oxford), vol. 49, pp. 1550-1558.
Brennan et al., 1989, "Inhibitory effect of TNF alpha antibodies on synovial cell interleukin-1 production in rheumatoid arthritis", Lancet, vol. 2, pp. 244-247.
Brennan et al., 1992, "Enhanced expression of tumor necrosis factor receptor mRNA and protein in mononuclear cells isolated from rheumatoid arthritis synovial joints", Eur. J. Immunol., vol. 22, pp. 1907-1912.
Brennan et al., 1996, "Cytokines in autoimmunity", Curr. Opin. Immunol., vol. 8, pp. 872-877.
Chemcats record for Enamine Screening Library, Enamine, Kiev, Ukraine, publication date Jan. 17, 2008, CAS Registry No. 950020-41-4 (2 pages).
Chemcats record for LaboTest Stock Catalog, LaboTest, Niederschoena, Germany, publication date Jul. 24, 2007, CAS Registry No. 331653-75-9 (2 pages).
Chemcats record for Ryan Scientific Screening Library, Ryan Scientific, Inc., Mt. Pleasant, SC, USA, publication date Jan. 25, 2008, CAS Registry No. 302603-86-7 (2 pages).
Chemcats record for Scientific Exchange Product List, Scientific Exchange, Inc., Centre Ossipee, NH, USA, publication date Jan. 30, 2008, CAS Registry No. 312756-83-5 (2 pages).
Chemcats records for Nanosyn Compound Library, Nanosyn Combinatorial Synthesis Inc., Menlo Park, CA, USA, publication date Apr. 17, 2007, CAS Registry Nos. 313495-94-2, 313521-07-2 (3 pages).
Chemcats records for Spectrum Info Catalog, Spectrum Info Ltd., Kiev, Ukraine, publication date Sep. 5, 2007: CAS Registry No. 885269-21-6, 885269-2-9, 885269-42-1, 885269-85-2, 885269-88-5, 885269-91-0 (7 pages).
Chen et al., 2012, "High-affinity and selective dopamine D3 receptor full agonists", Bioorg. & Med. Chem. Lett., vol. 22, pp. 5612-5617.
Childs, L.M., et al., 2001, "Efficacy of etanercept for wear debris-induced osteolysis", Journal of Bone and Mineral Research, vol. 16, No. 2, pp. 338-347.
Corey EJ, Shibata S, Bakshi RK, 1988, "An effcicient and catalytically enantioselective route to (S)-(−)-Phenyloxirane," J. Org. Chem., vol. 53, pp. 2861-2863.
Coxon, F.P., et al., 2000, "Protein geranylgeranylation is required for osteoclast formation, function, and survival: inhibition by bisphosphonates and GGTI-298," J.Bone Miner.Res., vol. 15, pp. 1467-1476.
Degenhardt, C.R., et al., 1986, "Synthesis of Ethenylidenebis(phosphonic acid) and its Tetraalkyl Esters," J. Org. Chem., vol. 51, pp. 3488-3490.
Dvorak et al., 1996, "Comparative ultrastructural morphology of human basophils stimulated to release histamine by anti-IgE, recombinant IgE-dependent histamine-releasing factor, or monocyte chemotactic protein-1", Journal of Allergy and Clinical Immunology, vol. 98, pp. 355-370.
Eberhard, A., et al., 1965, "Hydrolysis of Phostonates," J. Amer. Chem. Soc., vol. 87, pp. 253-260.
Elliott et al., 1994, "Randomised double-blind comparison of chimeric monoclonal antibody to tumour necrosis factor alpha (cA2) versus placebo in rheumatoid arthritis", Lancet, vol. 344, pp. 1105-1110.
Feldmann et al., 1994, "TNF alpha as a therapeutic target in rheumatoid arthritis," Circ. Shock, vol. 43, pp. 179-184.
Feldmann et al., 1996, "Rheumatoid arthritis", Cell, vol. 85, pp. 307-310.
Feldmann et al., 2001, "The role of TNF alpha and IL-1 in rheumatoid arthritis," Curr. Dir. Autoimmun., vol. 3, pp. 188-199.
Firestein et al., 1999, "Signal transduction and transcription factors in rheumatic disease", Arthritis Rheum., vol. 42, pp. 609-621.
Firestein, 1996, "Invasive fibroblast-like synoviocytes in rheumatoid arthritis. Passive responders or transformed aggressors?", Arthritis Rheum., vol. 39, pp. 1781-1790.

(56) References Cited

OTHER PUBLICATIONS

Firestein, 2005 "Immunologic mechanisms in the pathogenesis of rheumatoid arthritis", J. Clin. Rheumatol., vol. 11. pp. S39-S44.
Fu et al., 2011, "Association of a functional IRF7 variant with systemic lupus erythematosus", Arthritis Rheum., vol. 63, pp. 749-754.
Gabay, 2006, "Interleukin-6 and chronic inflammation", Arthritis Research & Therapy, vol. 8 (Suppl 2), S3.pp. 1-6.
Galli et al., 1989, "IgE, Mast Cells and the Allergic Response", Ciba Foundation Symposium, vol. 147, pp. 53-73.
Gottlieb, 2005, "Psoriasis: Emerging Therapeutic Strategies", Nat. Rev. Drug Disc., vol. 4, pp. 19-34.
Greig et al., 2006, "Development and characterization of biphenylsulfonamides as novel inhibitors of bone resorption", J. Med. Chem., vol. 49: pp. 7487-7492.
Greig et al., 2013, "Development of triarylsulfonamides as novel anti-inflammatory agents", Bioorg. & Med. Chem. Lett., vol. 23, pp. 816-820.
Ha-Duong, N-T, et al, 2001, "Synthesis of sulfaphenazole derivatives and their use as inhibitors and tools for comparing the active sites of human liver cytochromes P450 of the 2C subfamily", J. Med. Chem., vol. 44, pp. 3622-3631.
Herczegh, P., et al, 2002, "Osteoadsorptive Bisphosphonate Derivatives of Fluoroquinolone Antibacterials," J. Med. Chem., vol. 45, pp. 2338-2341.
Hu et al., 2011, "A meta-analysis of the association of IRF5 polymorphism with systemic lupus erythematosus International", Journal of Immunogenetics, vol. 38, pp. 411-417.
Hughes, D.E., et al., 1997, "Apoptosis in bone physiology and disease," J. Clin. Pathol.: Molecular Pathology, vol. 50, pp. 132-137.
International Preliminary Report on Patentability (IPRP) for PCT/GB2005/002043 issued Dec. 4, 2006.
International Preliminary Report on Patentability (IPRP) for PCT/GB2008/000989 issued Sep. 22, 2009.
International Preliminary Report on Patentability (IPRP) for PCT/GB2009/002221 issued Mar. 22, 2011.
International Preliminary Report on Patentability (IPRP) for PCT/GB2009/002223 issued Mar. 22, 2011.
International Preliminary Report on Patentability (IPRP) for PCT/GB2014/051921 issued Dec. 29, 2015.
International Search Report (ISR) and Written Opinion of International Searching Authority (WOISA) for PCT/EP2015/080022 mailed Feb. 17, 2016.
International Search Report (ISR) and Written Opinion of International Searching Authority (WOISA) for PCT/GB2005/002043 mailed Nov. 16, 2005.
International Search Report (ISR) and Written Opinion of International Searching Authority (WOISA) for PCT/GB2008/000989 mailed Jul. 22, 2008.
International Search Report (ISR) and Written Opinion of International Searching Authority (WOISA) for PCT/GB2009/002221 mailed Jan. 18, 2010.
International Search Report (ISR) and Written Opinion of International Searching Authority (WOISA) for PCT/GB2009/002223 mailed Feb. 9, 2010.
International Search Report (ISR) and Written Opinion of International Searching Authority (WOISA) for PCT/GB2014/051921 mailed Aug. 20, 2014.
Jimi et al., 2004, "Selective inhibition of NF-kappa B blocks osteoclastogenesis and prevents inflammatory bone destruction in vivo", Nat. Med., vol. 10, pp. 617-624.
Jones et al., 2011, "Osteoimmunology at the nexus of arthritis, osteoporosis, cancer, and infection", J. Clin. Invest., vol. 121, pp. 2534-2542.
Joosten et al., 1996, "Anticytokine treatment of established type II collagen-induced arthritis in DBA/1 mice. A comparative study using anti-TNF alpha, anti-IL-1 alpha/beta, and IL-1 Ra," Arthritis Rheum., vol. 39, pp. 797-809.
Karsenty et al., 2002, "Reaching a genetic and molecular understanding of skeletal development", Dev. Cell., vol. 2, pp. 389-406.
Klareskog et al., 2006, "A long-term, open-label trial of the safety and efficacy of etanercept (Enbrel) in patients with rheumatoid arthritis not treated with other disease-modifying antirheumatic drugs", Ann. Rheum. Dis., vol. 65, pp. 1578-1584.
Klareskog et al., 2006, "Mechanisms of disease: Genetic susceptibility and environmental triggers in the development of rheumatoid arthritis," Nat. Clin. Pract. Rheumatol., vol. 2, pp. 425-433.
Kong, Y.Y., et al., 1999, "OPGL is a key regulator of osteoclastogenesis, lymphocyte development and lymph-node organogenesis," Nature, vol. 397, pp. 315-323.
Korzenik et al., 2006, "Evolving knowledge and therpy of inflammatory bowel disease," Nat. Rev. Drug Disc., vol. 5, pp. 197-209.
Krausgruber et al., 2011, "IRF5 promotes inflammatory macrophage polarization and TH1-TH17 responses", Nat. Immunol., vol. 12, pp. 231-238.
Li et al., 2008, "A tumor necrosis factor-[alpha]-mediated pathway promoting autosomal dominant polycystic kidney disease", Nature Medicine, vol. 14(8), pp. 863-868.
Liu, 2005, "Molecular mechanism of TNF signaling and beyond," Cell Res., vol. 15(1), pp. 24-27.
Long, et al., 2012, "Osteoimmunology: the expanding role of immunoreceptors in osteoclasts and bone remodeling", Bone Key Rep., vol. 1, p. 59.
Luckman et al., 1998, "Heterocycle-containing bisphosphonates cause apoptosis and inhibit bone resorption by preventing protein prenylation: evidence from structure—activity relationships in J774 macrophages," J. Bone Miner. Res., vol. 13, pp. 1668-1678.
MacPherson, H; et al., 1999, "Expression and functional role of nitric oxide synthase isoforms in human osteoblast-like cells," Bone, vol. 24, pp. 179-185.
Malemud, 2011 "Myeloid-related protein activity in Rheumatoid Arthritis", International Journal of Inflammation., vol. 2011, pp. 1-5.
Mantovani, 2009, "Inflaming metastasis", Nature, vol. 457, pp. 36-37.
Mazzucchelli et al., 1996, "Differential in situ expression of the genes encoding the chemokines MCP-1 and RANTES in human inflammatory bowel disease", J. Pathol., vol. 178, No. 2, pp. 201-206.
McInnes et al., 2005, "Targeting cytokines beyond tumor necrosis factor-alpha and interleukin-1 in rheumatoid arthritis", Curr. Pain Headache Rep., vol. 9, pp. 405-411.
McInnes et al., 2007, "Cytokines in the pathogenesis of rheumatoid arthritis", Nat. Rev. Immunol., vol. 7, pp. 429-442.
Minamino et al., 2012, "IRF-2 regulates B-cell proliferation and antibody production through distinct mechanisms", Int Immunol., vol. 24, pp. 573-581.
Mohan et al. (1993) "Structure-Activity Relationship Studies with Symmetric Naphthalenesulfonic Acid Derivatives. Synthesis and Influence of Spacer and Naphthalenesulfonic Acid Moiety on Anti-HIV-1 Activity" J. Med. Chem. 36:1996-2003.
Mount et al., 2005, "Rheumatoid arthritis market", Nat. Rev. Drug Disc., vol. 2, pp. 11-12.
Mundy, G.R., 1996, "Chapter 1: Bone Remodeling", in Bone Remodeling and its disorders (2nd edition), London, (Ed. Martin Dunitz), pp. 1-11.
Nociari et al., 1998, "A Novel one-step, highly sensitive fluorimetric assay to evaluate cell-mediated cytotoxicity", Journal of Immunological Methods, vol. 213, pp. 157-167.
Nyormoi, O., et al., 2003, "An MMP-2/MMP-9 inhibitor, 5a, enhances apoptosis induced by ligands of the TNF receptor superfamily in cancer cells", Cell Death and Differentiation, vol. 10, pp. 558-569.
O'Brien et al., 2000, "Structure-activity relationships and pharmacokinetic analysis for a series of potent, systemically available biphenylsulfonamide matrix metalloproteinase inhibitors". J. Med. Chem. vol. 43: pp. 156-166.
Ogata et al., 2012, "Safety and Efficacy of Tocilizumab for the Treatment of Rheumatoid Arthritis", Clin Med Insights Arthritis Musculoskelet Disord., vol. 5, pp. 27-42.

(56) References Cited

OTHER PUBLICATIONS

O'Shea et al., 2013, "Janus kinase inhibitors in autoimmune diseases", Annals of Rheumatic Disease, vol. 72, Supplement 2, pp. 111-115.
Papanicolaouet al., 1998, "The Pathophysiologic Roles of Interleukin-6 in Human Disease", Ann Intern Med., vol. 128, No. 2, pp. 127-137.
Parameswaran et al., 2010, "Tumor necrosis factor—a signaling in macrophages", Crit. Rev. Eukaryot. Gene Expr., vol. 20, pp. 87-103.
Peyman, A., et al., 2001, "$\alpha v \beta 3$ antagonists based on a central thiophene scaffold", Bio. & Med. Chem. Letters, Vo. 11, pp. 2011-2015.
Philchenkov et al., 2004, "Caspases and cancer: mechanisms of inactivation and new treatment modalities", Exp. Oncol., vol. 26(2), pp. 82-97.
Pisetsky, 2012, "Advances in the treatment of inflammatory arthritis", Best Pract. Res. Clin. Rheumatol., vol. 26. pp. 251-261.
Raisz, L.G., 1988, "Local and systemic factors in the pathogenesis of osteoporosis," N. Engl. J. Med., vol. 318, pp. 818-828.
Ralston, S.H., 1997, "Science, Medicine and the Future: Osteoporosis," Br. Med. J., vol. 315, pp. 469-472.
Ramachandran PV, Gong B, Brown HC, 1995, "Chiral synthesis via organoboranes", J. Org. Chem., vol. 60, pp. 41-46.
Rincon, 2012 "Interleukin-6: from an inflammatory marker to a target for inflammatory 5 diseases", Trends in Immunology, vol. 33, No. 11, pp. 571-577.
Rodan, G.A., et al., 1997, "The missing bone," Cell, vol. 89, pp. 677-680.
Roodman, 2006, "Regulation of osteoclast differentiation", Ann. N. Y. Acad. Sci., vol. 1068, pp. 100-109.
Sato et al., 2006, "Osteoclasts, rheumatoid arthritis, and osteoimmunology", Curr. Opin. Rheumatol., vol. 18, No. 4, pp. 419-426.
Scott et al., 2010, "Rheumatoid Arthritis", Lancet, vol. 376, pp. 1094-1108.
Sharif et al., 2012, "IRF5 polymorphism predicts prognosis in patients with systemic sclerosis", Annals of the Rheumatic Diseases, vol. 71, pp. 1197-1202.
Smolen et al., 2003, "Therapeutic Strategies for Rheumatoid Arthritis", Nat. Rev. Drug Disc., vol. 2, pp. 473-488.
Steger et al., 2011, "Denosumab for the treatment of bone metastases in breast cancer: evidence and opinion", Ther. Adv. Med. Oncol., vol. 3, pp. 233-243.
Sugiyama et al., 1995, "Chemokines in bronchoalveolar lavage fluid in summer-type hypersensitivity pneumonitis", Eur. Respir. J., vol. 8, pp. 1084-1090.
Sun, 2010, "Mechanical loading, cartilage degradation and arthritis", Annals of the New York Academy of Sciences, vol. 1211, pp. 37-50.
Takahashi, N.; et al., 1988, "Osteoblastic cells are involved in osteoclast formation," Endocrinology, vol. 123, pp. 2600-2602.
Takaoka et al., 2005, "Integral role of IRF-5 in the gene induction programme activated by 20 Toll-like receptors", Nature, vol. 434, pp. 243-249.
Takasuka, M., et al., 1991, "FTIR spectral study of intramolecular hydrogen bonding in thromboxane A2 receptor antagonist S-145 and related compounds. 3. Conformation and activity of S-145 analogues", J. Med. Chem., vol. 34, pp. 1885-1891.
Takayanagi, 2009, "Osteoimmunology and the effects of the immune system on bone", Nature Reviews Rheumatology, vol. 5, pp. 667-676.
Tanaka et al., 2003, Signal transduction pathways regulating osteoclast differentiation and function, J. Bone Miner. Metab., vol. 21, pp. 123-133.
UK Search Report for GB 0412553.0 dated Sep. 30, 2004.
UK Search Report for GB 0817207.4 dated Jan. 7, 2009.
UK Search Report for GB 0817208.2 dated Jan. 8, 2009.
UK Search Report for GB 1311361.8 dated Dec. 20, 2013.
UK Search Report for GB 1422469.5 (Corrected) daed Oct. 13, 2015.
UK Search Report for GB 1422469.5 dated Oct. 8, 2015.
UK Search Report for GB 705400.0 dated Jul. 6, 2007.
Van den Berg et al., 1999, "Pathogenesis of joint damage in rheumatoid arthritis: evidence of a dominant role for interleukin-1", Baillieres Best Pract. Res. Clin. Rheumatol., vol. 13(4), pp. 577-597.
Van den Berg, 2002, "Is there a rationale for combined TNF and IL-1 blocking in arthritis?", Clin. Exp. Rheumatol., vol. 20, pp. S21-S25.
Van't Hof, R.J., et a;., 1997, "Cytokine-induced nitric oxide inhibits bone resorption by inducing apoptosis of osteoclast progenitors and suppressing osteoclast activity," J. Bone & Miner. Res., vol. 12(11), pp. 1797-1804.
Volejnikova et al., 1997, "Monocyte recruitment and expression of monocyte chemoattractant protein-1 are developmentally regulated in remodeling bone in the mouse", Am. J. Pathol., vol. 150, No. 5, pp. 1711-1721.
Weaver, et al., 2003, "Cytochrome p450 inhibition using recombinant proteins and mass spectrometry/multiple reaction monitoring technology in a cassette incubation", Drug Metabolism and Disposition, vol. 31, No. 7, pp. 955-966.
Weissmann, 2006, "The pathogenesis of rheumatoid arthritis," Bull. Hosp. Jt. Dis., vol. 64, pp. 12-15.
Yasuda, H., et al, 1998, "Identity of osteoclastogenesis inhibitory factor (OCIF) and osteoprotegerin (OPG): a mechanism by which OPG/OCIF inhibits osteoclastogenesis in vitro", Endocrinology, vol. 139(3), pp. 1329-1337.
Zhang et al., 2012 "Regulation of T helper cell differentiation by interferon regulatory factor family members", Immunol. Res., vol. 54 pp. 169-176.
Zheng et al., 1998, "Gene expression of monocyte chemoattractant protein-1 in giant cell tumors of bone osteoclastoma: Possible involvement in CD68+ macrophage-like cell migration", Journal of Cellular Biochemistry, vol. 70, No. 1, pp. 121-129.
Ziff, 1990, "Rheumatoid arthritis—it's present and future", J. Rheumatol., vol. 17, pp. 127-133.

N-(4-HYDROXY-4-METHYL-CYCLOHEXYL)-4-PHENYL-BENZENESULFONAMIDES AND N-(4-HYDROXY-4-METHYL-CYCLOHEXYL)-4-(2-PYRIDYL)BENZENESULFONAMIDES AND THEIR THERAPEUTIC USE

RELATED APPLICATION

This application is a continuation of U.S. application Ser. No. 14/899,422, filed Dec. 17, 2015. U.S. application Ser. No. 14/899,422 is a 35 U.S.C. §371 national phase application of International Application Serial No. PCT/GB2014/051921, filed Jun. 24, 2014 (WO 2014/207445). International Application Serial No. PCT/GB2014/051921 claims priority to United Kingdom patent application number 1311361.8, filed Jun. 26, 2013. The contents of each of these applications are incorporated herein by reference in their entirety.

TECHNICAL FIELD

The present invention pertains generally to the field of therapeutic compounds. More specifically the present invention pertains to certain substituted N-(4-hydroxy-4-methyl-cyclohexyl)-4-phenyl-benzenesulfonamide and N-(4-hydroxy-4-methyl-cyclohexyl)-4-(2-pyridyl) benzenesulfonamide compounds (collectively referred to herein as HMC compounds) that are useful, for example, in the treatment of disorders (e.g., diseases) including, inflammation and/or joint destruction and/or bone loss; disorders mediated by excessive and/or inappropriate and/or prolonged activation of the immune system; inflammatory and autoimmune disorders, for example, rheumatoid arthritis; psoriasis; psoriatic arthritis; chronic obstructive pulmonary disease (COPD); asthma; atherosclerosis; inflammatory bowel disease; ankylosing spondylitis; multiple sclerosis; systemic lupus erythematosus; Sjogren's syndrome; a disorder associated with bone loss, such as bone loss associated with excessive osteoclast activity in rheumatoid arthritis, osteoporosis, cancer-associated bone disease, or Paget's disease; cancer, such as a haematological malignancy, such as multiple myeloma, leukemia, or lymphoma, or a solid tumour cancer, such as bladder cancer, breast cancer (female and/or male), colon cancer, renal cell carcinoma, kidney cancer, lung cancer, pancreatic cancer, gastric cancer, prostate cancer, brain cancer, skin cancer, thyroid cancer, basal cell ameloblastoma, or melanoma; a disorder associated with fibrosis, such as systemic sclerosis or scleroderma; or a rare vasculitide, such as Behçet's disease. The present invention also pertains to pharmaceutical compositions comprising such compounds, and the use of such compounds and compositions, for example, in therapy.

BACKGROUND

A number of publications are cited herein in order to more fully describe and disclose the invention and the state of the art to which the invention pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.
Chronic Inflammatory Disease Inflammation is the immune response of tissues due to bodily injury. Acute inflammation is a normal, protective response that protects and heals the body following physical injury or infection, characterised by heat, swelling, and redness at the site of the injury.

However, if inflammation persists for a prolonged period, it becomes chronic. Chronic inflammation is a hallmark of, and a contributing factor to, a range of disease conditions including rheumatoid arthritis, inflammatory bowel disease, systemic lupus erythematosus, multiple sclerosis and psoriasis.

The inflammatory process is complex and involves a biological cascade of molecular and cellular signals that alter physiological responses. At the site of the injury, cells release molecular signals such as cytokines and interleukins that cause a number of changes in the affected area including dilation of blood vessels, increased blood flow, increased vascular permeability, invasion by leukocytes (white blood cells), and exudation of fluids containing proteins like immunoglobulins (antibodies). Several different types of leukocytes, including granulocytes, monocytes, and lymphocytes, are involved in the inflammatory cascade. However, chronic inflammation is primarily mediated by monocytes and long-lived macrophages; monocytes mature into macrophages once they leave the bloodstream and enter tissues. Macrophages engulf and digest microorganisms, foreign invaders, and senescent cells and macrophages release several different chemical mediators, including Tumour Necrosis Factor-alpha (TNFα), interleukins (e.g., IL-1, IL-6, IL-12 and IL-23) and prostaglandins that perpetuate the inflammatory response. At later stages, other cells, including lymphocytes, invade the affected tissues.

There is thus a common pathology underlying a wide variety of chronic inflammatory conditions. In addition, features of chronic inflammation are also observed in other diseases including cancer and metabolic diseases such as obesity and diabetes.

One of the most common chronic inflammatory conditions is rheumatoid arthritis (RA), a condition which affects up to 2% of the population worldwide. Although it is a complex disease, there are a number of physiological, cellular, and biochemical factors associated with the progression of RA that are common to a range of other diseases, including those with a component of autoimmunity (e.g., multiple sclerosis), inflammation (e.g., atherosclerosis and cancer), bone loss (e.g., osteoporosis) and proliferation (e.g., haematological malignancies). This makes the understanding of RA important not only for the study of a much broader range of diseases, but also suggests that pharmaceutical agents that work via modification of these common processes may have utility beyond RA. The latter is borne out by clinical practice where RA drugs have been shown to have broad utility across a variety of other conditions.

Rheumatoid Arthritis and Related Autoimmune/Inflammatory Diseases

Rheumatoid arthritis (RA) is an autoimmune disorder characterized by chronic inflammation of the synovial lining of multiple joints coupled to progressive joint degradation. RA commonly affects the joints of the wrist and hands and may also affect the elbows, shoulders, hips, neck and knees leading to severe pain and disability (see, e.g., Scott et al., 2010). The World Health Organisation predicts that 23.7 million people suffer from RA, with incidence rising due to the association between the condition and increasing age.

The exact cause of RA, as for all the autoimmune disorders, remains unclear, although possible triggers include reduced self-tolerance, an abnormal response to environmental factors, infectious agents, and hormonal stimulus (see, e.g., Klareskog et al., 2006; Firestein et al., 2005).

At the cellular level, development of RA usually commences with T-cells infiltrating the synovial membrane lining the affected joint; this then leads to the activation of monocytes, macrophages and synovial fibroblasts by way of cell-cell contact and the subsequent release of various cytokines, including tumour necrosis factor-alpha (TNFα) and pro-inflammatory interleukins such as IL-1, IL-6, IL-12 and IL-23 (see, e.g., Astry et al., 2011). These pro-inflammatory cytokines are then instrumental in orchestrating several complex signal transduction cascades, including the NFκB, Interferon Regulatory Factor (IRF), Toll-like receptor (TLR), and Jak/STAT pathways (see, e.g., Malemud et al., 2010) which lead to the induction of genes coding for various products that propagate the inflammatory response and also promote tissue destruction. These products include tissue-degrading enzymes such as collagenases, matrix metalloproteinases (MMPs), cathepsins, and other pro-inflammatory factors such as selectins, integrins, leukotrienes, prostaglandins, chemokines, and other cytokines (see, e.g., McInnes et al., 2007; Smolen et al., 2003). In addition, these cells also increase the production of MMPs, leading to the degradation of the extra cellular matrix and loss of cartilage within the joint (see, e.g., Sun, 2010), a process that also involves a specialised class of cells known as osteoclasts and a factor known as Receptor Activator of Nuclear Factor Kappa-B Ligand (RANKL) (see, e.g., Takayanagi, 2009).

RANKL is an essential factor for the generation of osteoclasts, and upregulated RANKL-production leads to increased osteoclast differentiation and ultimately bone destruction (see, e.g., Long et al., 2012). The inflammatory response in RA leads to the accumulation of lymphocytes, dendritic cells, and macrophages, all operating locally to produce cytokines and other pro-inflammatory mediators such as TNFα and IL-6 which further potentiate the effects of RANKL on bone destruction. In addition, the inflammatory cascade leads to the hyperplasia of synoviocytes (see, e.g., Takayanagi, 2009), which in turn leads to the thickening and vascularisation of the synovium into a destructive and aggressive tissue known as a pannus. The pannus contains both osteoclasts, which destroy bone, and metalloproteinases, which are involved in the destruction of cartilage.

As such, the RANKL axis is critical to the progression and pathology of RA as well as to the osteoimmune system (the interplay between the immune and bone systems), which is central to the pathology of a number of different disease conditions, described below.

The Role of TNFα in RA

The TNF superfamily of receptors and ligands plays a key role in the causation of inflammation and associated local and systemic bone loss. TNFα is a powerful pro-inflammatory agent that regulates many facets of macrophage function. It is rapidly released after trauma, infection, or exposure to bacterial-derived LPS and has been shown to be one of the most abundant early mediators in inflamed tissue. Among its various functions is its central role in orchestrating the production of a pro-inflammatory cytokine cascade. In addition to pro-inflammatory cytokines, TNFα also increases lipid signal transduction mediators such as prostaglandins. Based on these roles, TNFα has been proposed as a central player in inflammatory cell activation and recruitment and is suggested to play a critical role in the development of many chronic inflammatory diseases including rheumatoid arthritis (see, e.g., Liu, 2005; Feldmann et al., 2001; Brennan et al., 1996; Brennan et al., 1992). The importance of TNFα in RA is highlighted by the finding that antibodies blocking TNFα can prevent inflammation in animal models of RA, and that anti-TNFα therapy is currently the most effective treatment for RA (see, e.g., Pisetsky, 2012, and further detail provided below).

TNFα itself instigates a signalling cascade which leads to the activation of the transcription factors NFκB and AP-1 (see, e.g., Parameswaran et al., 2010). Binding of TNFα and IL-1 to their respective receptors leads to the recruitment of downstream signal transducers called TRAFs. Further kinases are recruited by the TRAFs, and the resulting kinase complex activates the MAP-kinase pathway, ultimately leading to activation of AP-1, and the phosphorylation of IκB kinase. IκB is the inhibitor of NFκB, which acts by preventing translocation of NFκB to the nucleus. Phosphorylation of IκB by IκB kinase leads to degradation of IκB. Once IκB has been degraded, NFκB migrates to the nucleus, where it promotes transcription of anti-apoptotic genes, which promote survival of T- and B-cells, thereby prolonging the immune response. This prolongation of the inflammatory response is central to the chronic nature of RA. The importance of NFκB activation is demonstrated by the fact that inhibition of NFκB activity by inhibitory peptides can prevent arthritis in animal models of RA (see, e.g., Jimi et al., 2004).

Other Key Factors in Rheumatoid Arthritis

As described above, a number of factors in addition to TNFα and NFκB act to promote inflammation in RA and other chronic inflammatory diseases. Amongst these are IL-6 and the Interferon Regulatory Factors (IRFs).

Interleukin-6 (IL-6) is a pro-inflammatory cytokine whose levels are increased upon activation of various immune system cells during inflammation in RA, predominantly macrophages and T cells. It has pleiotropic effects in disease via its key role in the acute phase response and is heavily involved in governing the transition from acute to chronic inflammation. It does this by modifying the composition of the white blood cell infiltrate in the inflammatory space, moving it from neutrophils to monocyte/macrophages (see, e.g., Gabay, 2006). In addition, IL-6 exerts stimulatory effects on T- and B-cells, thus favouring chronic inflammatory responses, as well as on osteoclasts, thus promoting the turnover of bone. These effects are involved in the pathology of a broad range of autoimmune/inflammatory diseases beyond RA, including systemic lupus erythematosus, atherosclerosis, psoriasis, psoriatic arthritis, asthma, chronic obstructive pulmonary disease (COPD), Sjogren's syndrome, atherosclerosis, and inflammatory bowel disease, as well as in cancers such as multiple myeloma and prostate cancer.

In addition, IL-6 has been implicated in diseases involving bone loss (e.g., osteoporosis), diseases mediated by fibrosis (e.g., systemic sclerosis), diabetes, transplant rejection, various cancers (including, e.g., multiple myeloma, lymphoma, prostate cancer), neurodegenerative diseases (e.g., Alzheimer's), psychiatric disorders (e.g., depression), and certain rare vasculitides (e.g., Behçet's disease). For a full review, see, e.g., Rincon, 2012.

The interferon regulatory factors (IRFs) consist of a family of transcription factors with diverse functions in the transcriptional regulation of cellular responses in health and diseases. IRFs commonly contain a DNA-binding domain in the N-terminus, with most members also containing a C-terminal IRF-associated domain that mediates protein-protein interactions. Ten IRFs and several virus-encoded IRF homologs have been identified in mammals. IRFs are activated in response to endogenous and microbial stimuli during an immune response, and selectively and cooperatively modulate the expression of key cytokine and transcription factors involved in a variety of inflammatory processes. For example, stimulation of the receptor for bacterial lipopolysaccharide, TLR-4 activates a signalling cascade which activates both NFκB and IRF-5, whilst IRF-7 is activated by a process involving the STAT family of transcription factors, which are also, but independently, activated by IL-6.

The activation of the IRFs leads to a number of downstream effects including the specification of macrophage fate (see, e.g., Krausgruber et al., 2011), T helper cell differentiation (see, e.g., Zhang et al., 2012) and B-cell proliferation (see, e.g., Minamino et al., 2012). These diverse roles in disease are underlined by data from animal knockout models which show, for example, reduced levels of IL-6 and TNFα in response to inflammatory stimuli (see e.g., Takaoka et al., 2005).

In addition to the biological roles of the IRFs described above, several IRF family members have been genetically associated with predisposition to inflammatory conditions. For example, polymorphisms in IRF-3 and IRF-7 are associated with susceptibility to systemic lupus erythematosus (see, e.g., Akahoshi et al., 2008; Fu et al., 2011). In addition, IRF-5, which controls the fate of macrophages, is associated with susceptibility to RA, systemic lupus erythematosus, Wegener's Granulomatosis, Sjogren's syndrome, and systemic sclerosis (see, e.g., Sharif et al., 2012; Hu et al., 2011).

Treatment of Rheumatoid Arthritis

Early therapies for RA focussed on controlling the symptoms of the disease, mainly by reduction of inflammation, rather than retarding disease progression. These drugs included NSAIDs such as aspirin, diclofenac, and naproxen. Inflammation was further controlled by glucocorticoids, and their combination with NSAIDs provided reasonably effective short-term control of the inflammation. More recently, a more aggressive approach to treating RA has been introduced starting at disease onset, using so-called disease-modifying anti-rheumatic drugs (DMARDs), which act to slow or even prevent disease progression. These include a number of older drugs, including gold salts; sulfasalazine; antimalarials such as hydroxychloroquine; D-penicillamine; immunosuppressants such as mycophenolic acid, azathioprine, cyclosporine A, tacrolimus and sirolimus; minocycline; leflunomide; and most importantly, methotrexate (see, e.g., Smolen et al., 2003).

Methotrexate is now the gold-standard therapy for clinical trial comparisons, and is generally used in combination with newer therapies. It is effective in most patients but, in common with all of the above agents, has significant gastrointestinal side effects, which lead to roughly 50% of patients eventually having to cease treatment (see, e.g., Mount et al., 2005). A further drawback of these older DMARDs is the length of time taken for the drug to start acting, ranging from weeks with methotrexate, to months with gold salts. Whilst full remissions only occur in about a quarter of patients, for those showing no effect it is not generally possible to stop therapy without suffering the risk of a more violent disease rebound (see, e.g., Smolen et al., 2003).

In recent years, the treatment of RA has been revolutionised by the advent of biological agents which target specific inflammatory pathways. Several biological agents are currently approved for use in RA including anti-IL-6 and IL-1 biologics such as tocilizumab (Actemra®) and anakinra (Kineret®) (see, e.g., Scott et al., 2010). However, the first and most important of the biological agents are the anti-tumour necrosis factor (anti-TNF) therapies.

Anti-TNFα therapies are the market-leading treatment for RA. A variety of anti-TNFα agents are available including neutralising antibodies such as infliximab (Remicade®; J&J and Schering Plough) and adalimumab (Humira®; Abbott), or decoy receptors such as etanercept (Enbrel®; Amgen and Wyeth), both of which represent validated and highly effective treatments for RA as well as other diseases such as Crohn's disease and psoriasis. A number of other inflammatory and autoimmune disorders are also being investigated as potential targets. Other approaches to blocking the action of TNFα include the pegylated anti-TNFα fragment certolizumab (Cimzia®, UCB). All of these therapies act, ultimately, to prevent the activation of the downstream effectors of TNFα described above, including NFκB. However, in spite of their market success, the anti-TNFα therapies suffer from a number of side-effects including increased risk of certain malignancies such as lymphoma and serious infections such as *Legionella* and *Listeria*, as well as increased risk of heart failure, Hepatitis B reactivation, and demyelinating disease.

Finally, and most recently, a JAK kinase inhibitor, tofacitinib (Xeljanz®, Pfizer) has supplemented the range of RA treatments. However, tofacitinib suffers from a number of safety concerns including increased risk of serious infections as well as increased risk of gastrointestinal perforations, liver damage, and certain cancers, that are likely to limit its use in man (see, e.g., O'Shea et al., 2013).

As such, there remains a need for new and improved therapies for RA and other inflammatory diseases with a particular focus on improved safety.

The Osteoimmune System and Bone Disorders

The osteoimmune system is term for the combined and related interplay between the immune system and the skeletal system.

Under normal physiological conditions, the skeletal system provides support, mobility, protection for vital organs, and a mineral reservoir for calcium and phosphate. In order to achieve and adapt to these functions, the skeleton exists in a dynamic equilibrium characterized by continuous osteoclast-mediated bone resorption and osteoblast-mediated bone deposition (see, e.g., Karsenty et al., 2002). This biological process has been termed bone "remodelling" and occurs in coupled fashion with osteoblasts producing the key osteoclast differentiation factors, including RANKL, described above, and osteoclasts promoting bone formation by producing osteoclastic mediators as they degrade bone.

Both innate and adaptive immune cells exert effects on osteoclasts and osteoblasts through a variety of cell-surface and secreted mediators (see, e.g., Takayanagi, 2009). Activation of the RANKL receptor (RANK) on osteoclast precursors starts a cascade of transcriptional changes which results in the formation of osteoclasts and the expression of the machinery needed for bone resorption including molecules needed for attachment to bone, acid secretion, and proteolysis. Many of the transcription factors important for osteoclast differentiation are key regulators of immune responses, such as NFκB and nuclear factor of activated T cells c1 (NFATc1) and this process is also potentiated by factors involved in inflammation such as TNFα and IL-6.

In addition to its critical role in the progression and pathogenesis of RA, the osteoimmune system plays a critical role in a number of other diseases including osteoporosis and other bone disorders and cancer (see, e.g., Dallas et al., 2011).

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis also arises in association with inflammatory diseases such as rheumatoid arthritis, endocrine diseases such as thyrotoxicosis, and with certain drug treatments such as treatment with glucocorticoids. Indeed, osteoporosis-related fragility fractures represent one of the most important complications that may occur in patients with rheumatic diseases such as RA, systemic lupus erythematosus, and ankylosing spondylitis.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

IL-6, TNFα, and RANKL signalling have been shown to play a major role in osteoclast over-activity and a consequent increase in bone loss (see, e.g., Tanaka et al., 2003; Roodman, 2006). The use of drugs which affect these pathways have been validated by the completion of clinical trials of the monoclonal antibody against RANKL, AMG-162 (Denosumab®, Amgen), for the treatment of osteoporosis/multiple myeloma, as well as by an increasing body of evidence that shows that the anti-TNFα and anti-IL-6 therapies also prevent bone loss in arthritic diseases (see, e.g., Ogata et al., 2012; Billau, 2010).

The Osteoimmune System and Cancer

Many types of cancer affect bone. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common sources are multiple myeloma, breast carcinoma, and prostate carcinoma. The most common tumours associated with hypercalcaemia are multiple myeloma, breast carcinoma, and lung carcinoma.

As described above, RANK/RANKL signalling is essential for osteoclast formation and bone resorption that occurs during skeletal remodelling. While physiological levels of RANK/RANKL signalling stimulate the proliferation and cell survival of mammary epithelial cells, aberrant RANK/RANKL signalling in these tissues has recently been shown to influence the onset and progression of breast tumorigenesis and blocking RANKL signalling using denosumab (Xgeva®, Amgen) has been shown to be an effective in preventing the secondary complications of bone metastases, such as pathologic fracture, and hypercalcaemia in patients with breast cancer (see, e.g., Steger et al., 2011).

Therapies that block RANK/RANKL signalling may also decrease the ability of osteotropic cancers to metastasize to bone. Signalling through RANK on the surface of human epithelial tumour cells as well as melanoma cells has been shown to induce a chemotactic response in these tumour cells whilst in a murine model of melanoma metastasis, therapeutic treatment of mice with osteoprotegrin, which neutralizes the RANKL receptor, RANK, significantly reduced tumour burden within the bones but not other organs.

In addition to a role for RANKL in cancer, there is growing evidence that activation of NFκB via molecules such as TNFα can play a major role in the promotion and progression of both haematological malignancies, such as myeloma and lymphomas, and solid tumours, such as breast, prostate, and lung cancer (see, e.g., Baud et al., 2009). There is also rising awareness of the role and importance of inflammation and the osteoimmune system in cancer and in the development of resistance to radiotherapy and to chemotherapeutic agents. Furthermore, it has been suggested that inflammation is in fact one of the basic hallmarks of cancer (see, e.g., Mantovani, 2009). Improving the efficacy of anti-cancer treatments by prevention of NFκB activation is therefore a promising strategy to augment existing therapeutic regimes and is currently under investigation, most notably for the treatment of multiple myeloma.

Defects in the normal apoptotic pathways are also implicated in the development and progression of tumour cell growth as well as in inflammation. Apoptosis (programmed cell death) plays a key role in the removal of abnormal cells; defects in the signalling cascades, which would normally lead to its induction, play a key role in oncogenesis. Radiotherapy and many chemotherapeutic agents act by causing cellular damage, which would normally induce apoptosis; defects in the pathway will therefore also reduce the effectiveness of such agents. The most important effector molecules in the signalling pathway leading to apoptosis are known as the caspases, which may be triggered by a number of stimuli, including TNFα binding to its receptor. Mutations in the genes which encode for the caspases have been found in a number of tumour types, including gastric, breast, renal cell, and cervical cancers as well as commonly in T-cell lymphoblastic lymphoma and basal cell ameloblastomas (see, e.g., Philchenkov et al., 2004). Compounds which activate caspases, and thus sensitise cells to apoptosis, would be highly effective as cancer therapies either as single agents or in enhancing the effectiveness of existing cancer chemotherapy and radiotherapy.

Agents that Prevent Inflammation Disrupt the Osteoimmune System

The inventors have identified new compounds which, for example, prevent inflammation and/or bone loss, and thus may be used in the treatment of diseases with an inflammatory or autoimmune component, including, for example, rheumatoid arthritis, inflammatory bowel disease, systemic lupus erythematosus, atherosclerosis, asthma, chronic obstructive pulmonary disease (COPD), uveitis, pelvic inflammatory disease, endometriosis, psoriasis and psoriatic arthritis; diseases which involve bone loss, including, for example, bone loss associated with rheumatoid arthritis, osteoporosis, Paget's disease of bone, and multiple myeloma; as well as cancer associated with activation of NFκB, with aberrant NFκB signalling, or with inflammation or IL-6 overproduction, including haematological malignancies such as multiple myeloma, leukaemia, T-cell lymphoblastic lymphoma, and other lymphomas (e.g., non-Hodgkin's Lymphoma), and solid tumours such as bladder cancer, breast cancer (female and/or male), colon cancer, kidney cancer, lung cancer, pancreatic cancer, prostate cancer, brain cancer, skin cancer, thyroid cancer, and melanoma; cancer associated with the inactivation or impairment of caspase-mediated cell death, such as gastric cancer, breast cancer, renal cancer, cervical cancer, and basal cell ameloblastomas; conditions associated with modulated activity of IRF-5 including Wegener's granulomatosis and systemic sclerosis; fibrosis associated with overproduction of IL-6, such as systemic sclerosis or scleroderma; neurodegenerative diseases associated with IL-6 overproduction, such as Alzheimer's disease; psychiatric disorders also associated with IL-6 overproduction, such as depression; diseases of angiogenesis associated with IL-6 overproduction such as age-related macular degeneration and diabetic retinopathy, IL-6 associated hyperplasias such as Castleman's disease and certain rare vasculitides associated with IL-6 overproduction, such as Behçet's disease.

Without wishing to be bound by any particular theory, the inventors believe that this action may be via a mechanism that involves blocking TNFα, and/or RANKL-signalling and/or IRF activity and/or inhibition of IL-6 production.

Known Compounds

Wang et al., 2010, describes certain compounds which apparently are high-affinity and selective dopamine $D^3$ receptor full agonists. Examples of compounds shown therein include the following (see, e.g., pages 18-19 and 48-50 therein):

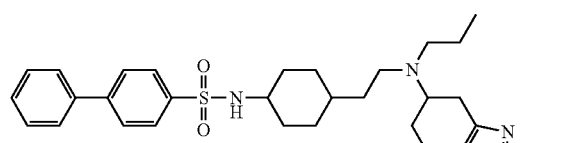

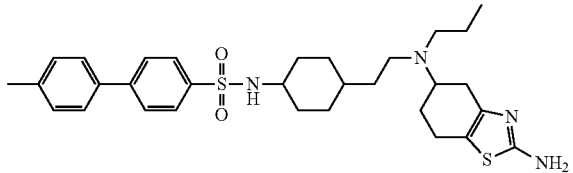

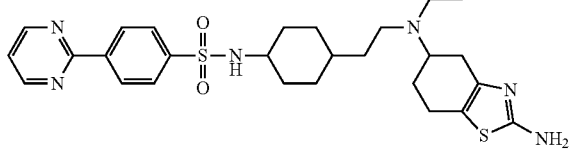

Chen et al., 2012 describes similar compounds.

Tsutsumi et al., 2005, describes certain compounds which apparently show DPP-IV inhibitory activity and apparently are useful in the treatment of type II diabetes and obesity. The following compound is shown as Example 89 on page 192 therein:

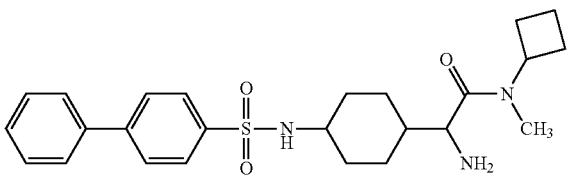 [SMILES: CN(C(=O)C(N)C1CCC(NS(=O)(=O)c2ccc(-c3ccccc3)cc2)CC1)C1CCC1]

Hadida et al., 2007 describes certain compounds which allegedly are useful as modulators of ATP-binding cassette ("ABC") transporters or fragments thereof, including Cystic Fibrosis Transmembrane Conductance Regulator ("CFTR"). The following compound is shown as Example 208 on page 77 therein:

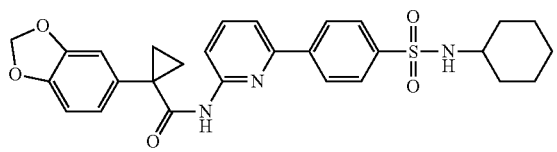 [SMILES: O=C(Nc1cccc(-c2ccc(S(=O)(=O)NC3CCCCC3)cc2)n1)C1(c2ccc3c(c2)OCO3)CC1]

Ralston et al., 2005, describes certain biphenyl-4-sulfonic amides for use: to inhibit osteoclast survival, formation, and/or activity; to inhibit conditions mediated by osteoclasts and/or characterised by bone resorption; in the treatment of bone disorders such as osteoporosis, rheumatoid arthritis, cancer associated bone disease, and Paget's disease; and in the treatment of conditions associated with inflammation or activation of the immune system. Examples of compounds shown therein include the following:

(ABD-246)

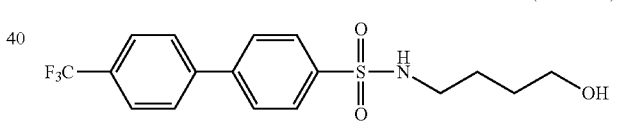

(ABD-256)

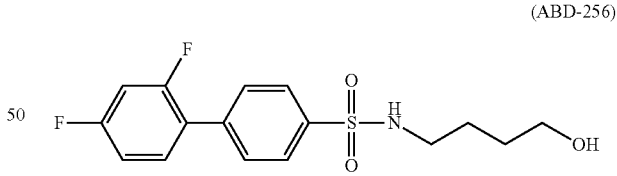

(ABD-278)

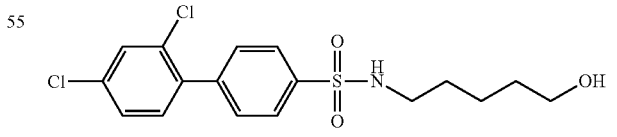

(ABD-284)

(ABD-295)

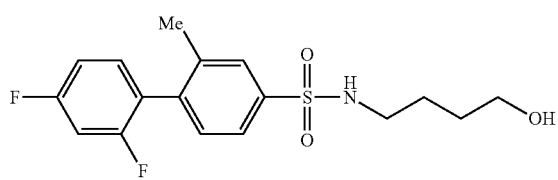

Greig et al., 2006, describes similar compounds.

Greig et al., 2008, describes certain biphenyl-4-sulfonic acid amides for the treatment of inflammation and/or joint destruction and/or bone loss; disorders mediated by excessive and/or inappropriate and/or prolonged activation of the immune system; inflammatory and autoimmune disorders, for example, rheumatoid arthritis, psoriasis, psoriatic arthritis, chronic obstructive pulmonary disease (COPD), atherosclerosis, inflammatory bowel disease, and ankylosing spondylitis; and disorders associated with bone loss, such as bone loss associated with excessive osteoclast activity in rheumatoid arthritis, osteoporosis, cancer associated bone disease, and Paget's disease. Examples of compounds shown therein include the following:

(ABD455)

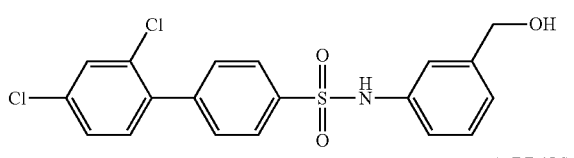

(ABD456)

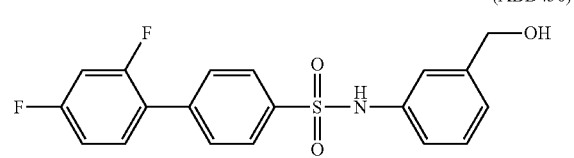

(ABD465)

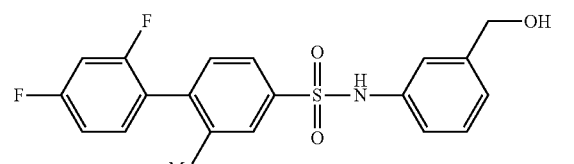

(ABD466)

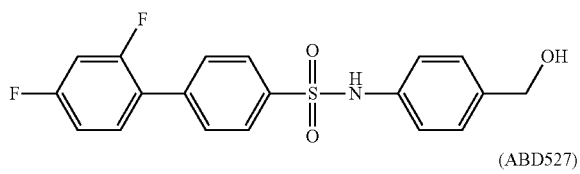

(ABD527)

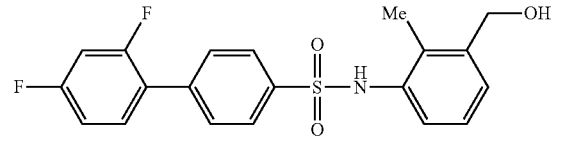

Greig et al., 2010b, describes certain biphenyl-4-sulfonic acid amides for the treatment of inflammation and/or joint destruction and/or bone loss; disorders mediated by excessive and/or inappropriate and/or prolonged activation of the immune system; inflammatory and autoimmune disorders, for example, rheumatoid arthritis, psoriasis, psoriatic arthritis, chronic obstructive pulmonary disease (COPD), atherosclerosis, inflammatory bowel disease, and ankylosing spondylitis; disorders associated with bone loss, such as bone loss associated with excessive osteoclast activity in rheumatoid arthritis, osteoporosis, cancer-associated bone disease, and Paget's disease; and cancer, such as a haematological malignancy and a solid tumour. Examples of compounds shown therein include the following:

(ABD707)

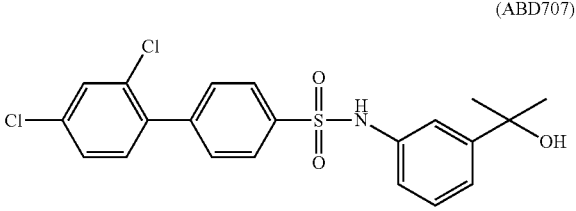

(ABD708)

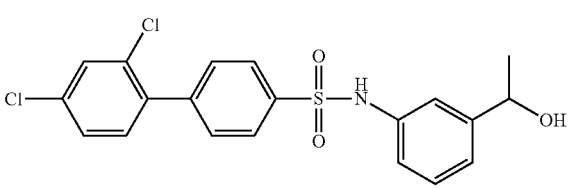

(ABD709)

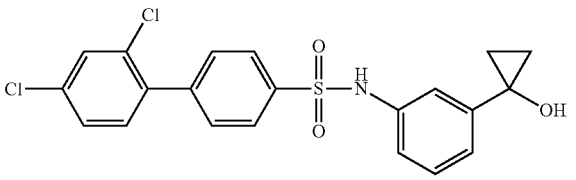

Greig et al., 2013 describes similar compounds.

Greig et al., 2010a, describes certain biphenyl-4-sulfonic acid amides for the treatment of inflammation and/or joint destruction and/or bone loss; disorders mediated by excessive and/or inappropriate and/or prolonged activation of the immune system; inflammatory and autoimmune disorders, for example, rheumatoid arthritis, psoriasis, psoriatic arthritis, chronic obstructive pulmonary disease (COPD), atherosclerosis, inflammatory bowel disease, and ankylosing spondylitis; disorders associated with bone loss, such as bone loss associated with excessive osteoclast activity in rheumatoid arthritis, osteoporosis, cancer-associated bone disease, and Paget's disease; and cancer, such as a haematological malignancy and a solid tumour. Examples of compounds shown therein include the following:

(ABD599)

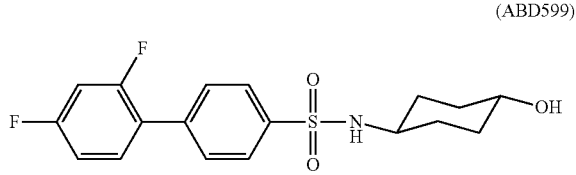

-continued (ABD655)
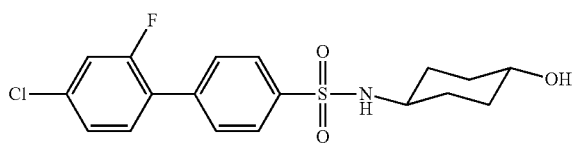

(ABD683)
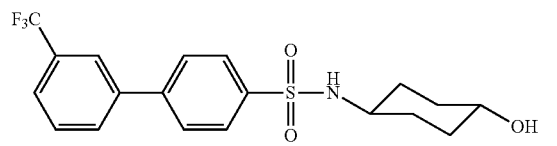

(ABD703)
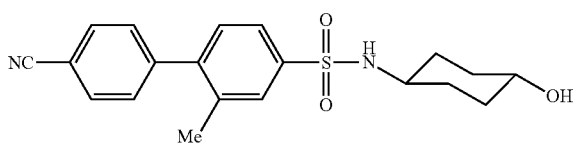

(ABD712)
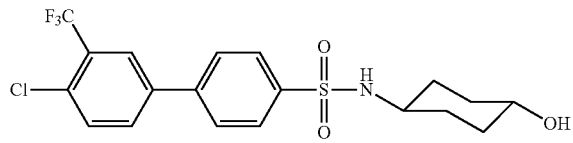

(ABD714)
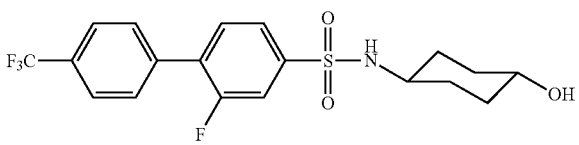

(ABD732)
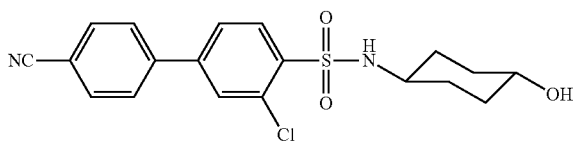

(ABD735)
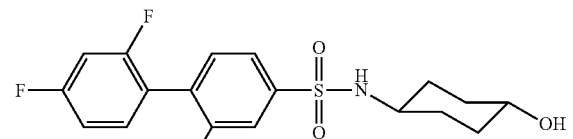

(ABD742)
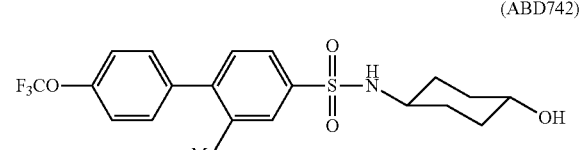

(ABD777)

-continued (ABD836)
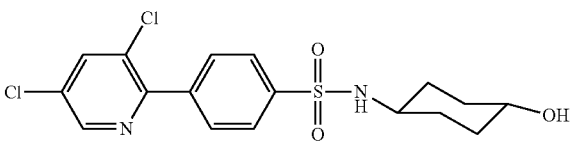

(ABD899)
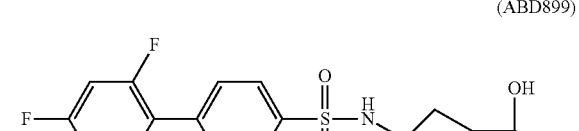

(ABD900)
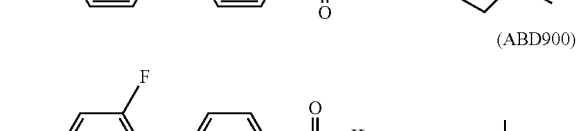

New Compounds with Improved Properties

The HMC compounds described herein are protected against several toxic liabilities that are present in the known compounds, especially those shown in Greig et al., 2010a and show improved efficacy in models of disease.

Without wishing to be bound to any particular theory, the inventors believe that the particular combinations of substituents and their positions on the biaryl ring structure give rise to extraordinary properties. In addition to substantial improvements in acute in vivo toxicology, these combinations protect the compounds from general cytotoxicity, genotoxicity, and cardiovascular safety liabilities seen in the known compounds. Specifically, the HMC compounds described herein are negative for genotoxicity, show a substantial improvement in general cytotoxicity, and are substantially protected against inhibition of the human Ether-à-go-go related gene (hERG), which represents a major cardiovascular safety liability.

If a drug is to be used in the clinic, it must have a suitable safety and efficacy profile. It must show adequate acute safety to allow dosing to humans without the expectation of serious general side-effects. In addition, it must not cause genetic damage (genotoxicity) because agents that are genotoxic can act as carcinogens in humans. A clinically acceptable drug should also not inhibit hERG, an ion-channel which, when inhibited, can cause a fatal heart disorder known as long QT syndrome. Alongside these safety properties, the drug must be sufficiently potent against the biological target to give the desired therapeutic effect; it must have a sufficient solubility to be absorbed from the gastrointestinal tract; and it must have sufficient stability to remain in the circulation long enough to reach the biological target.

The HMC compounds described herein demonstrate improved efficacy in models of rheumatoid arthritis, for example, as compared with the compounds shown in Greig et al., 2010a. This is demonstrated both by a greater magnitude of effect on disease, as well as greater potency, both of which are seen, importantly, when the HMC compounds are administered when disease is already established. This mirrors the clinical setting for the use of these compounds. Moreover these effects are seen without overt toxicity.

The reduction of toxicological properties (adverse effects) of a drug is a developmental barrier of equal challenge and importance as compared to the optimization of pharmacodynamics (action of the drug on the body) and pharmacokinetic (action of the body on the drug) properties. The HMC compounds described herein provide substantial advantages as oral therapeutic agents (as compared to the known compounds) by improving acute general in vivo toxicology, genotoxic and cytotoxic safety, and cardiovascular safety, with little or no change in in vivo pharmacokinetics or loss of potency against the biological target.

The HMC compounds described herein combine the required characteristics of orally active agents for the treatment of, for example, chronic inflammatory conditions, bone loss, and cancer.

SUMMARY OF THE INVENTION

Figure 1:
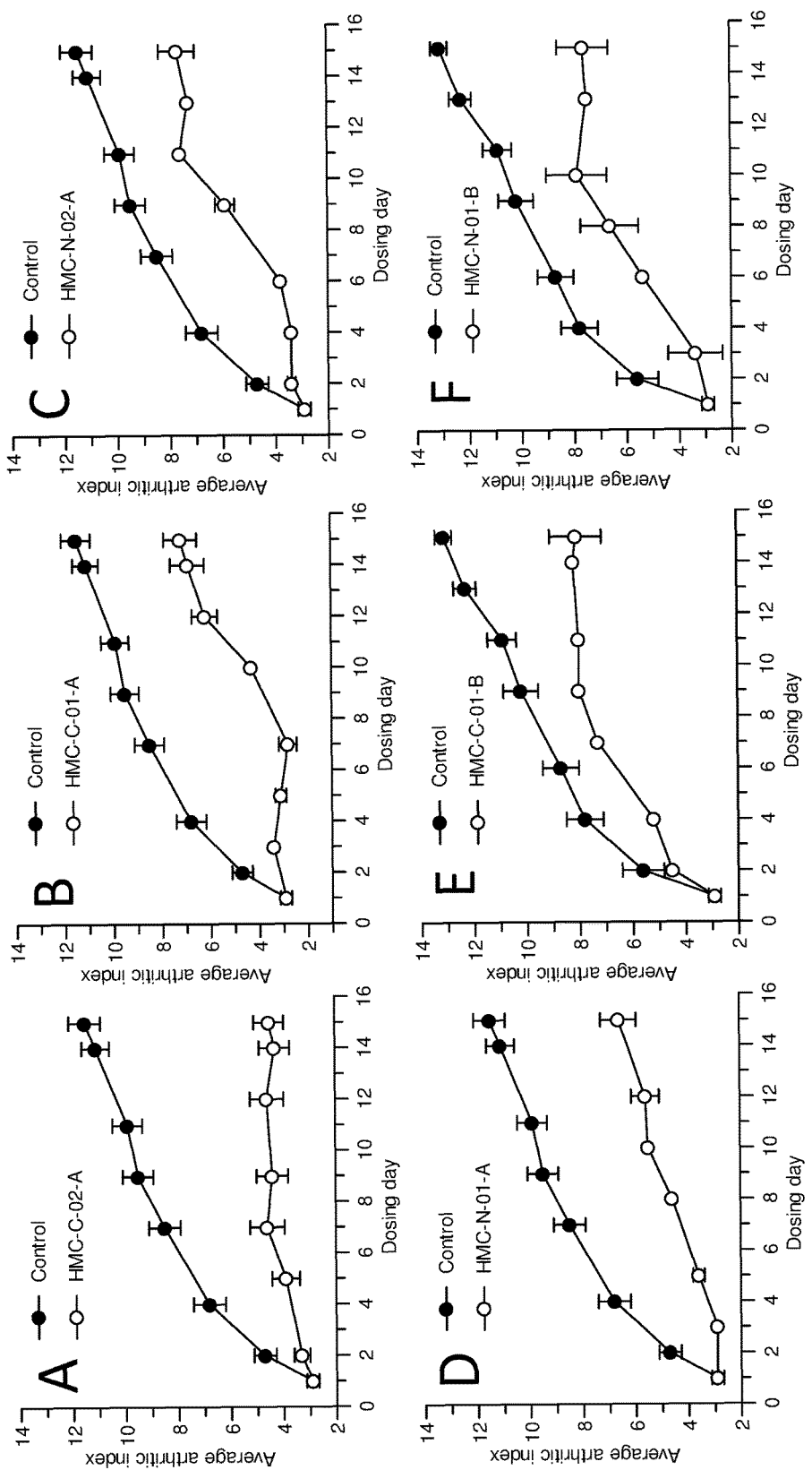
FIG. 1 shows six graphs, each of average arthritic index as a function of time (dosing day) for test compound dosed at 10 mg/kg/day by oral gavage (open circles) and control (solid circles), for each of: (A) HMC-C-02-A (top left), (B) HMC-C-01-A (top middle), (C) HMC-N-02-A (top right), (D) HMC-N-01-A (bottom left), (E) HMC-C-01-B (bottom middle), (F) HMC-N-01-B (bottom right), as described in Biological Study 6 below.

One aspect of the invention pertains to certain substituted N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds (collectively referred to herein as HMC compounds), as described herein.

Another aspect of the invention pertains to a composition (e.g., a pharmaceutical composition) comprising an HMC compound, as described herein, and a pharmaceutically acceptable carrier or diluent.

Another aspect of the invention pertains to a method of preparing a composition (e.g., a pharmaceutical composition) comprising the step of mixing an HMC compound, as described herein, and a pharmaceutically acceptable carrier or diluent.

Another aspect of the present invention pertains to an HMC compound, as described herein, for use in a method of treatment of the human or animal body by therapy, for example, for use a method of treatment of a disorder (e.g., a disease) as described herein.

Another aspect of the present invention pertains to use of an HMC compound, as described herein, in the manufacture of a medicament for treatment, for example, treatment of a disorder (e.g., a disease) as described herein.

Another aspect of the present invention pertains to a method of treatment, for example, of a disorder (e.g., a disease) as described herein, comprising administering to a patient in need of treatment a therapeutically effective amount of an HMC compound, as described herein, preferably in the form of a pharmaceutical composition.

Another aspect of the present invention pertains to a kit comprising (a) an HMC compound, as described herein, preferably provided as a pharmaceutical composition and in a suitable container and/or with suitable packaging; and (b) instructions for use, for example, written instructions on how to administer the compound.

Another aspect of the present invention pertains to an HMC compound obtainable by a method of synthesis as described herein, or a method comprising a method of synthesis as described herein.

Another aspect of the present invention pertains to an HMC compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which may conveniently be described as substituted N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds.

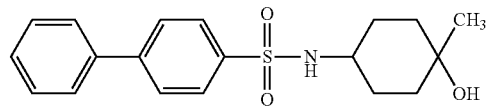

N-(4-hydroxy-4-methyl-cyclohexyl)-4-phenyl-benzenesulfonamide

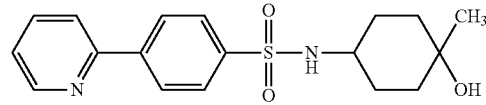

N-(4-hydroxy-4-methyl-cyclohexyl)-4-(2-pyridyl)benzenesulfonamide

Thus, one aspect of the present invention is a compound selected from compounds of the following formulae, or a pharmaceutically acceptable salt, hydrate, or solvate thereof (for convenience, collectively referred to herein as "HMC compounds"):

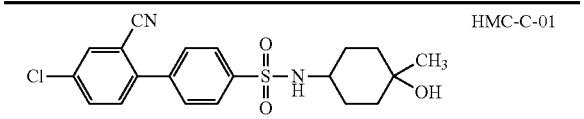

HMC-C-01

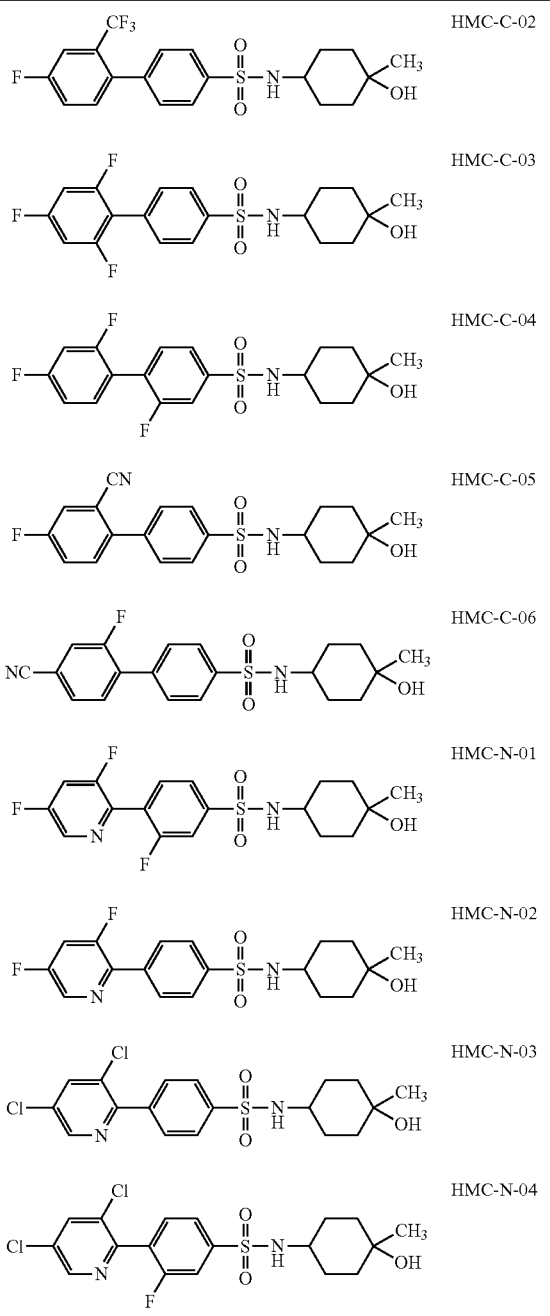

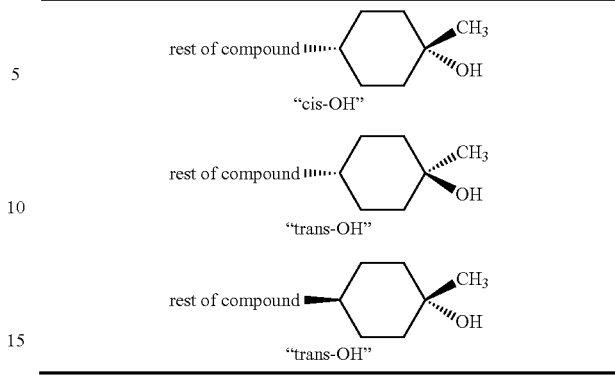

Unless otherwise indicated, it is intended that all such conformations are encompassed by a reference to a compound that does not specify a particular conformation.

In one embodiment, the compound is in the "trans-OH" conformation, as in, for example, the following compounds:

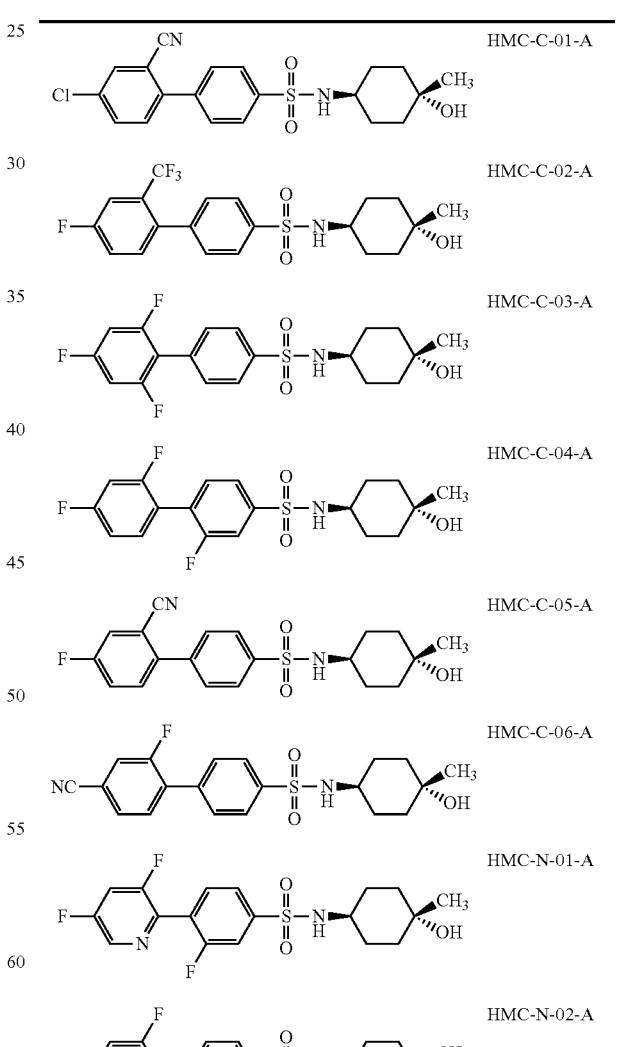

Note that the substituents on one side of the cyclohexyl ring (i.e., —OH and —CH₃ on the right-hand side) may be positioned "trans"/"cis" or "cis"/"trans" with respect to the rest of the molecule (that is, on the cyclohexyl ring to which they attached, with respect to the rest of the compound which is attached at the para position of the cyclohexyl ring).

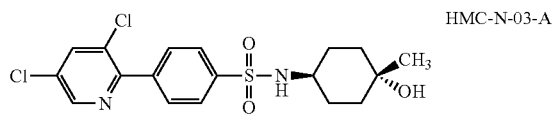

HMC-N-03-A

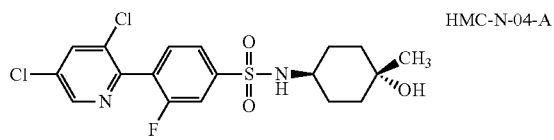

HMC-N-04-A

In one embodiment, the compound is in the "cis-OH" conformation, as in, for example, the following compounds:

HMC-C-01-B

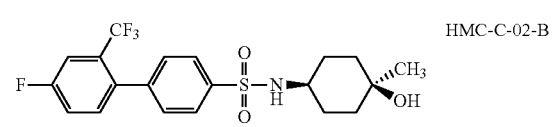

HMC-C-02-B

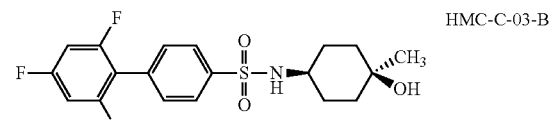

HMC-C-03-B

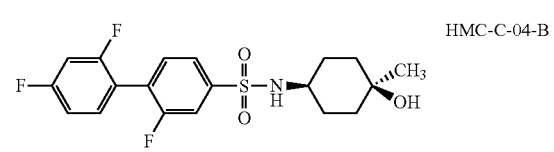

HMC-C-04-B

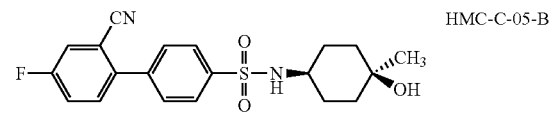

HMC-C-05-B

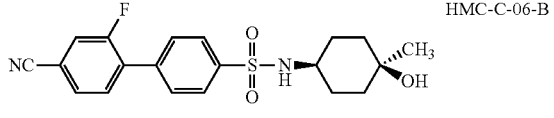

HMC-C-06-B

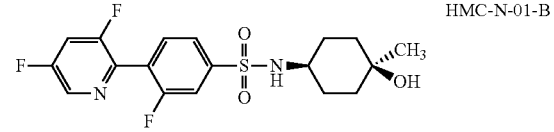

HMC-N-01-B

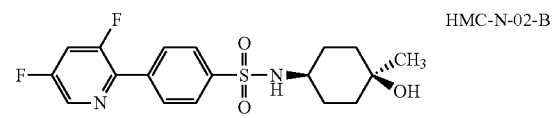

HMC-N-02-B

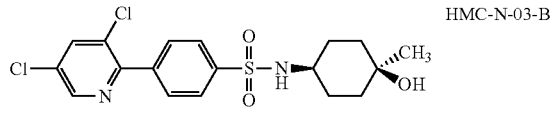

HMC-N-03-B

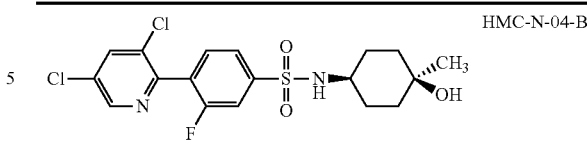

HMC-N-04-B

Note also that the cyclohexane ring may take a "chair", "boat", or "twist" conformation, and that interconversion between the conformations is possible. Unless otherwise indicated, it is intended that all such conformations (e.g., "chair", "boat", "twist", "OH is axial", "OH is equatorial", etc.) are encompassed by a reference to a compound that does not specify a particular conformation.

Substantially Purified Forms

One aspect of the present invention pertains to HMC compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any conformational form. For example, in one embodiment, the substantially purified form refers to a mixture of conformational forms, i.e., purified with respect to other compounds. In one embodiment, the substantially purified form refers to one conformational form. In one embodiment, the substantially purified form refers to a mixture of conformational forms. In one embodiment, the substantially purified form refers to an equimolar mixture of conformational forms.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than conformational forms. In one embodiment, the contaminants refer to other compounds and other conformational forms.

In one embodiment, the substantially purified form is at least 60% conformationally pure (i.e., 60% of the compound, on a molar basis, is the desired conformation, and 40% is the undesired conformational form(s))), e.g., at least 70% conformationally pure, e.g., at least 80% conformationally pure, e.g., at least 90% conformationally pure, e.g., at least 95% conformationally pure, e.g., at least 97% conformationally pure, e.g., at least 98% conformationally pure, e.g., at least 99% conformationally pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

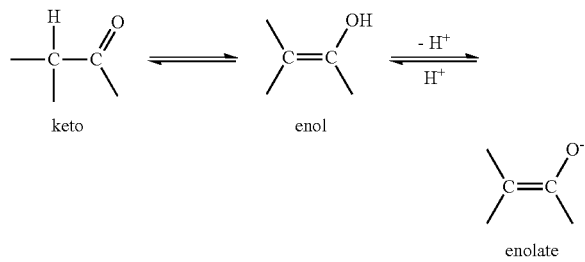

Note that specifically included in the term "isomer" are compounds with one or more isotopic substitutions. For example, H may be in any isotopic form, including $^1H$, $^2H$ (D), and $^3H$ (T); C may be in any isotopic form, including $^{11}C$, $^{12}C$, $^{13}C$, and $^{14}C$; O may be in any isotopic form, including $^{15}O$, $^{16}O$ and $^{18}O$; N may be in any isopotic form including $^{14}N$ and $^{15}N$; F may be in any isopotic form including $^{18}F$ and $^{19}F$ and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4+$) and substituted ammonium ions (e.g., $NH_3R+$, $NH_2R_2+$, $NHR_3+$, $NR_4+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4+$.

If the compound is cationic, or has a functional group which may be cationic (e.g., —$NH_2$ may be —$NH_3+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O•).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Chemical Synthesis

Methods for the chemical synthesis of HMC compounds are described herein. These and/or other well-known methods may be modified and/or adapted in known ways in order to facilitate the synthesis of additional HMC compounds described herein.

Compositions

One aspect of the present invention pertains to a composition (e.g., a pharmaceutical composition) comprising an HMC compound, as described herein, and a pharmaceutically acceptable carrier, diluent, or excipient.

In one embodiment, the composition further comprises one or more (e.g., 1, 2, 3, 4) additional therapeutic agents, as described herein.

Another aspect of the present invention pertains to a method of preparing a composition (e.g., a pharmaceutical composition) comprising admixing an HMC compound, as described herein, and a pharmaceutically acceptable carrier, diluent, or excipient.

Another aspect of the present invention pertains to a method of preparing a composition (e.g., a pharmaceutical composition) comprising admixing an HMC compound, as described herein; one or more (e.g., 1, 2, 3, 4) additional therapeutic agents, as described herein; and a pharmaceutically acceptable carrier, diluent, or excipient.

Uses

The HMC compounds, as described herein, are useful, for example, in the treatment of disorders (e.g., diseases) including, for example, the disorders (e.g., diseases) described herein.

Use in Methods of Therapy

Another aspect of the present invention pertains to an HMC compound, as described herein, for use in a method of treatment of the human or animal body by therapy, for example, for use a method of treatment of a disorder (e.g., a disease) as described herein.

Another aspect of the present invention pertains to an HMC compound, as described herein, in combination with one or more (e.g., 1, 2, 3, 4) additional therapeutic agents, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of an HMC compound, as described herein, in the manufacture of a medicament for treatment, for example, treatment of a disorder (e.g., a disease) as described herein.

In one embodiment, the medicament comprises the HMC compound.

Another aspect of the present invention pertains to use of an HMC compound, as described herein, and one or more (e.g., 1, 2, 3, 4) additional therapeutic agents, as described herein, in the manufacture of a medicament for treatment, for example, treatment of a disorder (e.g., a disease) as described herein.

In one embodiment, the medicament comprises the HMC compound and the one or more (e.g., 1, 2, 3, 4) additional therapeutic agents.

Methods of Treatment

Another aspect of the present invention pertains to a method of treatment, for example, of a disorder (e.g., a disease) as described herein, comprising administering to a patient in need of treatment a therapeutically effective amount of an HMC compound, as described herein, preferably in the form of a pharmaceutical composition.

Another aspect of the present invention pertains to a method of treatment, for example, of a disorder (e.g., a disease) as described herein, comprising administering to a patient in need of treatment a therapeutically effective amount of an HMC compound, as described herein, preferably in the form of a pharmaceutical composition, and one or more (e.g., 1, 2, 3, 4) additional therapeutic agents, as described herein, preferably in the form of a pharmaceutical composition.

Conditions Treated

In one embodiment, the treatment is treatment of an inflammatory disorder or an autoimmune disorder.

In one embodiment, the treatment is treatment of a disorder associated with inflammation and/or activation of the immune system.

In one embodiment, the treatment is treatment of a disorder mediated by excessive and/or inappropriate and/or prolonged activation of the immune system.

In one embodiment, the treatment is treatment of inflammation.

In one embodiment, the treatment is treatment of a disorder associated with inflammation or activation of the immune system.

In one embodiment, the treatment is treatment of rheumatoid arthritis; psoriasis; psoriatic arthritis; chronic obstructive pulmonary disease (COPD); asthma; atherosclerosis; inflammatory bowel disease; or ankylosing spondylitis.

In one embodiment, the treatment is treatment of rheumatoid arthritis.

In one embodiment, the treatment is treatment of psoriasis.

In one embodiment, the treatment is treatment of psoriatic arthritis.

In one embodiment, the treatment is treatment of chronic obstructive pulmonary disease (COPD).

In one embodiment, the treatment is treatment of asthma.

In one embodiment, the treatment is treatment of atherosclerosis.

In one embodiment, the treatment is treatment of ankylosing spondylitis.

In one embodiment, the treatment is treatment of inflammatory bowel disease.

In one embodiment, the treatment is prevention of an immune response leading to organ or graft rejection following transplant.

In one embodiment, the treatment is prevention of an inflammatory condition in which IRF-5 expression or activity is aberrant.

In one embodiment, the treatment is treatment of a tumour which over expresses TNFα, IL-1, IL-6, RANKL, and/or NFκB.

In one embodiment, the treatment is treatment of a tumour for which inhibition of TNFα, IL-1, RANKL, NFκB, IRFs such as IRF-3, -5 or -7 and/or IL-6 expression or activity or signalling facilitates or improves the action of cytotoxic tumouricidal agents.

In one embodiment, the treatment is treatment of a haematological malignancy.

In one embodiment, the treatment is treatment of multiple myeloma.

In one embodiment, the treatment is treatment of leukaemia; e.g., acute lymphoblastic leukaemia.

In one embodiment, the treatment is treatment of lymphoma; e.g., non-Hodgkin's Lymphoma, T-cell lymphoma (e.g., T-lymphoblastic lymphoma, extranodal T-cell lymphoma, cutaneous T-cell lymphoma, anaplastic large cell lymphoma, angioimmunoblastic T-cell lymphoma), and B-cell lymphoma (e.g., Hodgkin's lymphoma, non-Hodgkin's lymphoma) (e.g., diffuse large B-cell lymphoma, follicular lymphoma, mucosa-associated lymphatic tissue lymphoma, small cell lymphocytic lymphoma, mantle cell lymphoma, hairy cell leukaemia and Burkitt's lymphoma).

In one embodiment, the treatment is treatment of a solid tumour cancer, e.g., bladder cancer, breast cancer (female and/or male), colon cancer, renal cell carcinoma, kidney cancer, lung cancer, pancreatic cancer, gastric cancer, prostate cancer, brain cancer, skin cancer, thyroid cancer, basal cell ameloblastoma, or melanoma.

In one embodiment, the haematological malignancy (e.g., multiple myeloma, leukaemia, lymphoma, etc.) and the solid tumour cancer (e.g., cancer of the bladder, etc.) is associated with activation of NFκB, with aberrant NFκB signalling, or with inflammation.

In one embodiment, the haematological malignancy (e.g., multiple myeloma, leukaemia, lymphoma, etc.) and the solid tumour cancer (e.g., cancer of the bladder, etc.) is associated with inactivation or impairment of caspase induction or with aberrant caspase signalling.

In one embodiment, the treatment is treatment of a proliferative disorder; e.g., Castleman's disease.

In one embodiment, the treatment is treatment of a disease or disorder selected from: diseases having an inflammatory or autoimmune component, including asthma, atherosclerosis, allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including type I diabetes and associated complications, multiple sclerosis, arthritis, systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune haemolytic anaemia, paroxysmal cold hemoglobinuria, Behçet's disease, autoimmune thrombocytopenia, autoimmune neutropenia, pernicious anaemia, pure red cell anaemia, autoimmune coagulopathies, endometriosis, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996), skin diseases such as lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997), hypersensitivity lung diseases such as hypersensitivity pneumonitis (Sugiyama et al., 1995), and inflammation related to histamine release from basophils (Dvorak et al., 1996), such as hay fever, histamine release from mast cells (Galli et al., 1989), or mast cell tumours, types of type 1 hypersensitivity reactions (anaphylaxis, skin allergy, hives, gout, allergic rhinitis, and allergic gastroenteritis); ulcerative colitis or Crohn's disease; TNFα induced polycystic kidney disease (Li et al., 2008); or Cryopyrin-Associated Periodic Syndromes, including Muckle-Wells Syndrome.

In one embodiment, the treatment is treatment of a disorder mediated by osteoclasts.

In one embodiment, the treatment is treatment of a disorder characterised by excessive bone resorption.

In one embodiment, the treatment is treatment of a disorder associated with bone loss.

In one embodiment, the treatment is treatment of bone loss.

In one embodiment, the treatment is treatment of bone loss associated with inflammation.

In one embodiment, the treatment is treatment of bone loss not associated with inflammation.

In one embodiment, the treatment is treatment of bone loss associated with excessive osteoclast activation.

In one embodiment, the treatment is treatment of joint destruction.

In one embodiment, the treatment is treatment of joint destruction associated with inflammation.

In one embodiment, the treatment is treatment of joint destruction associated with excessive osteoclast activation.

In one embodiment, the treatment is treatment of bone loss associated with excessive osteoclast activation in rheumatoid arthritis, osteoporosis, cancer-associated bone disease, or Paget's disease.

In one embodiment, the treatment is treatment of bone loss associated with rheumatoid arthritis, osteoporosis, cancer-associated bone disease, or Paget's disease of bone.

In one embodiment, the treatment is treatment of rheumatoid arthritis, osteoporosis, cancer-associated bone disease, or Paget's disease of bone.

In one embodiment, the treatment is treatment of neoplasia of bones, whether as a primary tumour or as metastases, including osteosarcoma and osteoma (see, e.g., Zheng et al., 1998) and cancer-associated bone disease (e.g., hypercalcaemia of malignancy, bone metastases, osteolytic bone metastases, multiple myeloma, breast carcinoma).

In one embodiment, the treatment is treatment of hypercalcaemia caused by conditions associated with increased bone resorption, including: vitamin D intoxication, primary or tertiary hyperparathyroidism, immobilisation, and sarcoidosis.

In one embodiment, the treatment is treatment of aseptic loosening of prosthetic implants (e.g., artificial joints, e.g., knees, hips, etc., can loosen due to osteoclast activity driven by local inflammation) (see, e.g., Childs et al., 2001).

In one embodiment, the treatment is treatment of osteopetrosis, osteoarthritis, or ectopic bone formation.

In one embodiment, the treatment is treatment of a disorder associated with fibrosis, such as systemic sclerosis or scleroderma.

In one embodiment, the treatment is treatment of a rare vasculitide, such as Behçet's disease.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of inflammation includes the prophylaxis of inflammation, reducing the incidence of inflammation, reducing the severity of inflammation, alleviating the symptoms of inflammation, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, anti-inflammation agents, etc. Examples of treatments and therapies include chemotherapy (the administration of active agents, including, e.g., drugs; antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more additional therapeutic agents.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The HMC compounds described herein may also be used as part of an in vitro assay, for example, in order to determine whether a candidate host is likely to benefit from treatment with the compound in question.

The HMC compounds described herein may also be used as a standard, for example, in an assay, in order to identify other compounds, other anti-inflammation agents, etc.

Kits

One aspect of the invention pertains to a kit comprising (a) an HMC compound as described herein, or a composition comprising an HMC compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The HMC compound or pharmaceutical composition comprising the HMC compound may be administered to a subject by any convenient route of administration, whether systemically/peripherally or topically (i.e., at the site of desired action).

Routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one preferred embodiment, the route of administration is oral (e.g., by ingestion).

In one preferred embodiment, the route of administration is parenteral (e.g., by injection).

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. Furthermore, the subject/patient may be any of its forms of development, for example, a foetus.

In one preferred embodiment, the subject/patient is a human.

Formulations

While it is possible for the HMC compound to be administered alone, it is preferable to present it as a pharmaceutical formulation (e.g., composition, preparation, medicament) comprising at least one HMC compound, as described herein, together with one or more other pharmaceutically acceptable ingredients well known to those skilled in the art, including pharmaceutically acceptable carriers, diluents, excipients, adjuvants, fillers, buffers, preservatives, antioxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one HMC compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example, from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the HMC compounds, and compositions comprising the HMC compounds, can vary from patient to patient. Determining the optimal dosage will generally involve the balancing of the level of therapeutic benefit against any risk or deleterious side effects. The selected dosage level will depend on a variety of factors including the activity of the particular HMC compound, the route of administration, the time of administration, the rate of excretion of the HMC compound, the duration of the treatment, other drugs, compounds, and/or materials used in combination, the severity of the condition, and the species, sex, age, weight, condition, general health, and prior medical history of the patient. The amount of HMC compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the HMC compound is in the range of about 50 µg to about 20 mg (more typically about 100 µg to about 10 mg) per kilogram body weight of the subject per day. For pulmonary administration (e.g., by inhalation), a suitable dosage is in the range of about 50 ng to about 1 mg per kilogram body weight of the subject per day. Where the compound is a salt, an ester, an amide, a prodrug, or the like, the amount administered is calculated on the basis of the parent compound and so the actual weight to be used is increased proportionately.

Chemical Synthesis

Methods for the chemical synthesis of the HMC compounds are described herein. These and/or other well-known methods (see, e.g., Greig et al., 2010a; Bahmanyar et al., 2010) may be modified and/or adapted in known ways in order to provide alternative or improved methods of synthesis.

Synthesis 1

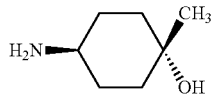

(1r,4,)-4-Amino-1-methylcyclohexan-1-ol

Palladium hydroxide (50% wet with water; 2.0 g) was added to a stirred solution of (1r,4r)-4-(dibenzylamino)-1-methylcyclohexanol (7.5 g, 24.2 mmol) in methanol (100 mL) in a 300 mL autoclave. The autoclave was charged with hydrogen (50 atm; ~5 MPa) and heated at 80° C. for 24 hours. The mixture was cooled and the catalyst filtered off. The filtrate was returned to the autoclave and palladium hydroxide (50% wet with water; 3.0 g) was added. The autoclave was charged with hydrogen (50 atm; ~50 MPa) and heated at 80° C. overnight. The mixture was cooled and filtered through celite and the filtrate was concentrated to give the title compound as an off-white gummy solid (3.2 g, quant.).

$^1$H NMR: (400 MHz; CDCl$_3$) δ 2.86-2.76 (1H, m), 1.84-1.76 (2H, m), 1.75-1.63 (2H, m), 1.55-1.43 (2H, m), 1.30-1.17 (5H, m).

Synthesis 1A

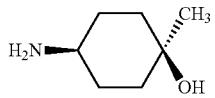

(1s,4s)-4-Amino-1-methylcyclohexan-1-ol

Four equal batches of (1s,4s)-4-dibenzylamino-1-methylcyclohexan-1-ol (each batch was 15 g, total 60 g) were separately debenzylated as follows: To (1s,4s)-4-dibenzylamino-1-methylcyclohexan-1-ol (15 g, 193.9 mmol) in ethanol (450 mL) was added 10% palladium hydroxide (15 g, 50% wet catalyst). The reaction mixtures were flushed with nitrogen followed by hydrogen gas and stirred under an atmosphere of hydrogen for 16 hours at room temperature. The solution was filtered through celite and which was washed with additional ethyl acetate. The filtrates from all four batches were combined and evaporated under reduced pressure to afford the title compound (23 g, 91.8% yield). The compound was used without further purification in the next step.

$^1$H NMR (400 MHz, CDCl$_3$) δ: 2.6 (m, 1H), 1.74-1.56 (m, 4H), 1.5-1.3 (m, 7H), 1.21 (s, 3H).

Synthesis 2

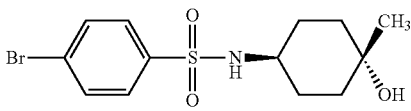

4-Bromo-N-((1r,4r)-4-hydroxy-4-methylcyclohexyl)benzenesulfonamide

Diisopropylethylamine (24 mL, 137.8 mmol) was added to a solution of (1r,4r)-4-amino-1-methylcyclohexanol (3.6 g, 27.86 mmol) in dichloromethane (150 mL) and the reaction mixture was cooled to 0° C. 4-Bromobenzene-1-sulfonyl chloride (7.83 g, 30.6 mmol) was added as solid and the reaction mixture was allowed to stir at room temperature for 4 hours. The reaction mixture was neutralized with 1 M hydrochloric acid and the compound was extracted into dichloromethane. The organic layer was separated, dried over sodium sulfate and concentrated under reduced pressure. The residue obtained was washed with pentane, filtered and dried to give the title compound (7 g, 72%).

$^1$H NMR: (400 MHz; CDCl$_3$) δ 7.74 (2H, d), 7.65 (2H, d), 4.77-4.61 (1H, m), 3.33-3.23 (1H, m), 1.85-1.75 (2H, m), 1.63-1.51 (2H, m), 1.49-1.30 (4H, m), 1.20 (3H, s).

LCMS: (Run time: 3.5 min): Retention time: 1.33 min (97%, MS (ESI) m/z 346 (M−H)$^+$).

Synthesis 3

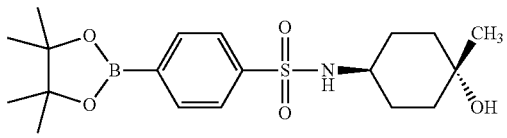

N-((1r,4r)-4-Hydroxy-4-methylcyclohexyl)-4-(4,4,5,5-tetramethyl-1,3,2-dioxaborolan-2-yl)benzenesulfonamide A solution of 4-bromo-N-((1r,4r)-4-hydroxy-4-methylcyclohexyl)benzenesulfonamide (9 g, 25.8 mmol), 4,4,4',4',5,5,5',5'-octamethyl-2,2'-bi(1,3,2-dioxaborolane) (9.87 g, 38.9 mmol) and potassium acetate (7.6 g, 77.5 mmol), in toluene (50 mL) was degassed using argon for 10 min. [1,1-Bis(diphenylphosphino) ferrocene]dichloropalladium(II) (1.8 g, 2.5 mmol) was added and the reaction mixture was degassed for another 10 min and stirred at 100° C. for 4 hours. The solvent was evaporated under reduced pressure and the compound was extracted into ethyl acetate. The organic layer was separated, dried over sodium sulfate and concentrated under reduced pressure to give the title compound (8 g, 78%) MS (ESI) m/z 394 (M−H)$^+$). For large scale batches, the compound was used without further purification. When this preparation was performed on a smaller scale, the residue was taken up in ether, filtered and the filtrate was concentrated to give the desired product.

Synthesis 4

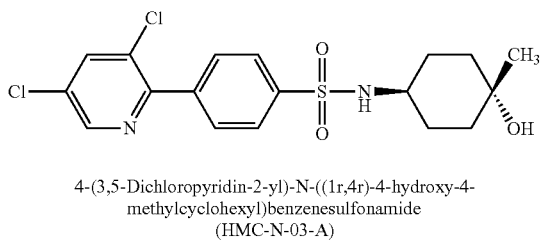

4-(3,5-Dichloropyridin-2-yl)-N-((1r,4r)-4-hydroxy-4-methylcyclohexyl)benzenesulfonamide
(HMC-N-03-A)

A mixture of dioxane and water (3:1; 20 mL) was degassed. 2,3,5-Trichloropyridine (1.65 g, 9.0 mmol), N-((1r,4r)-4-hydroxy-4-methylcyclohexyl)-4-(4,4,5,5-tetramethyl-1,3,2-dioxaborolan-2-yl)benzenesulfonamide (1.8 g, 4.6 mmol), $K_2CO_3$ (1.24 g, 9.0 mmol) and [1,1-bis(diphenylphosphino)ferrocene]dichloropalladium(II) (257 mg, 0.35 mmol) were added and the reaction mixture stirred at 120° C. in a microwave oven for 3 hours. The reaction mixture was concentrated, diluted with ethyl acetate and washed with water. The organic extracts were dried ($MgSO_4$) and concentrated to give a crude residue which was purified by flash column (eluent: 40 to 50% ethyl acetate in heptane). The product was purified further by crystallisation three times (ethyl acetate/heptane) to give the title compound (284 mg, 15%).

$^1$H NMR: (400 MHz; $CDCl_3$) δ 8.59 (1H, m), 7.97 (2H, d), 7.92-7.85 (3H, m), 4.62-4.55 (1H, m), 3.38-3.28 (1H, m), 1.92-1.76 (2H, m), 1.8-1.35 (7H, m), 1.22 (3H, s).

LCMS: mobile phase A: 0.05% trifluoroacetic acid in water, mobile phase B: 0.05% trifluoroacetic acid in acetonitrile; Column: YMC ODS A, C18 (50×4.6 mm) 3 uM; Flow rate: 1.2 mL/min; Temperature: Ambient. Run time: 4.5 min—starting solvent 20:80 B:A is increased linearly to 95:5 B:A over the first 3 min, held at 95:5 B:A for 0.5 min then immediately returned to 20:80 B:A for the last 1.5 min. Retention time: 2.50 min, m/z 415 (M+H)$^+$.

Synthesis 5

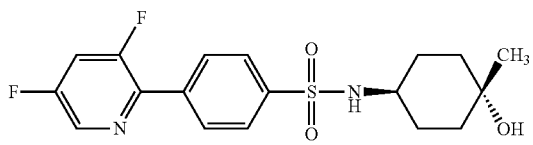

4-(3,5-Difluoropyridin-2-yl)-N-((1r,4r)-4-hydroxy-4-methylcyclohexyl)benzenesulfonamide
(HMC-N-02-A)

A stirred solution of dioxane: water (9:1; 100 mL), N-((1r,4r)-4-hydroxy-4-methylcyclohexyl)-4-(4,4,5,5-tetramethyl-1,3,2-dioxaborolan-2-yl)benzenesulfonamide (20 g, 50.6 mmol), 2-bromo-3,5-difluoropyridine (14.73 g, 75.94 mmol) and sodium carbonate (10.73 g, 101.2 mmol) was degassed using argon for 10 minutes. [1,1-Bis(diphenylphosphino) ferrocene] dichloropalladium(II) (3.7 g, 5.06 mmol) was added and the reaction mixture was degassed for another 10 minutes and stirred at 110° C. for 6 hours. The solvent was evaporated under reduced pressure and the compound was extracted into ethyl acetate. The organic layer was separated, dried over sodium sulfate and concentrated under reduced pressure. The residue was purified by silica gel column chromatography and the fractions were concentrated to minimum volume and then filtered. The residue obtained was washed with 20% ethyl acetate in hexane followed by n-pentane to give the title compound (8 g, 41%).

$^1$H NMR: (400 MHz; methanol-$d_4$) δ 8.54 (d, J=2.0 Hz, 1H), 8.11 (d, J=8.2 Hz, 2H), 7.99 (d, J=8.1 Hz, 2H), 7.74 (m, 1H), 3.20 (m, 1H), 1.83-1.27 (m, 8H), 1.18 (s, 3H).

LCMS: mobile phase A: 10 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 1.75 mins, held at 95:5 B:A for 1 min, reduced linearly to 30:70 B:A over 1.25 min and held at 30:70 B:A for the final 0.5 min. Retention time 1.88 min, m/z 381 (M−H)$^+$.

Synthesis 6

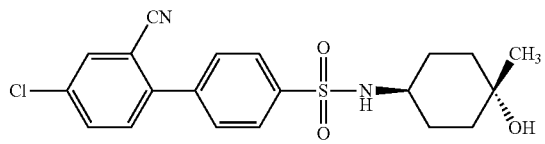

4'-Chloro-2'-cyano-N-((1r,4r)-4-hydroxy-4-methylcyclohexyl)biphenyl-4-sulfonamide
(HMC-C-01-A)

A stirred solution of dioxane: water (9:1; 100 mL), N-((1r,4r)-4-hydroxy-4-methylcyclohexyl)-4-(4,4,5,5-tetramethyl-1,3,2-dioxaborolan-2-yl)benzenesulfonamide (12 g, 30.4 mmol), 2-bromo-5-chlorobenzonitrile (9.86 g, 45.5 mmol) and sodium carbonate (6.44 g, 60.8 mmol) was degassed using argon for 10 minutes. [1,1-Bis(diphenylphosphino)ferrocene] dichloropalladium(II) (2.21 g, 3.0 mmol) was added and the reaction mixture was degassed for another 10 minutes and stirred at 110° C. for 6 hours. The solvent was evaporated under reduced pressure and the compound was extracted into ethyl acetate. The organic layer was separated, dried over sodium sulfate and concentrated under reduced pressure followed by washing with n-pentane (twice) and dried under vacuum at 45-50° C. to give the title compound (5.7 g, 46.5%).

$^1$H NMR (400 MHz, methanol-$d_4$) δ 8.01 (d, J=8.1 Hz, 2H), 7.95 (m, 1H), 7.83-7.74 (m, 3H), 7.64 (d, J=8.5 Hz, 1H), 3.25-3.17 (m, 1H), 1.8-1.54 (m, 4H), 1.47-1.34 (m, 4H), 1.18 (s, 3H).

LCMS: mobile phase A: 10 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2.5 mins, held at 95:5 B:A for 0.5 min, reduced linearly to 30:70 B:A over 1 min and held at 30:70 B:A for the final 0.5 min. Retention time 2.167 min, m/z 403 (M−H)$^+$.

Synthesis 6A

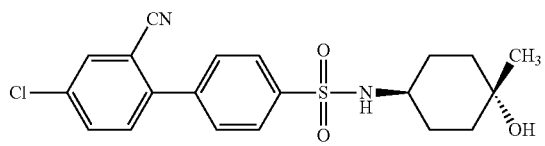

4'-Chloro-2'-cyano-N-((1r,4r)-4-hydroxy-4-methylcyclohexyl)biphenyl-4-sulfonamide
(HMC-C-01-A)

To a 10 L flask was charged finely divided (1r,4r)-4-amino-1-methylcyclohexan-1-ol (123.7 g, 0.957 mol) and dichloromethane (2400 mL). Triethylamine (534 mL, 3.830 mol) was added dropwise. The suspension cooled to below 5° C. and 4-(4-chloro-2-cyanophenyl)benzene-1-sulfonyl chloride (298.9 g, 0.957 mol) in dichloromethane (768 mL) added dropwise maintaining the temperature at less than 25° C. The reaction mixture was allowed to warm to room temperature and stirred for 40 hours. The reaction mixture was cooled to below 10° C. and 2 M aqueous hydrochloric acid (2090 mL) added dropwise while maintaining the temperature at less than 25° C. (exothermic addition and white fumes observed). The phases were separated and the organic layer was washed with water (2090 mL). The organics were dried over anhydrous magnesium sulphate, filtered, and the residue was washed with dichloromethane (2×50 mL). The combined filtrates were then combined with the crude product from a similar smaller scale reaction of 4-(4-chloro-2-cyanophenyl)benzene-1-sulfonyl chloride (50 g) and (1r,4r)-4-amino-1-methylcyclohexan-1-ol, and all of the combined materials adsorbed directly onto silica (800 g). This was purified by chromatography on silica (8000 g) eluting initially with ethyl acetate: dichloromethane 20:80, and then sequentially with mixtures of ethyl acetate: dichloromethane 30:70, 40:60, 50:50, followed by neat ethyl acetate. Fractions containing the product were combined and concentrated to afford a yellow solid. This material was dried in a vacuum oven overnight at 40° C. to afford the title compound (406.8 g; overall 88% yield). Analysis by NMR indicated a purity of >97%.

$^1$H NMR: (270 MHz; CDCl$_3$) δ 8.02 (d, J=8.6 Hz, 2H), 7.78 (d, J=2 Hz, 1H), 7.73-7.63 (m, 3H), 7.49 (d, J=8.5 Hz, 1H), 4.89 (d, J=7 Hz, 1H), 3.38 (m, 1H), 1.98-1.75 (m, 2H), 1.75-1.3 (m, 7H, m), 1.23 (s, 3H).

HPLC: mobile phase A: purified water+0.1% trifluoroacetic acid, mobile phase B: acetonitrile+0.1% trifluoroacetic acid; Column: Fortis C18 4.6×150 mm; 3 uM; Flow rate: 1.0 mL/min. Run time: 30 mins—starting solvent 5:95 B:A is increased linearly to 95:5 B:A over the first 15 mins, held at 95:5 B:A for the final 15 min. Retention time 12.0 min. Mass Spectrum: Bruker Esquire 3000 Plus Ion Trap MS; Positive ion polarity, ESI: m/z 403 (M−H)$^+$.

Synthesis 7

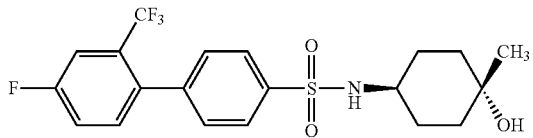

4'-Fluoro-N-((1r,4r)-4-hydroxy-4-methylcyclohexyl)-2'-(trifluoromethyl)biphenyl-4-sulfonamide
(HMC-C-02-A)

A stirred solution of dioxane: water (9:1; 100 mL), N-((1r,4r)-4-hydroxy-4-methylcyclohexyl)-4-(4,4,5,5-tetramethyl-1,3,2-dioxaborolan-2-yl)benzenesulfonamide-yl)benzenesulfonamide (20 g, 50.6 mmol), 1-bromo-4-fluoro-2-(trifluoromethyl)benzene (18.45 g, 75.9 mmol) and sodium carbonate (10.73 g, 101.2 mmol) was degassed using argon for 10 minutes. [1,1-Bis(diphenylphosphino)ferrocene]dichloropalladium(II) (3.7 g, 5.06 mmol) was added and the reaction mixture was degassed for another 10 minutes and stirred at 110° C. for 6 hours. The solvent was evaporated under reduced pressure and the compound was extracted into ethyl acetate. The organic layer was separated, dried over sodium sulfate and concentrated under reduced pressure. The residue was purified by silica gel column chromatography and the fractions were concentrated and then filtered. The residue obtained was washed with a minimal volume of dichloromethane followed by washing with n-pentane (twice) and dried under vacuum at 45-50° C. to give the title compound (10.2 g, 47%).

$^1$H NMR (400 MHz, methanol-d$_4$) δ 7.93 (d, J=7.9 Hz, 2H), 7.59 (d, J=9.2 Hz, 1H), 7.51 (d, J=8.1 Hz, 2H), 7.46 (d, J=6.6 Hz, 2H), 3.20 (m, 1H), 1.79-1.51 (m, 4H), 1.49-1.30 (m, 4H), 1.18 (s, 3H).

LCMS: mobile phase A: 10 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 1.75 mins, held at 95:5 B:A for 1 min, reduced linearly to 30:70 B:A over 1.25 min and held at 30:70 B:A for the final 0.5 min. Retention time 2.16 min, m/z 430 (M−H)$^+$.

Synthesis 8

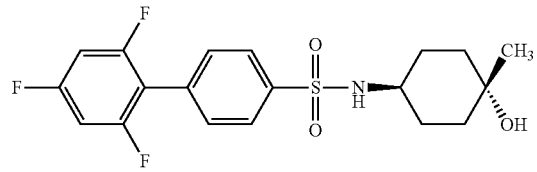

2',4',6'-Trifluoro-N-((1r,4r)-4-hydroxy-4-methylcyclohexyl)biphenyl-4-sulfonamide
(HMC-C-03-A)

A mixture of dioxane: water (3:1; 20 mL) was degassed. 1-Bromo-2,4,6-trifluorobenzene (1.91 g, 9.1 mmol), N-((1r,4r)-4-hydroxy-4-methylcyclohexyl)-4-(4,4,5,5-tetramethyl-1,3,2-dioxaborolan-2-yl)benzenesulfonamide (1.8 g, 4.6 mmol), K$_2$CO$_3$ (1.24 g, 9.0 mmol) and [1,1 Bis(diphenylphosphino)ferrocene]dichloropalladium(II) (257 mg, 0.35 mmol) were added and the reaction mixture stirred at 120° C. in a microwave oven for 3 hours. The reaction mixture was concentrated, diluted with ethyl acetate and washed with water. The organic extracts were dried (MgSO$_4$) and concentrated to give a crude residue which was purified by flash column (eluent: 40 to 50% ethyl acetate in heptane). The product was purified further by crystallisation (ethyl acetate/heptane) to give the title compound (620 mg, 34%).

$^1$H NMR: (400 MHz; CDCl$_3$) δ 7.95 (d, 2H), 7.58 (d, 2H), 6.80 (t, 2H), 4.62-4.52 (m, 1H), 3.41-3.30 (m, 1H), 1.91-1.81 (m, 2H), 1.66-1.34 (m, 6H), 1.22 (s, 3H).

LCMS: mobile phase A: 10 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 5.5 mins—starting solvent 30:70 B:A is increased linearly to 95:5 B:A over the first 2.5 mins, held at 95:5 B:A for 1 min, reduced linearly to 30:70 B:A over 1.5 min and held at 30:70 B:A for the final 0.5 min. Retention time 2.40 min m/z 400 (M+H)$^+$.

Synthesis 9

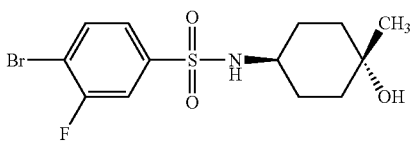

4-Bromo-3-fluoro-N-((1r,4r)-4-hydroxy-4-methylcyclohexyl)benzenesulfonamide

Diisopropylethylamine (20 mL, 116.2 mmol) was added to a solution of (1r,4r)-4-amino-1-methylcyclohexanol (3 g, 23.2 mmol) in dichloromethane (150 mL) and the reaction mixture was cooled to 0° C. 4-Bromo-3-fluorobenzene-1-sulfonyl chloride (6.98 g, 25.5 mmol) was added as solid and the reaction mixture was allowed to stir at room temperature for 4 hours. The reaction mixture was neutralized with 1 M hydrochloric acid and the compound was extracted into dichloromethane. The organic layer was separated, dried over sodium sulfate and concentrated under reduced pressure. The residue obtained was washed with n-pentane, filtered and dried to give the title compound (7 g, 82%). MS (ESI) m/z 368 (M+H)$^+$.

Synthesis 10

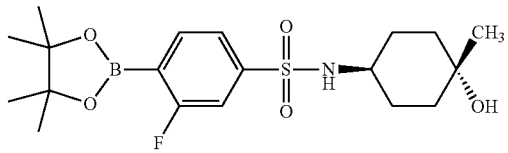

3-Fluoro-N-((1r,4r)-4-hydroxy-4-methylcyclohexyl)-4-(4,4,5,5-tetramethyl-1,3,2-dioxaborolan-2-yl)benzenesulfonamide A stirred solution of toluene (50 mL), 4-bromo-3-fluoro-N-((1r,4r)-4-hydroxy-4-methylcyclohexyl)benzenesulfonamide (9 g, 24.6 mmol), 4,4,4',4',5,5,5',5'-octamethyl-2,2'-bi(1,3,2-dioxaborolane) (9.33 g, 36.7 mmol) and potassium acetate (7.23 g, 73.7 mmol) was degassed using argon for 10 minutes. [1,1-Bis(diphenylphosphino)ferrocene]dichloropalladium(II) (1.8 g, 2.5 mmol) was added and the reaction mixture was degassed for another 10 minutes and stirred at 110° C. for 4 hours. The reaction mixture was cooled to room temperature and filtered through celite. The organic layer was separated, dried over sodium sulfate and concentrated under reduced pressure to give the title compound (10 g, 98%). For large scale batches, the compound was used without further purification. When this preparation was performed on a smaller scale, the residue was taken into ether, filtered and the filtrate was concentrated to give the desired product. MS (ESI) m/z 412 (M−H)$^+$.

Synthesis 11

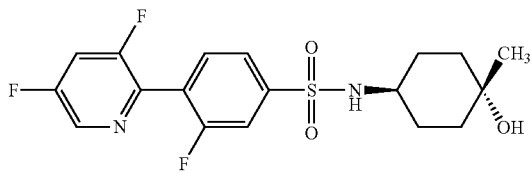

4-(3,5-Difluoropyridin-2-yl)-3-fluoro-N-((1r,4r)-4-hydroxy-4-methylcyclohexyl)benzenesulfonamide
(HMC-N-01-A)

A stirred solution of dioxane (50 mL), 3-fluoro-N-((1r,4r)-4-hydroxy-4-methylcyclohexyl)-4-(4,4,5,5-tetramethyl-1,3,2-dioxaborolan-2-yl)benzenesulfonamide (18 g, 43.6 mmol), 2-bromo-3,5-difluoropyridine (12.68 g, 65.37 mmol) and caesium carbonate (35.52 g, 109.0 mmol) was degassed using argon for 10 minutes. [1,1-Bis(diphenylphosphino) ferrocene]dichloropalladium(II) (3.2 g, 4.4 mmol) was added and the reaction mixture was degassed for another 10 minutes and then stirred at 110° C. for 6 hours. The solvent was evaporated under reduced pressure and the compound was extracted into ethyl acetate. The organic layer was separated, dried over sodium sulfate and concentrated under reduced pressure. The residue was purified by silica gel column chromatography followed by washing with n-pentane to give the title compound (8.19 g, 47%).

$^1$H NMR (400 MHz, methanol-d$_4$) δ 8.55 (d, J=2.1 Hz, 1H), 7.87-7.71 (m, 4H), 3.24 (m, 1H), 1.8-1.7 (m, 2H), 1.66-1.55 (m, 2H), 1.51-1.34 (m, 4H), 1.19 (s, 3H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2.5 mins, held at 95:5 B:A for 0.5 min, reduced linearly to 30:70 B:A over 1 min and held at 30:70 B:A for the final 0.5 min. Retention time 1.88 min, m/z 399 (M−H)$^+$.

Synthesis 12

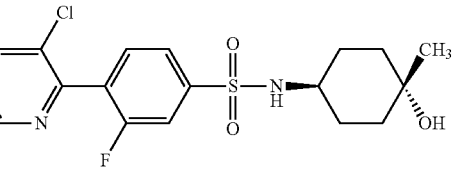

4-(3,5-Dichloropyridin-2-yl)-3-fluoro-N-((1r,4r)-4-hydroxy-4-methylcyclohexyl)benzenesulfonamide
(HMC-N-01-A)

A solution of 3-fluoro-N-((1r,4r)-4-hydroxy-4-methylcyclohexyl)-4-(4,4,5,5-tetramethyl-1,3,2-dioxaborolan-2-yl) benzenesulfonamide (0.338 g, 0.82 mmol) in dimethoxyethane (10 mL) was purged with argon for 15 min. 2-bromo-3,5-dichloropyridine (0.185 g, 0.82 mmol) and sodium carbonate (0.175 g, 1.65 mmol) in water were added and degassed using argon for 30 minutes. [1,1-Bis(diphenylphosphino)ferrocene] dichloropalladium(II) (0.12 g, 0.16 mmol) was added and the reaction mixture was degassed for another 10 minutes and then stirred at 80° C. for 2 hours. The reaction mixture was cooled and filtered through celite. The solvent was evaporated under reduced pressure and the residue was purified by silica gel column chromatography using 50% ethyl acetate in hexane to give the title compound (0.04 g, 11%).

$^1$H NMR (400 MHz, methanol-d$_4$) δ 1.19 (3H, s), 1.33-1.52 (4H, m), 1.54-1.66 (2H, m), 1.69-1.82 (2H, m), 3.25 (1H, m), 7.68 (1H, m), 7.75 (1H, m), 7.82 (1H, m), 8.20 (1H, d, J=2.1 Hz), 8.65 (1H, d, J=2.1 Hz).

LCMS: mobile phase A: 10 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.2 mL/min. Run time: 5 mins—starting solvent 35:65 B:A is increased linearly to 95:5 B:A over the first 2.5 mins, held at 95:5 B:A for 1.3 min, reduced immediately to 35:65 B:A for the final 1.2 min. Retention time 2.59 min m/z 431 (M–H)+.

Synthesis 13

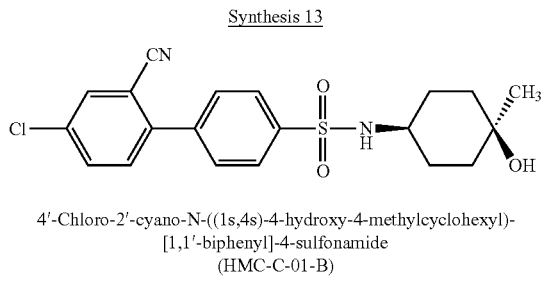 [SMILES: C[C@]1(O)CC[C@@H](NS(=O)(=O)c2ccc(-c3ccc(Cl)cc3C#N)cc2)CC1]

4'-Chloro-2'-cyano-N-((1s,4s)-4-hydroxy-4-methylcyclohexyl)-
[1,1'-biphenyl]-4-sulfonamide
(HMC-C-01-B)

A solution of N-((1s,4s)-4-hydroxy-4-methylcyclohexyl)-4-(4,4,5,5-tetramethyl-1,3,2-dioxaborolan-2-yl)benzenesulfonamide (17 g, 43.0 mmol), 2-bromo-5-chlorobenzonitrile (14 g, 64.7 mmol), and sodium carbonate (9.1 g, 86 mmol) in dioxane: water (240 mL, 9:1) was degassed using argon for 10 min. [1,1-Bis(diphenylphosphino)ferrocene]dichloropalladium(II) (3.14 g, 4.3 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate and concentrated under reduced pressure. The residue was purified by silica gel column chromatography using 100-200 mesh silica gel using 20-40% ethyl acetate in hexane as eluent. The fractions were concentrated to $1/10^{th}$ the volume (85 mL) and then filtered. The residue obtained was washed with 20% ethyl acetate in hexane followed by n-pentane to afford the title compound. Yield: 5.8 g, 33% (over 2 steps).

$^1$H NMR (400 MHz, Chloroform-d) δ 8.04-7.97 (m, 2H), 7.79 (d, J=2.2 Hz, 1H), 7.69-7.64 (m, 3H), 7.48 (d, J=8.4 Hz, 1H), 4.45 (d, J=8 Hz, 1H), 3.3-3.15 (br, 1H), 1.74-1.51 (m, 6H), 1.45-1.35 (m, 2H), 1.20 (s, 3H), 1.00 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.62 min m/z 403.30 [M–1].

Synthesis 14

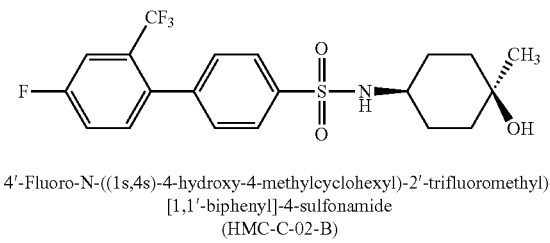

4'-Fluoro-N-((1s,4s)-4-hydroxy-4-methylcyclohexyl)-2'-trifluoromethyl)-
[1,1'-biphenyl]-4-sulfonamide
(HMC-C-02-B)

A solution of N-((1s,4s)-4-hydroxy-4-methylcyclohexyl)-4-(4,4,5,5-tetramethyl-1,3,2-dioxaborolan-2-yl)benzenesulfonamide (13.5 g, 34.1 mmol), 1-bromo-4-fluoro-2-(trifluoromethyl)benzene (12.45 g, 51.2 mmol), and sodium carbonate (7.24 g, 68.3 mmol) in dioxane: water (230 mL, 9:1) was degassed using argon for 10 min. [1,1-Bis(diphenylphosphino)ferrocene] dichloropalladium(II) (2.49 g, 3.4 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate, and concentrated under reduced pressure. The residue was purified by silica gel column chromatography using 100-200 mesh silica gel using 20-40% ethyl acetate in hexane as eluent. The fractions were concentrated to $1/10^{th}$ of the volume (80 mL) and then filtered. The residue obtained was washed with 20% ethyl acetate in hexane followed by n-pentane to afford the title compound. Yield: 5.6 g, 20% (over 2 steps).

$^1$H NMR (400 MHz, Chloroform-d) δ 7.97-7.88 (m, 2H), 7.52-7.40 (m, 3H), 7.31 (dd, J=7.0, 2.4 Hz, 2H), 4.40 (d, J=8.0 Hz, 1H), 3.25-3.12 (br, 1H), 1.70-1.50 (m, 6H), 1.45-1.33 (m, 2H), 1.20 (s, 3H), 1.00 (bs, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.79 min m/z 430 [M–1].

Synthesis 15

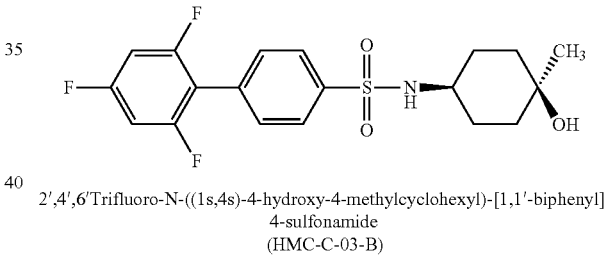

2',4',6'Trifluoro-N-((1s,4s)-4-hydroxy-4-methylcyclohexyl)-[1,1'-biphenyl]-
4-sulfonamide
(HMC-C-03-B)

A solution of N-((1s,4s)-4-hydroxy-4-methylcyclohexyl)-4-(4,4,5,5-tetramethyl-1,3,2-dioxaborolan-2-yl)benzenesulfonamide (15 g, 37.9 mmol), 2-bromo-1,3,5-trifluorobenzene (12 g, 56.9 mmol), and sodium carbonate (8.03 g, 75.8 mmol) in dioxane: water (250 mL, 9:1) was degassed using argon for 10 min. [1,1-Bis(diphenylphosphino)ferrocene] dichloropalladium(II) (2.77 g, 3.8 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate and concentrated under reduced pressure. The residue was purified by silica gel column chromatography using 100-200 mesh silica gel using 20-40% ethyl acetate in hexane as eluent. The fractions were concentrated to $1/10^{th}$ the volume (90 mL) and then filtered. The residue obtained was washed with 20% ethyl acetate in hexane followed by n-pentane to afford the title compound. Yield: 4.98 g, 18% (over 2 steps).

$^1$H NMR (400 MHz, Chloroform-d) δ 7.99-7.92 (m, 2H), 7.61-7.53 (m, 2H), 6.80 (t, J=8.2 Hz, 2H), 4.39 (d, J=7.8 Hz, 1H), 3.25-3.12 (br, 1H), 1.75-1.51 (m, 6H), 1.48-1.33 (m, 2H), 1.20 (s, 3H), 0.99 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.65 min m/z 398 [M−1].

Synthesis 16

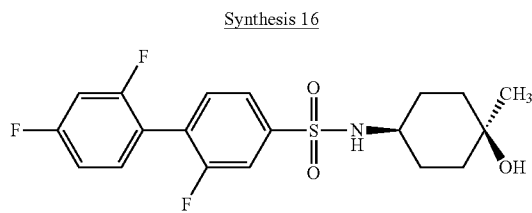

2,2′,4′-Trifluoro-N-((1s,4s)-4-hydroxy-4-methylcyclohexyl)-[1,1′-biphenyl]-4-sulfonamide
(HMC-C-04-B)

A solution of 3-fluoro-N-((1s,4s)-4-hydroxy-4-methylcyclohexyl)-4-(4,4,5,5-tetramethyl-1,3,2-dioxaborolan-2-yl)benzenesulfonamide (3.1 g, 7.5 mmol), 1-bromo-2,4-difluorobenzene (2.1 g, 10.9 mmol), and sodium carbonate (1.6 g, 15.0 mmol) in dioxane:water (60 mL, 5:1) was degassed using argon for 10 min. [1,1-Bis(diphenylphosphino)ferrocene] dichloropalladium(II) (0.548 g, 0.75 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate and concentrated under reduced pressure. The residue was purified by silica gel column chromatography using 100-200 mesh silica gel with 20-40% ethyl acetate in hexane as eluent to afford the title compound. Yield: 0.6 g, 18% (over 2 steps).

$^1$H NMR (400 MHz, Chloroform-d) δ 7.73-7.69 (m, 2H), 7.56-7.47 (m, 1H), 7.44-7.32 (m, 1H), 7.06-6.91 (m, 2H), 4.41 (d, J=7.8 Hz, 1H), 3.27-3.14 (br, 1H), 1.76-1.52 (m, 6H), 1.48-1.35 (m, 2H), 1.21 (s, 3H), 0.97 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.70 min m/z 398 [M−1].

Synthesis 17

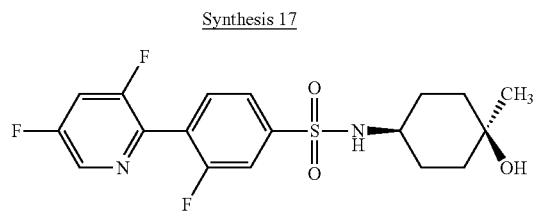

4-(3,5-Difluoropyridin-2-yl)-3-fluoro-N-((1s,4s)-4-hydroxy-4-methylcyclohexyl)-benzenesulfonamide
(HMC-N-01-B)

A solution of 3-fluoro-N-((1s,4s)-4-hydroxy-4-methylcyclohexyl)-4-(4,4,5,5-tetramethyl-1,3,2-dioxaborolan-2-yl) benzenesulfonamide (22 g, 53.2 mmol), 2-bromo-3,5-difluoropyridine (15.5 g, 79.9 mmol), and cesium carbonate (52.0 g, 159.6 mmol) in dioxane: water (100 mL) was degassed using argon for 10 min. [1,1-Bis(diphenylphosphino)ferrocene] dichloropalladium(II) (3.9 g, 5.3 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate and concentrated under reduced pressure. The residue was purified by silica gel column chromatography using 100-200 mesh silica gel using 20-40% ethyl acetate in hexane as eluent. The fractions were concentrated to 1/10$^{th}$ the volume (110 mL) and filtered. The residue obtained was washed with 20% ethyl acetate in hexane followed by n-pentane to afford the title compound. Yield: 5.6 g, 26% (over 2 steps).

$^1$H NMR (400 MHz, Chloroform-d) δ 8.50 (m, 1H), 7.83-7.67 (m, 3H), 7.41-7.33 (m, 1H), 4.43 (d, J=7.8 Hz, 1H), 3.28-3.13 (m, 1H), 1.74-1.52 (m, 6H), 1.46-1.35 (m, 2H), 1.21 (s, 3H), 0.97 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.42 min m/z 399 [M−1].

Synthesis 18

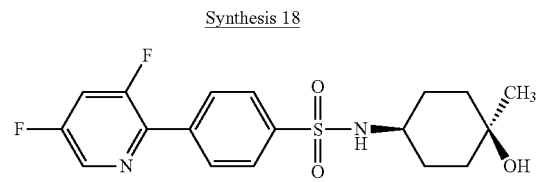

4-(3,5-Difluoropyridin-2-yl)-N-((1s,4s)-4-hydroxy-4-methylcyclohexyl)-benzenesulfonamide
(HMC-N-02-B)

To a stirred solution of N-((1s,4s)-4-hydroxy-4-methylcyclohexyl)-4-(4,4,5,5-tetramethyl-1,3,2-dioxaborolan-2-yl)benzenesulfonamide (26.5 g, 67.0 mmol), 2-bromo-3,5-difluoropyridine (19.5 g, 100.5 mmol), and sodium carbonate (14.22 g, 134.2 mmol) in dioxane: water (250 mL, 9:1) was degassed using argon for 10 min. [1,1-Bis(diphenylphosphino)ferrocene] dichloropalladium(II) (4.90 g, 6.70 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate and concentrated under reduced pressure to obtain a residue. The residue was purified by silica gel column chromatography using 100-200 mesh silica gel using 20-40% ethyl acetate in hexane as eluent. The fractions were concentrated to 1/10$^{th}$ of the volume (100 mL) and then filtered. The residue obtained was washed with 20% ethyl acetate in hexane followed by n-pentane to afford the title compound. Yield: 5.9 g, 26% (over 2 steps).

$^1$H NMR (400 MHz, Chloroform-d) δ 8.48 (d, J=2.4 Hz, 1H), 8.13-8.06 (m, 2H), 7.98 (d, J=8.5 Hz, 2H), 7.39-7.31 (m, 1H), 4.39 (d, J=7.8 Hz, 1H), 3.25-3.1 (br, 1H), 1.72-1.5 (m, 6H), 1.42-1.32 (m, 2H), 1.19 (s, 3H), 0.96 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.41 min m/z 381 [M−1].

Synthesis 19

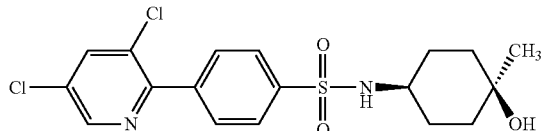

4-(3,5-Dichloropyridin-2-yl)-N-((1s,4s)-4-hydroxy-4-methylcyclohexyl)-benzenesulfonamide
(HMC-N-03-B)

A solution of N-((1s,4s)-4-hydroxy-4-methylcyclohexyl)-4-(4,4,5,5-tetramethyl-1,3,2-dioxaborolan-2-yl)benzenesulfonamide (1.5 g, 3.8 mmol), 2-bromo-3,5-dichloropyridine (1.3 g, 5.7 mmol), and sodium carbonate (0.805 g, 7.6 mmol) in dioxane: water (18 mL, 5:1) was degassed using argon for 10 min. [1,1-Bis(diphenylphosphino)ferrocene] dichloropalladium(II) (0.277 mg, 0.38 mmol) was added and the reaction mixture was degassed for another 10 min. The reaction mixture was heated at 110° C. for 6 hours. A further solution of N-((1s,4s)-4-hydroxy-4-methylcyclohexyl)-4-(4,4,5,5-tetramethyl-1,3,2-dioxaborolan-2-yl)benzenesulfonamide (4 g, 10.1 mmol), 2-bromo-3,5-dichloropyridine (3.44 g, 15.2 mmol), and sodium carbonate (2.14 g, 20.2 mmol) in dioxane:water (54 mL, 5:1) was degassed using argon for 10 min. [1,1-Bis(diphenylphosphino)ferrocene] dichloropalladium(II) (0.739 g, 1.0 mmol) was added and the reaction mixture was degassed for another 10 min. The reaction mixture was heated at 110° C. for 6 hours. Both the above batches were combined. Solvent was evaporated under reduced pressure, water was added, and the compound was extracted in ethyl acetate. The organic layer was separated, dried over sodium sulphate and concentrated under reduced pressure to obtain a residue. The residue was purified by silica gel column chromatography using 100-200 mesh silica gel with 20-40% ethyl acetate in hexane as the eluent. The fractions were concentrated to ¹/₁₀$^{th}$ of the volume (30 mL) and then filtered. The residue obtained was washed with 20% ethyl acetate in hexane followed by n-pentane to afford the title compound. Yield: 0.79 g, 14% (over 2 steps).

$^1$H NMR (400 MHz, Chloroform-d) δ 8.59 (m, 1H), 8.02-7.94 (m, 2H), 7.90-7.83 (m, 3H), 4.47 (d, J=8 Hz, 1H), 3.25-3.1 (br, 1H), 1.73-1.5 (m, 6H), 1.44-1.32 (m, 2H), 1.19 (s, 3H), 1.01 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.69 min m/z 413[M−1].

Synthesis 20

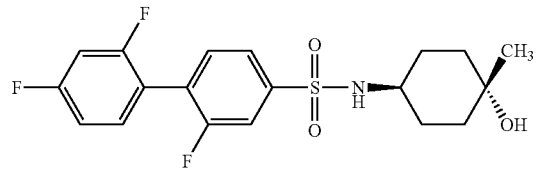

2,2′,4′-Trifluoro-N-((1r,4r)-4-hydroxy-4-methylcyclohexyl)-[1,1′-biphenyl]-4-sulfonamide
(HMC-C-04-A)

A solution of 3-fluoro-N-((1r,4r)-4-hydroxy-4-methylcyclohexyl)-4-(4,4,5,5-tetramethyl-1,3,2-dioxaborolan-2-yl)benzenesulfonamide (3.5 g, 8.4 mmol), 1-bromo-2,4-difluorobenzene (2.44 g, 12.7 mmol), and sodium carbonate (1.79 g, 16.9 mmol) in dioxane: water (60 mL, 5:1) was degassed using argon for 10 min. [1,1-Bis(diphenylphosphino)ferrocene] dichloropalladium(II) (0.619 g, 0.85 mmol) was added and the reaction mixture was degassed for another 10 min. The reaction mixture was heated at 110° C. for 6 hours. Solvent was evaporated under reduced pressure, water was added, and the compound was extracted in ethyl acetate. The organic layer was separated, dried over sodium sulphate, and concentrated under reduced pressure. The residue was purified by SFC purification: Mobile Phase: CO2:Methanol (05-50 in 5 min), Column: Silica 2-Ethylpyridine (250×4.6 mm, 5μ), Flow: 3 mL/min, Wavelength: 210-400 nm to afford the title compound. Yield: 0.7 g, 19% (over 2 steps).

$^1$H NMR (400 MHz, Chloroform-d) δ 7.78-7.64 (m, 2H), 7.62-7.45 (m, 1H), 7.44-7.34 (m, 1H), 7.06-6.91 (m, 2H), 4.51 (d, J=6.8 Hz, 1H), 3.40-3.35 (br, 1H), 1.95-1.83 (m, 2H), 1.67-1.37 (m, 6H), 1.25 (d, J=3.3 Hz, 3H), 1.13 (s, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 4.5 mins—starting solvent 30:70 B:A is increased linearly to 95:5 B:A over the first 2 mins, held at 95:5 B:A for 1.5 min, reduced linearly to 30:70 B:A over 0.5 min and held at 30:70 B:A for the final 0.5 min. Retention time 2.56 min m/z 398 [M−1].

Synthesis 21

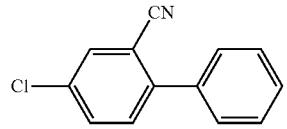

5-Chloro-2-phenylbenzonitrile

2-Bromo-5-chloro-benzonitrile (297.0 g, 1.372 mol), phenyl boronic acid (184.0 g, 1.509 mol), sodium carbonate (436.3 g, 4.116 mol), 1,2-dimethoxyethane (4455 mL) and water (1485 mL) were added to a vessel under nitrogen. The flask was degassed three times with nitrogen and tetrakis(triphenylphosphine)palladium(0) (79.3 g, 0.069 mol) was added. The flask was degassed three times with nitrogen and was stirred and heated to 70° C. and then stirred at that temperature for 24 h. Further phenyl boronic acid (36.8 g, 0.302 mol), sodium carbonate (87.3 g, 0.824 mol) and tetrakis(triphenylphosphine) palladium (15.9 g, 0.014 mol) were added and the mixture stirred for a further 16 h. The reaction was cooled to room temperature and the suspension was filtered and the solid washed with ethyl acetate (2×2000 mL). The combined filtrates were separated and the organic layer was washed with saturated brine (2×2000 mL). The organic layer was dried over anhydrous magnesium sulphate, filtered and the solid washed with ethyl acetate (1000 mL). The combined filtrates were concentrated whilst absorbing onto silica gel (600 g). The crude material was purified on silica gel (6 Kg) eluting with 25-50% toluene in heptane. The pure fractions were combined and concentrated to give a white solid. The solid was azeotroped with heptane (8×800 mL) to remove any residual toluene and give the target compound. Yield=215.9 g (73.6%).

1H NMR (270 MHz, DMSO $d_6$) δ 8.18-8.12 (m, 1H), 7.86 (dd, J=8.4 Hz, 2.4 Hz, 1H), 7.7-7.45 (m, 6H).

Synthesis 22

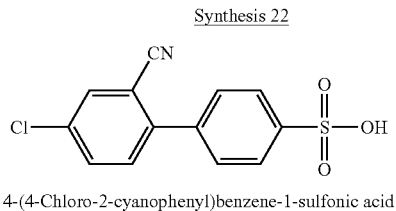 [SMILES: N#Cc1cc(Cl)ccc1-c1ccc(S(=O)(=O)O)cc1]

4-(4-Chloro-2-cyanophenyl)benzene-1-sulfonic acid

To a 5 L flask was charged crude 5-chloro-2-phenylbenzonitrile (407.8 g, 1.909 mol) and chloroform (2325 mL). The pale yellow solution was cooled to less than 5° C. and chlorosulfonic acid (343 mL, 5.15 mol) was added, keeping the temperature at less than 10° C. The reaction mixture was allowed to warm to room temperature and the dark brown solution was stirred at room temperature overnight. The reaction mixture was concentrated at 20° C. and the residue was dissolved in ethyl acetate (2325 mL)-exotherm to 33° C. observed. Water (490 mL) was added (exotherm to 64° C.) followed by saturated brine (1920 mL), and the mixture was cooled to 19° C. The thick suspension was filtered (very slow filtration) and the residue washed with water (2×1 L) and ethyl acetate (2×1.5 L). The filter cake was dried in vacuo at 40° C. for 64 hours to afford 435 g of material as a yellow solid. This was slurried in ethyl acetate (1740 mL) at room temperature for 20 minutes. The suspension was filtered and the residue washed with ethyl acetate (435 mL). The filter cake was dried in vacuo at 40-60° C. over two nights to afford a cream solid (366.3 g), containing 289 g of the title compound (52% yield). Analysis by Karl Fischer showed the product contained 4.3% water.

1H NMR (270 MHz, DMSO $d_6$) δ 8.16 (d, J=2.3 Hz, 1H), 7.85 (dd, J=2.3 Hz, 8.5 Hz, 1H), 7.73 (d, J=8.2 Hz, 2H), 7.65 (d, J=8.2 Hz. 1H), 7.54 (d, J=8.3 Hz, 2H).

Synthesis 23

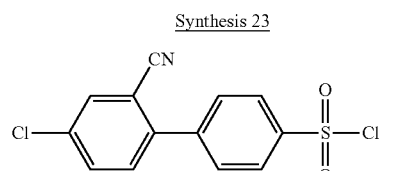

4-(4-Chloro-2-cyanophenyl)benzene-1-sulfonyl chloride

To a 5 L flask was charged crude 4-(4-chloro-2-cyanophenyl)benzene-1-sulfonic acid (366.3 g, containing 289 g 4-(4-chloro-2-cyanophenyl)benzene-1-sulfonic acid, 0.98 mol) and toluene (3000 mL). Thionyl chloride (423 mL, 5.83 mol) was added dropwise followed by dimethylformamide (5 mL, 0.0646 mol). The reaction mixture was heated to 75° C. and stirred overnight. The reaction mixture was cooled, concentrated in vacuo, and the residue was partitioned between ethyl acetate (3000 mL) and water (1500 mL) and the organic layer washed with saturated brine (1500 mL). The organic layer was dried over anhydrous magnesium sulphate (50 g) and filtered. The residue was washed with ethyl acetate (2×100 mL) and the combined organic layers concentrated to afford the title compound (297.6 g, 93% yield) as a yellow solid. Analysis by NMR indicated a purity of 95%.

1H NMR (270 MHz, DMSO $d_6$) δ 8.16 (d, J=2 Hz, 1H), 7.87 (dd, J=2.1 Hz, 8.2 Hz, 1H), 7.73 (d, J=8.2 Hz, 2H), 7.64 (d, J=8.2 Hz. 1H), 7.54 (d, J=8.3 Hz, 2H).

Synthesis 24

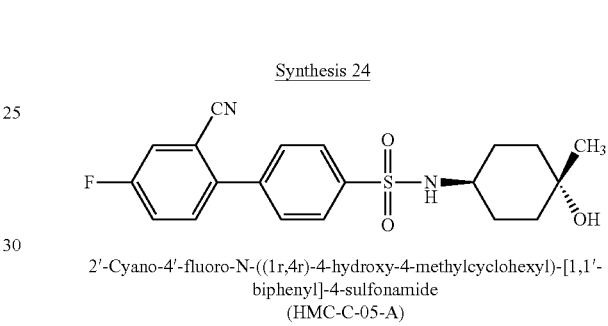

2'-Cyano-4'-fluoro-N-((1r,4r)-4-hydroxy-4-methylcyclohexyl)-[1,1'-biphenyl]-4-sulfonamide
(HMC-C-05-A)

A stirred solution of N-((1r,4r)-4-hydroxy-4-methylcyclohexyl)-4-(4,4,5,5-tetramethyl-1,3,2-dioxaborolan-2-yl)benzenesulfonamide (1.6 g, 4.05 mmol), 2-bromo-5-fluorobenzonitrile (2.03 g, 10.15 mmol), sodium carbonate (1.07 g, 10.1 mmol) in dioxane: water (30:3 mL) was degassed using argon for 10 min. [1,1-Bis(diphenylphosphino)ferrocene] dichloropalladium(II) (0.296 g, 0.405 mmol) was added and the reaction mixture was degassed for another 10 min and stirred at 110° C. for 6 h. Solvent was evaporated under reduced pressure and the compound was extracted in ethyl acetate. The organic layer was separated, dried over sodium sulphate and concentrated under reduced pressure. The residue was purified by silica gel column chromatography. The obtained residue was washed with hexane followed by n-pentane to afford the title compound as a white solid. Yield: 1.1 g, 70%.

1H NMR (400 MHz, Chloroform-d) δ 8.04-7.97 (m, 2H), 7.71-7.64 (m, 2H), 7.55-7.49 (m, 2H), 7.39-7.46 (m, 1H), 4.46 (d, J=6.6 Hz, 1H), 3.45-3.32 (m, 1H), 1.92-1.82 (m, 2H), 1.65-1.35 (m, 6H), 1.23 (s, 3H), 1.11 (brs, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 5 mins—starting solvent 30:70 B:A is increased linearly to 95:5 B:A over the first 2.50 mins, held at 95:5 B:A for 1.5 min, reduced linearly to 30:70 B:A over 0.5 min and held at 30:70 B:A for the final 0.5 min. Retention time 2.50 min (ESI) m/z 387[M−1].

Synthesis 25

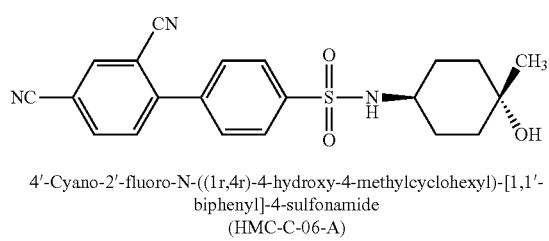

4'-Cyano-2'-fluoro-N-((1r,4r)-4-hydroxy-4-methylcyclohexyl)-[1,1'-biphenyl]-4-sulfonamide
(HMC-C-06-A)

A stirred solution of N-((1r,4r)-4-hydroxy-4-methylcyclohexyl)-4-(4,4,5,5-tetramethyl-1,3,2-dioxaborolan-2-yl)benzenesulfonamide (1.6 g, 4.05 mmol), 4-bromo-3-fluorobenzonitrile (2.03 g, 10.1 mmol), sodium carbonate (1.07 g, 10.1 mmol) in dioxane/water (30/3 mL) was degassed using argon for 10 min. [1,1-Bis(diphenylphosphino)ferrocene]dichloropalladium(II) (0.296 g, 0.405 mmol) was added and the reaction mixture was degassed for another 10 min and stirred at 110° C. for 6 h. Solvent was evaporated under reduced pressure and the compound was extracted in ethyl acetate. The organic layer was separated, dried over sodium sulphate and concentrated under reduced pressure. The residue was purified by flash silica gel column chromatography. The residue obtained was washed with hexane followed by n-pentane to give the title compound as a white solid. Yield: 1.19 g, 75.79%.

$^1$H NMR (400 MHz, Chloroform-d) δ 8.03-7.96 (m, 2H), 7.73-7.66 (m, 2H), 7.62-7.56 (m, 2H), 7.54-7.48 (m, 1H), 4.51 (d, J=6.65 Hz, 1H), 3.42-3.30 (m, 1H), 1.95-1.82 (m, 2H), 1.66-1.55 (m, 2H) 1.53-1.37 (m, 4H), 1.23 (s, 3H), 1.12 (brs, 1H).

LCMS: mobile phase A: 5 mM ammonium formate in water+0.1% ammonia, mobile phase B: acetonitrile+5% mobile phase A+0.1% ammonia; Column: YMC Triart, C18 (50×4.6 mm) 3 uM; Flow rate: 1.4 mL/min. Run time: 5 mins—starting solvent 30:70 B:A is increased linearly to 95:5 B:A over the first 2.50 mins, held at 95:5 B:A for 1.5 min, reduced linearly to 30:70 B:A over 0.5 min and held at 30:70 B:A for the final 0.5 min. Retention time 2.52 min (ESI) m/z 387[M−1].

Additional Compounds

The following compounds were also prepared for use as reference compounds in the biological studies described herein:

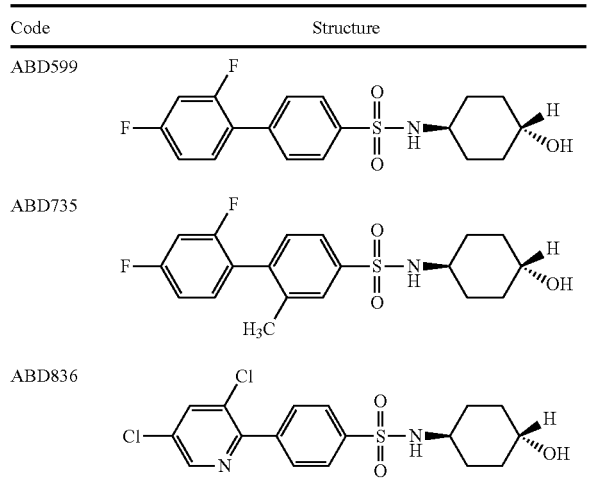

| Code | Structure |
|---|---|
| ABD599 | 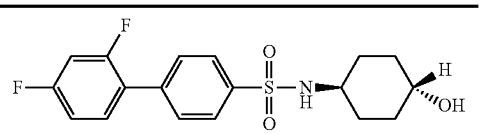 |
| ABD735 | 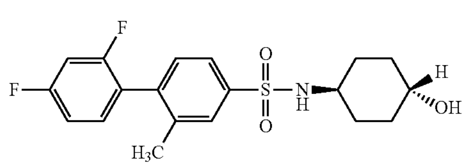 [SMILES: Cc1cc(S(=O)(=O)N[C@H]2CC[C@H](O)CC2)ccc1-c1ccc(F)cc1F] |
| ABD836 | 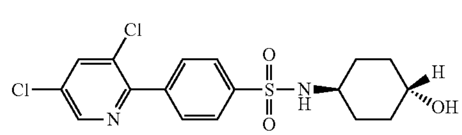 [SMILES: O=S(=O)(N[C@H]1CC[C@H](O)CC1)c1ccc(-c2ncc(Cl)cc2Cl)cc1] |
| ABD899 | |
| ABD900 | |
| REF001 | |

Biological Studies

Potency was assessed using a viability assay based on the survival of the J774 macrophage cell line. Macrophages are closely related to osteoclasts and have been used previously as a model system for osteoclast survival (see, e.g., Luckman et al., 1998, "Heterocycle-containing bisphosphonates cause apoptosis and inhibit bone resorption by preventing protein prenylation: evidence from structure-activity relationships in J774 macrophages," J. Bone Miner. Res., Vol. 13, pp. 1668-1678). The model is indicative both of effects on bone protection in diseases such as osteoporosis, osteoarthritis and rheumatoid arthritis, and of effects on inflammation since, like osteoclasts, J774 macrophages are dependent for survival on continued NFκB activation.

Metabolic stability was measured by determining the rate of disappearance of compound in the presence of human liver microsomal preparations, as quantified by liquid chromatography mass-spectrometry and standard mass-spectrometry (LC-MS/MS).

Solubility was measured by equilibration of the compound in fasted state simulated intestinal fluid (FaSSIF) and quantified by high-performance liquid chromatography (HPLC).

Anti-inflammatory effects were further characterised by assessing the production of interleukin-6 (IL-6) by human Thp-1 derived macrophages stimulated with a pro-inflammatory stimulus bacterial lipopolysaccharide (LPS). LPS acts with a cell-surface receptor, Toll-like receptor-4 to activate the NFκB and IRF signalling pathways to produce IL-6. The reduction of IL- in this stimulated assay is indicative of anti-inflammatory effects with utility in the treatment of conditions in which IL-6 production is aberrant.

In vivo studies were also carried out to evaluate the potential of these compounds as drugs.

Pharmacokinetics were assessed in rats and effects on disease were assessed in a mouse model of collagen-induced arthritis.

Biological Study 1

Resazurin Macrophage J774 Viability Assay

In vitro potency of test compounds was determined by incubation with J774 macrophages and subsequent determination of cell viability using resazurin.

Resazurin is a redox dye commonly used as an indicator of viability in cultured cells (see, e.g., Anoopkumar-Dukie, 2005, British Journal of Radiology, Vol. 78, pp. 945-947). It is non-toxic to cells and stable in culture medium, allowing continuous measurement of cell proliferation in vitro as either a kinetic or endpoint assay. The assay is based on the ability of viable, metabolically-active cells to reduce resazurin (which is blue and non-fluorescent) to resorufin and dihydroresorufin (which are red and fluorescent) using electrons from reducing species, such as nicotinamide adenine dinucleotide (NADPH) and flavin adenine dinucleotide (FADH). This transformation, from oxidised form to reduced form, can be measured either colorimetrically or fluorometrically. Insults that impair cell viability and proliferation also affects the capacity of cells to reduce resazurin, and the rate of dye reduction is directly proportional to the number of viable cells present.

For fluorescence measurements, 530-560 nm excitation and 590 nm emission wavelengths are typically used. For colorimetric measurements, absorbance at 570 nm (reduced form) and 600 nm (oxidised form) is typically measured. A simple calculation is performed to determine the relative quantities of the two species: a high ratio of resorufin (the reduced form) to resazurin (the oxidised form) is an indicator that cells are proliferating and viable. A low ratio indicates cells that are quiescent or non-viable.

J774 cells were plated at $10^4$ cells per well in 100 µL αMEM (α Modified Eagle Medium) in 96-well plates and allowed to adhere overnight. The following day, test compounds were prepared as 100 mM solutions in DMSO. These stock solutions were diluted in DMSO and then diluted 1000× in culture medium (aMEM) before being added directly to the wells so as to give the desired final compound concentration. After a 72 hour incubation at 37° C./5% $CO_2$, resazurin (Alamar Blue, Biosource International) was added to each well (1:10 v/v, 10 µL). The plate was then incubated at 37° C. for 3 hours and fluorescence was measured at 590 nm, with a 25 nm bandwidth.

The average results for each test compound were expressed as a percent (%) of the average control value reflecting cell viability. The average values across the concentrations tested were then plotted and the $IC_{50}$ for was calculated by fitting the data to a 4-parameter $IC_{50}$ equation using software from Grafit (Erithacus Software). Each experiment was repeated twice and the data are presented as the mean $IC_{50}$ from both experiments.

The results are summarised in the following table.

TABLE 1

Resazurin Macrophage J774 Viability Assay

| Compound | $IC_{50}$ (µM) [1] | $IC_{50}$ (µM) [2] |
| --- | --- | --- |
| ABD599 | 0.19 | 0.41 |
| ABD735 | 0.10 | 0.07 |
| ABD836 | 0.28 | 1.45 |
| ABD900 | 0.56 | 3.64 |
| ABD899 | 0.08 | 0.27 |
| REF001 | 0.12 | 0.05 |
| HMC-C-01-A | 0.13 | 1.89 |
| HMC-C-02-A | 0.26 | 14.7 |
| HMC-C-03-A | 0.14 | 0.41 |
| HMC-C-04-A |  | 0.50 |
| HMC-C-05-A |  | 2.46 |
| HMC-C-06-A |  | 0.71 |
| HMC-N-01-A | 0.13 | 2.66 |
| HMC-N-02-A | 0.18 | 4.59 |
| HMC-N-03-A | 0.17 | 0.62 |
| HMC-N-04-A | 0.18 |  |

TABLE 1-continued

Resazurin Macrophage J774 Viability Assay

| Compound | $IC_{50}$ (µM) [1] | $IC_{50}$ (µM) [2] |
| --- | --- | --- |
| HMC-C-01-B |  | 0.16 |
| HMC-C-02-B |  | 1.74 |
| HMC-C-03-B |  | 0.20 |
| HMC-C-04-B |  | 0.06 |
| HMC-N-01-B |  | 0.14 |
| HMC-N-02-B |  | 0.36 |
| HMC-N-03-B |  | 0.08 |

[1] Results from a resazurin macrophage viability assay conducted in a 6 point concentration range from 10 µM to 10 nM with n = 3 replicates per concentration. Data are the mean from 2 independent experiments.
[2] Results from a resazurin macrophage viability assay conducted in a 12 point concentration range from 10 µM to 0.5 nM with n = 4 replicates per concentration. Data are the mean from 3 independent experiments.

These data demonstrate that the HMC compounds described herein, and particularly HMC-C-01-A and HMC-C-01-B; HMC-C-03-A and HMC-C-03-B; HMC-C-04-A and HMC-C-04-B; HMC-C-06-A; HMC-N-01-B; HMC-N-02-B; and HMC-N-03-B show excellent potency in the resazurin macrophage viability assay and no loss of potency, as compared to the reference compounds.

Biological Study 2

Human Liver Microsomal Stability

Metabolic stability of test compounds was measured by determination of the rate of disappearance of the compound when incubated in the presence of human liver microsomes. Liver microsomes are prepared from the endoplasmic reticulum of hepatocytes and are the primary source of the most important enzymes (cytochrome P450s) involved in drug metabolism. Study of drug stability in the presence of liver microsomes is accepted as a valuable model permitting rapid prediction of in vivo drug stability.

Human liver microsomes were obtained from a commercial source. Test compounds (1 µM) were incubated with pooled liver microsomes (male and female). Samples were incubated for a 60 minute period and removed at up to 6 time points and analysed by LC-MS/MS for the presence/amount of test compounds.

Microsomes (final protein concentration 0.25 or 0.5 mg/mL), 0.1 M phosphate buffer pH 7.4, and test compound (final concentration 1 µM; diluted from 10 mM stock solution to give a final DMSO concentration of 0.1%) were incubated at 37° C. prior to the addition of Nicotinamide adenine dinucleotide phosphate (NADPH, final concentration 1 mM) to initiate the reaction. The final incubation volume was 100 µL. A control incubation was included for each compound tested, where 0.1 M phosphate buffer pH 7.4 was added instead of NADPH. The positive control compound terfenadine was included in each experiment and all incubations were performed once for each compound.

Each compound was incubated for 0, 5, 15, 30, 45 or 60 minutes. The reactions were stopped by the addition of 100 µL ice-cold acetonitrile containing internal standard (0.001 mM glipizide) at the appropriate time points. The incubation plates were centrifuged at 4000 rpm for 15 minutes at 4° C. to precipitate the protein and 0.1 mL aliquots were analysed using LC-MS/MS, with the conditions shown in the following table.

TABLE 2

LC-MS/MS Conditions

| | |
|---|---|
| HPLC: | Schimadzu Agilent |
| MS/MS: | API 4000, API 4000 Q-Trap |
| Software: | Analyst 1.5 |
| Ionisation mode: | Turbo spray, positive mode ionisation |
| Scan mode: | Multiple reaction monitoring (MRM) |
| Column: | Waters, Xterra, MS-C18 (2) 5 μm 50 × 3.0 mm |
| Column Temperature (° C.): | 40 |
| Phase A: | 0.1% formic acid in water |
| Phase B: | 0.1% formic acid in acetonitrile |
| Standard Injections (μL): | 1, 2, 3, 5, 7, 10 |
| Test Injections (μL): | 1, 2, 3, 10, 20, 50 |
| Flow Rate (mL/min): | 0.8-1 |

From a plot of the natural logarithm of the peak area ratio (i.e., the ratio of compound peak area: internal standard peak area) against time, the gradient of the line was determined. Subsequently, half-life ($t_{1/2}$) and intrinsic clearance ($CL_{int}$) were calculated using the following equations, where V=Incubation Volume (μL/mg microsomal protein):

Eliminated Rate Constant($k$)=(−Gradient)

Half-Life($t_{1/2}$)(min)=0.063/$k$

Intrinsic Clearance($CL_{int}$)(μL/min/million cells)=($V\times$ 0.693)/$t_{1/2}$ The data are summarised in the following table.

TABLE 3

Human Liver Microsomal Stability

| Compound | $T_{1/2}$ (min) [1] | $T_{1/2}$ (min) [2] |
|---|---|---|
| ABD599 | 287 | |
| ABD735 | 524 | |
| ABD836 | >900 | |
| ABD899 | 72 | 105 |
| ABD900 | | 87 |
| REF001 | 43 | |
| HMC-C-01-A | 82 | |
| HMC-C-02-A | 55 | |
| HMC-C-03-A | 84 | |
| HMC-C-04-A | | 100 |
| HMC-C-05-A | | 123 |
| HMC-C-06-A | | 240 |
| HMC-N-01-A | 175 | |
| HMC-N-02-A | 367 | |
| HMC-N-03-A | 258 | |
| HMC-N-04-A | 156 | |
| HMC-C-01-B | | 70 |
| HMC-C-02-B | | 18 |
| HMC-C-03-B | | 48 |
| HMC-C-04-B | | 107 |
| HMC-N-01-B | | 127 |
| HMC-N-02-B | | 168 |
| HMC-N-03-B | | 70 |

[1] Compounds were incubated with human liver microsomes at a final protein concentration of 0.25 mg/mL with sampling at 5 time points: 0, 5, 15, 30, and 60 minutes. One replicate was performed per time point.
[2] Compounds were incubated with human liver microsomes at a final protein concentration of 0.5 mg/mL with sampling at 6 time points: 0, 5, 15, 30, 45 and 60 minutes. Two replicates were performed per time point.

The data demonstrate that the HMC compounds described herein show metabolic stability equivalent to that of the reference compounds.

Biological Study 3

Aqueous Solubility

Aqueous solubility was measured by equilibration of compounds with fasted state simulated intestinal fluid (FaSSIF) and quantified spectrophotometrically.

FaSSIF was prepared as described below:

Preparation of blank FaSSIF: 0.21 g of sodium hydroxide (NaOH) pellets, 1.97 g of dihydrogen sodium phosphate ($NaH_2PO_4 \cdot 2H_2O$) and 3.09 g of sodium chloride (NaCl) were dissolved in 400 mL of deionised water. The pH was adjusted to 6.5 using 1 M hydrochloric acid and further deionised water added to a final volume of 500 mL.

Preparation of FaSSIF: 0.056 g of SIF Powder (containing sodium taurocholate and lecithin) (Phares AG) was dissolved in 25 mL of blank FaSSIF and stirred until the powder was completely dissolved. The solution was allowed to stand for 2 hours during which it became opalescent; it was used within 24 hours. The final solution composition was characterised as follows:

Sodium taurocholate: 3 mM
Lecithin: 0.75 mM
Osmolarity: 270±10 mOsmol
pH: 6.5

Aqueous solubility was determined by spiking a known concentration of test compound (dissolved in DMSO) into FaSSIF followed by incubation for 16 hours. The optical density was measured at the end of the incubation period for test compounds and a reference used to determine solubility. In brief, two samples were prepared for each determination: a reference sample consisting of a stock solution of test compound in DMSO diluted in system solution (a phosphate free, low absorption buffer) and propanol; and a test sample (prepared in triplicate) consisting of 0.5 mL FaSSIF spiked with test compound at 0.2 mM. Each sample was incubated at room temperature for 16 hours with constant shaking at 250 rpm. At the end of the incubation period, 0.3 mL of each sample was filtered through a pION filter plate (PION, Woburn Mass.), diluted 1:1 with propanol and scanned using UV spectrophotometry at $\lambda_{max}$ (190-400 nM) using a Spectra Max Plus-Version 2.1000 (Molecular Devices, Sunnyvale, Calif.), with μSOL Explorer solubility determination software (pION, Woburn, Mass.).

FaSSIF solubility was calculated using the following formula:

*FaSSIF* Solubility, $$\frac{mg}{mL} = \frac{\left[\frac{150}{75}\right] * \left[\frac{OD \text{ of sample}}{OD \text{ of reference}}\right] * Cr * \text{molecular weight}}{10^6}$$

wherein:

"OD" is the optical density;
"Cr" is the concentration of the reference (33.4 μM); and
"molecular weight" is for the test compound (e.g., 381.44 for ABD735).

The data are summarised in the following table.

TABLE 4

FaSSIF Solubility

| Compound | Solubility (mg/mL) [1] | Solubility (mg/mL) [2] |
|---|---|---|
| ABD599 | 0.03 | |
| ABD735 | 0.02 | |
| ABD836 | 0.03 | |
| ABD899 | 0.06 | 0.13 |
| ABD900 | | 0.12 |
| REF001 | 0.05 | |
| HMC-C-01-A | 0.06 | |
| HMC-C-02-A | 0.04 | |

TABLE 4-continued

FaSSIF Solubility

| Compound | Solubility (mg/mL) [1] | Solubility (mg/mL) [2] |
|---|---|---|
| HMC-C-03-A | 0.03 | |
| HMC-C-04-A | | 0.08 |
| HMC-C-05-A | | 0.19 |
| HMC-C-06-A | | 0.11 |
| HMC-N-01-A | 0.03 | |
| HMC-N-02-A | 0.02 | |
| HMC-N-03-A | >0.08 | |
| HMC-N-04-A | 0.06 | |
| HMC-C-01-B | | 0.08 |
| HMC-C-02-B | | 0.07 |
| HMC-C-03-B | | 0.15 |
| HMC-C-04-B | | 0.13 |
| HMC-N-01-B | | 0.12 |
| HMC-N-02-B | | 0.12 |
| HMC-N-03-B | | 0.10 |

[1] Three replicates were run per study at pH 6.5.
[2] Two replicates were run per study at pH 6.8.

The data demonstrate that the HMC compounds described herein show solubility equivalent to that of the reference compounds.

Biological Study 4

Thp1 Macrophage IL-6 Release Assay

In vitro potency of test compounds in human cells was determined by incubation with Thp1 macrophages and subsequent stimulation with an inflammatory stimulus (bacterial lipopolysaccharide (LPS)) followed by measurement of cellular interleukin-6 (IL-6) release.

The assay is strongly indicative of effects on inflammation. LPS is a ligand for Toll-like receptor-4 (TLR4), which is a member of the Toll-like receptor family of cell surface receptors. This receptor is important in the activation of the innate immune system, the major functions of which are to:
  (a) recruit immune cells to sites of infection through the production of cytokines such as IL-6;
  (b) activate the complement cascade, to identify bacteria, activate cells and clear both dead cells and antibody complexes;
  (c) activate the removal of foreign substances by cells such as macrophages and dendritic cells; and
  (d) activate antigen presentation, part of the adaptive immune system.

TLR4 exerts its effects by activating a signalling cascade that results in the activation of several transcription factors including NFκB and members 3, 5, and 7 of the interferon regulatory transcription factor (IRF) family (IRF-3, IRF-5, and IRF-7). The activation of these transcription factors, and particularly NFκB and IRF-5 drives the synthesis and secretion of cytokines such as interleukin 6 (IL-6).

Over-production/expression of IL-6 is associated with a range of disorders, including autoimmunity, inflammatory and cancer. IL-6 is predominantly synthesised by macrophages and T-cells and is heavily involved in governing the transition from acute to chronic inflammation. It does this by modifying the composition of the white blood cell infiltrate in the inflammatory space, moving it from neutrophils to monocyte/macrophages (see, e.g., Gabay, 2006). In addition, IL-6 exerts stimulatory effects on T- and B-cells (thus favouring chronic inflammatory responses) as well as on osteoclasts (thus promoting the turnover of bone). These effects are involved in the pathology of several diseases including osteoporosis, rheumatoid arthritis, diabetes, atherosclerosis, depression, Alzheimer's disease, systemic lupus erythematosus, Behçet's disease, multiple myeloma, and prostate cancer. Furthermore, patients with advanced or metastatic cancer have higher than normal circulating levels of IL-6. Decreasing IL-6 levels in macrophages is therefore therapeutically beneficial.

Thp1 cells were plated at a concentration of 1×10⁵ cells/well or 1.7×10⁵ cells/well in 500 μL or 150 μL RPMI complete media containing 1% penicillin-streptomycin and 10% heat inactivated foetal bovine serum in 24-well plates or 96-well plates, respectively and allowed to adhere overnight. The following day, the cells were stimulated with phorbol myristic acid (PMA) at a final concentration of 100 nM (24-well plates) or 200 nM (96-well plates) to induce differentiation and maintained for up to 8 days with a medium change at 5 days if cells were cultured to 8 days. Test compounds were prepared as 100 nM solutions in DMSO and then serially diluted in DMSO prior to dilution in culture medium. The diluted compounds were added to the cultures 1 hour prior to stimulation with 100 ng/mL LPS. Following a 16 or 18 hour incubation at 37° C./5% CO$_2$, the cell culture medium was collected and assayed for human IL-6 levels using the human IL-6 duo-set ELISA kit (R&D Systems). The average results for each test compound (n=3) were expressed as a percent (%) of the average control value. The average values across the concentrations tested were then plotted and the IC$_{50}$ for the inhibition of IL-6 was calculated by fitting the data to a 4-parameter IC$_{50}$ equation using software from Grafit version 6.0.12 (Erithacus Software Ltd., by Dr Robin Leatherbarrow) or GraphPad Prism version 5.04 for Windows (GraphPad Software, La Jolla, Calif., USA, www.araphpad.com). Each experiment was repeated twice and the data are presented as the mean IC$_{50}$ from both experiments.

The results are summarised in the following table.

TABLE 5

Macrophage IL-6 Release Assay Data

| Compound | IC$_{50}$ (μM) [1] | IC$_{50}$ (μM) [2] |
|---|---|---|
| ABD599 | | 0.07 |
| ABD899 | | 0.03 |
| ABD900 | | 0.09 |
| HMC-C-01-A | 0.04 | 0.18 |
| HMC-C-02-A | 0.001 | 0.97 |
| HMC-C-03-A | 0.004 | 0.05 |
| HMC-C-04-A | | 0.13 |
| HMC-C-05-A | | 1.02 |
| HMC-C-06-A | | 0.19 |
| HMC-N-01-A | 0.13 | 0.28 |
| HMC-N-02-A | 0.15 | 0.29 |
| HMC-N-03-A | 0.05 | |
| HMC-C-01-B | | 0.06 |
| HMC-C-02-B | | 0.29 |
| HMC-C-03-B | | 0.02 |
| HMC-C-04-B | | 0.03 |
| HMC-N-01-B | | 0.03 |
| HMC-N-02-B | | 0.02 |
| HMC-N-03-B | | 0.02 |

[1] Thp1 cells were plated at a concentration of 1 × 10⁵ cells/well in 500 μL RPMI complete media containing 1% penicillin-streptomycin and 10% heat inactivated foetal bovine serum in 24-well plates for 8 days with a medium change at 5 days. Compounds were tested in triplicate in a 6 point concentration response curve at concentrations of 10, 1, 0.1, 0.01, 0.001 and 0.0001 μM, with IL6 levels measured 16 hours after LPS stimulation. IC$_{50}$'s were calculated using Grafit version 6.0.12 (Erithacus Software).
[2] Thp1 cells were plated at a concentration of 1.7 × 10⁵ cells/well in 150 μL RPMI complete media containing 1% penicillin-streptomycin and 10% heat inactivated foetal bovine serum in 96-well plates for 3 days. Compounds were tested in triplicate in a 9 point concentration response curve at concentrations of 30, 10, 3, 1, 0.3, 0.1, 0.03, 0.01 and 0.001 μM with IL6 levels measured 18 hours after LPS stimulation. IC$_{50}$'s were calculated using GraphPad Prism version 5.04 for Windows (GraphPad Software).

These data demonstrate that the HMC compounds described herein show excellent potency in inhibiting IL-6 release from human macrophages, indicating their utility in the treatment of disorders in which IL-6 is up-regulated. Compounds HMC-C-01-A, HMC-C-03-A, HMC-C-06-A, HMC-C-01-B, HMC-C-03-B, HMC-C-04-B, HMC-N-01-B, HMC-N-02-B and HMC-N-03-B show particularly good activity in reducing IL-6 release.

Biological Study 5

Rodent Pharmacokinetics Studies

Absorption and metabolic stability were studied using an in vivo pharmacokinetics assay.

Three male Sprague-Dawley rats, aged 8-12 weeks, were dosed with test compounds administered either orally or intravenously (dose level of 1 mg/kg body weight intravenous or 5 mg/kg body weight orally). Test compounds were formulated in 0.5% carboxymethylcellulose (CMC)/0.1% Tween-80 for administration via the oral route, or in 5% DMSO/10% solutol in saline for administration via the intravenous route. For compound HMC-C-01-A the oral administration was formulated in 2% dimethylacetamide/20% hydroxypropyl-β-cyclodextrin in water. Animals were given free access to food throughout the study except for fasting overnight and until 2 hours post dose on the day of dosing.

Blood samples were taken from the retro-orbital plexus at the following time points and placed in microtubes containing 20% $K_2EDTA$ solution:

Oral Dosing: predose; 0.25, 0.5, 1, 2, 4, 6, 8, and 24 hours post dose.

Intravenous Dosing: predose; 0.08, 0.25, 0.5, 1, 2, 4, 8, and 24 hours post dose.

Blood samples were centrifuged to obtain plasma, which was transferred to a separate container and frozen at −20° C.

For analysis, samples were thawed at room temperature and prepared by protein precipitation with acetonitrile spiked with internal standard (500 ng/mL glipizide) in the ratio 1:4 with plasma. The samples were then vortexed for 5 minutes and centrifuged for 10 minutes at 20,600× g at 4° C. 100 μL of the supernatant was collected for analysis.

The standard samples were prepared similarly, after spiking blank rat plasma samples with 10 μL of analyte.

The concentration of test compound in rat plasma samples was determined using LC-MS/MS, with the conditions shown in the following table.

TABLE 6

LC-MS/MS Conditions

| | |
|---|---|
| HPLC: | Schimadzu Agilent |
| MS/MS: | API 4000 |
| Software: | Analyst 1.5 |
| Ionisation mode: | Turbo spray, negative mode |
| Scan mode: | Multiple reaction monitoring (MRM) |
| Column | Waters, Xterra, MS-C18 (2) 5 μm 50 × 3.0 mm; Discovery Grace Smart RP183μ, 150 × 2.1, 3 μM; Waters Symmetry Shelf C18 75 × 4.6, 3.5 μM; Agilent Zorbax XDB, 150 × 4.6, 5 μM |
| Column Temperature (° C.): | 40 |
| Phase A: | Acetonitrile |
| Phase B: | 0.1% formic acid |
| Flow Rate (mL/min): | 0.8-1.2 |

The pharmacokinetic parameters for the test compounds were calculated by Phoenix WinNonlin version 6.3 (Pharsight Corp, CA) using standard non-compartmental methods. Peak plasma concentrations ($C_{max}$) and time of the peak plasma concentration ($T_{max}$) were the observed values. The area under the plasma concentration-time curve (AUC) was determined by use of the linear trapezoidal rule up to the last measurable concentration ($AUC_{last}$) and thereafter by extrapolation of the terminal elimination phase to infinity ($AUC_{inf}$). The terminal elimination rate constant ($k_{el}$) was determined by regression analysis of the linear terminal portion of the log plasma concentration-time curve. The elimination phase half-life ($t_{1/2}$) was calculated as $0.693/k_{el}$. The tentative oral bioavailability (F) was calculated by dividing the AUC (0-24 hours) after oral administration by the adjusted AUC (0-8 hours) after intravenous administration (i.e., F=AUC (p.o.)×Dose (i.v.)/AUC (i.v.)×Dose (p.o.)) and reported as a percentage (%).

The pharmacokinetic data are summarised in the following table.

TABLE 7

Pharmacokinetic data

| Compound | Bioavail, F (%) | i.v. AUC (ng/mL/min) | p.o. AUC (ng/mL/min) | $T_{1/2}$ (h) |
|---|---|---|---|---|
| ABD735 | 83 | 1081 | 8965 ‡ | 3.8 |
| ABD836 | 55 | 2142 | 5927 | 5.3 |
| ABD899 | 50 | 2133 | 10740 ‡ | 10.8 |
| REF001 | 50 | 963 | 4766 ‡ | 7.2 |
| HMC-C-01-A | 89 | 900 | 4002 | 6.2 |
| HMC-C-02-A | 39 | 546 | 1069 | 3.2 |
| HMC-C-03-A | 55 | 1427 | 3910 | 2.4 |
| HMC-N-01-A | 64 | 740 | 1408 | 13.4 |
| HMC-N-02-A | 43 | 3053 † | 3303 | 6.3 |
| HMC-N-03-A | 8 | 5102 † | 962 | 3.1 |
| HMC-N-04-A | 66 | 1279 | 4203 | 2.9 |
| HMC-C-01-B | 67 | 1539 | 5121 | 5.7 |
| HMC-C-03-B | 116 | 816 * | 9432 | 8.3 |
| HMN-C-04-B | 59 | 1589 * | 9360 | 5.5 |
| HMC-N-01-B | 60 | 2824 | 8454 | 9.1 |
| HMC-N-02-B | 66 | 1931 | 6412 | 6.0 |
| HMC-N-03-B | 84 | 1380 * | 11609 | 7.4 |

† Dosed at 2 mg/kg intravenously.
* Dosed at 0.5 mg/kg intravenously.
‡ Dosed at 10 mg/kg orally.

These data demonstrate that the HMC compounds described herein have excellent oral pharmacokinetic properties equivalent to those of the reference compounds. This makes them suitable for use as oral drugs.

Biological Study 6

Mouse Collagen-Induced Arthritis

Seven- to eight-week-old male DBA/1j mice were used for all procedures. Animals were housed in groups of 10, and were maintained at 21° C.±2° C. on a 12-hour light/dark cycle with food and water ad libitum. Complete Freund's adjuvant (CFA) was prepared by emulsifying bovine type II collagen at 4 mg/mL with a 4 mg/mL suspension of *Mycobacterium tuberculosis* H37Ra in Incomplete Freund's adjuvant (IFA) (0.85 mL paraffin oil and 0.15 mL mannide monooleate) in a 1:1 (v/v) ratio. All mice were immunised subcutaneously with 200 μg of bovine type II collagen in CFA. 21 days later, all mice were immunised subcutaneously with 100 μg of bovine type II collagen in IFA.

The mice started to develop signs and symptoms of arthritis following the 'booster' immunisation.

For macroscopic assessment of arthritis, the following signs were monitored in each paw of each mouse three times per week and summed to generate the Arthritic Index (AI) (the maximum AI for one animal is 16):

0=no visible effects of arthritis.
1=oedema and/or erythema of 1 digit.
2=oedema and/or erythema of 2 digits.
3=oedema and/or erythema of more than 2 digits.
4=severe arthritis of entire paw and digits.

Animals were sorted into treatment groups with a mean arthritic index of 2.5 and then dosed once daily for 14 days with compound by oral gavage for test compounds, or by subcutaneous injection at a dose of 10 mg/kg for the positive control, etanercept. After completion of the experiment, the mice were sacrificed.

The data were analysed by generating an average of the arthritic index across each treatment group. The mean arthritic index was then compared to the arthritic index of control (untreated) animals using the following formula to generate a percentage inhibition of disease.

$$\% \text{ inhibition of disease} = 100 - \left[\frac{\text{average arthritic index: treated animals}}{\text{average arthritic index: untreated animals}} * 100\right]$$

The data summarised in the following table.

TABLE 8

Inhibition of Arthritis

| Compound | Dose (mg/kg/day) | % inhibition of disease |
|---|---|---|
| ABD735 | 10 | 44 |
| ABD899 | 10 | 77 |
| HMC-C-01-A | 10 | 40 |
| HMC-C-01-A | 3 | 60 |
| HMC-C-01-A | 1 | 50 |
| HMC-C-01-A | 0.3 | 60 |
| HMC-N-01-A | 10 | 45 |
| HMC-C-02-A | 10 | 61 |
| HMC-N-02-A | 10 | 36 |
| HMC-C-01-B | 10 | 26 |
| HMC-N-01-B | 10 → 1 (*) | 38 |

(*) Reduced from 10 to 1 mg/kg/day due to mortality.

Figure 2:
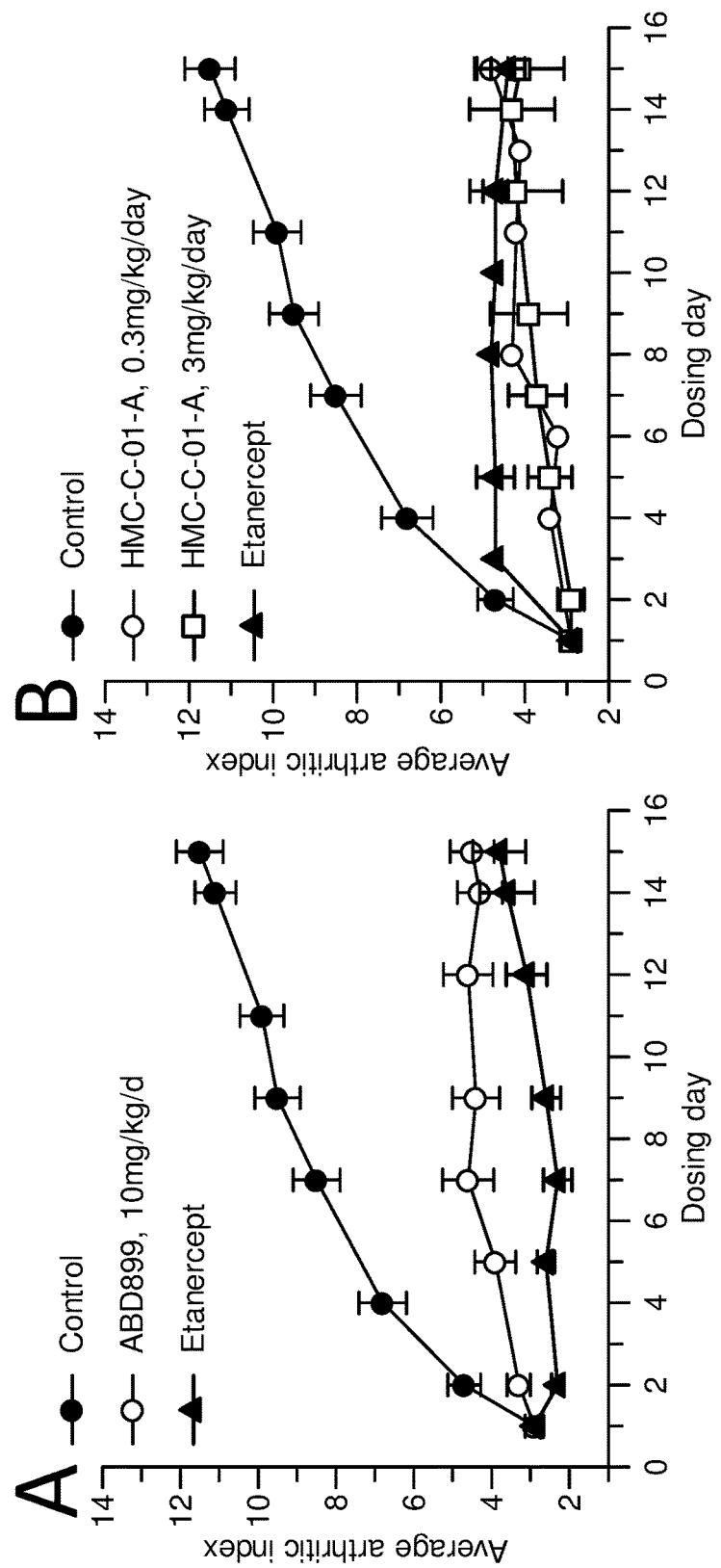
FIG. 2 shows two graphs, each of arthritic index as a function of time (dosing day) for test compound (open circles, open squares), control (solid circles) and positive control, the marketed drug etanercept (triangles), for each of (A) ABD899 at 10 mg/kg/day (left), (B) HMC-C-01-A at 0.3 mg/kg/day and 3 mg/kg/day (right), as described in Biological Study 6 below.

The data for several of the compounds are also illustrated in FIGS. 1 and 2.

FIG. 1 shows six graphs, each of average arthritic index as a function of time (dosing day) for test compound dosed at 10 mg/kg/day by oral gavage (open circles) and control (solid circles), for each of: (A) HMC-C-02-A (top left), (B) HMC-C-01-A (top middle), (C) HMC-N-02-A (top right), (D) HMC-N-01-A (bottom left), (E) HMC-C-01-B (bottom middle), (F) HMC-N-01-B (bottom right).

FIG. 2 shows two graphs, each of arthritic index as a function of time (dosing day) for test compound (open circles, open squares), control (solid circles) and positive control, the marketed drug etanercept (triangles), for each of (A) ABD899 at 10 mg/kg/day (left), (B) HMC-C-01-A at 0.3 mg/kg/day and 3 mg/kg/day (right).

These data indicate that the HMC compounds described herein show excellent oral in vivo activity in preventing the progression of established, severe arthritis.

Furthermore, the data show the exceptional activity of compound HMC-C-01-A, which shows greater efficacy than the marketed treatment, etanercept, at low doses. This activity is particularly surprising since HMC-C-01-A is not the most active compound in either Biological Study 1 or Biological Study 4. Additionally, the activity of HMC-C-01-A is greater than that of the closely related compound, HMC-C-01-B, which is more active than HMC-C-01-A in Biological Studies 1 and 4, showing that demonstrating that the identification of compounds with superior efficacy is neither trivial nor predictable.

Biological Study 7

Maximum Tolerated Dose

The acute safety of the compounds was assessed in rats in order to enable determination of the maximum tolerated dose (MTD), an indication of a compound's safety in animals. The higher the MTD, the greater is the potential safety of the compound being tested.

Two male and two female Sprague-Dawley rats, aged 8-12 weeks, were dosed at each dose level in an ascending dose study design. The test compounds were administered orally as a suspension formulated in 0.5% carboxymethylcellulose (CMC)/0.1% Tween-80 in a dose volume of 10 mL/kg. Animals were given free access to food throughout the study.

Animals were observed on at least two occasions during the first hour following dosing, approximately 30 minutes apart, and thereafter at hourly intervals for the remainder of the dosing day for at least 4 hours. On subsequent days, the animals were observed at least once in the morning and once towards the end of the day. The nature and severity, where appropriate, of the clinical signs and time were recorded at each observation. Observations included changes in the skin, fur, eyes, and mucous membranes, and also the respiratory, circulatory, autonomic, and central nervous system, as well as somatomotor activity and behaviour pattern. Particular attention was directed towards the observation of tremors, convulsions, salivation, diarrhea, lethargy, sleep, and coma.

At the completion of the study, the results were expressed as the maximum tolerated dose for each compound, this being the highest of each without unacceptable toxicity.

The maximum dose without unacceptable side-effects was determined to be the MTD (expressed in mg/kg).

The data are summarised in the following table.

TABLE 9

Maximum Tolerated Dose

| Compound | Maximum tolerated dose (mg/kg) | |
|---|---|---|
| | Females | Males |
| ABD735 | 20 | 10 |
| ABD899 | 30 | 30 |
| REF001 | 7.5 | 10 |
| HMC-C-03-A | 30 | 30 |
| HMC-N-03-A | 50 | 50 |
| HMC-C-01-A [1] | 70 | 70 |
| HMC-C-01-A [2] | >500 | >500 |
| HMC-N-01-A | 80 | 80 |
| HMC-C-02-A | >200 | >200 |
| HMC-N-02-A | >200 | >200 |

[1] Dosed to Sprague Dawley rats as described.
[2] Dosed to Han Wistar rats.

These data demonstrate that the HMC compounds described herein show greatly increased safety as compared to the reference compounds ABD735, ABD899 and REF001.

The data also demonstrate that the improvement of acute safety is neither trivial nor predictable and that similar substitution patterns, for example those found in REF001 can lead to a decrease in acute safety. Furthermore, the data show the exceptional safety of compounds HMC-C-01A, HMC-C-02-A, HMC-N-01-A, and HMC-N-02-A, and particularly of HMC-C-01-A.

The increases in the maximum tolerated dose seen with the HMC compounds described herein provide for an improved safety margin as compared to the reference compounds and underline the potential of the HMC compounds as oral drugs.

Biological Study 8

GreenScreen HC Genotoxicity and Cytotoxicity Assay

GreenScreen HC is a mammalian cell-based assay for measuring the genotoxicity and cytotoxicity of chemical compounds and mixtures.

The term genotoxic is used to describe substances that are capable of causing damage to genetic material (DNA) within a cell, which may ultimately have mutagenic, carcinogenic or teratogenic effects in humans.

The GreenScreen assay reports genotoxic stress as an increase in fluorescence from a genetically modified derivative of the p53-competent TK6 human lymphoblastoid cell line. In the modified cells, regulatory DNA sequences which promote the transcription of the GADD45a gene control the expression of Green Fluorescent Protein (GFP). GADD45a has a central role in genomic integrity, and genotoxic stress induces its transcription. Exposure to a genotoxic compound therefore increases the expression of GFP, which is observed as an increase in fluorescence and which is monitored by fluorescent detection using a plate reader or flow cytometer. In the GreenScreen HC assay fluorescence is normalised to the optical absorbance measurement to correct for variation in cell yield caused by loss of cell viability or cytotoxicity. The statistically defined threshold for a positive result in the GreenScreen HC assay is 1.5, i.e., 50% induction over and above the baseline for the vehicle-treated control.

Cytotoxicity is measured in the GreenScreen assay alongside genotoxicity and the results of the cytotoxicity assessment are used to normalise the genotoxicity measurements as described above.

In the GreenScreen HC assay, cell viability is assessed using a propidium iodide uptake assay. Propidium iodide is an intercalating agent and a fluorescent molecule that can be used to stain cells. It is commonly used to quantitatively assess DNA content to evaluate cell viability or DNA content in cell cycle analysis and can be used to differentiate necrotic, apoptotic and normal cells (see, e.g., Dengler et al., 1995, Anticancer Drugs, Vol. 6, No. 4, pp. 522-532). Exposure to a cytotoxic compound increases the uptake of propidium iodide, which is monitored by optical absorbance and is proportional to cell proliferation. Cytotoxic compounds are those that show an observed decrease in relative population survival below a significance threshold set at 90% compared to vehicle-treated control, at one or more test concentrations.

A dilution series of each test compound is generated in parallel in a 96-well, black microplate with an optically clear base. A standard genotoxic compound (methyl methanesulfonate, MMS) is added as an intra-plate quality control check. The plates are analysed at 24 hour and 48 hour time points using a microplate reader, which provides measurements of light absorbance and fluorescence for cells and solutions in the microplates wells.

In addition to measurements of cell viability and genotoxicity described above, the GreenScreen assay incorporates an assessment of the effects of metabolic activation in the assay, the "GreenScreen HC S9 assay". To accomplish this, the cells are incubated both in the presence of and absence of the post-mitochondrial supernatant liver extract (known as "S9"). S9 is routinely used in genetic toxicology to supplement the test cells with mammalian phase I metabolism. To assess metabolic activation, compounds are incubated with the TK6 strain in the presence of 1% v/v S9 fraction mix for 3 hours with a subsequent 45 hour recovery time. After the recovery period, the GFP fluorescence signal and cell viability (assessed by propidium iodide uptake) are measured using a flow cytometer. Cyclophosphamide, a commonly used control in genotoxicity studies utilising metabolic activation, is used as the positive control in the assay. In the GreenScreen HC S9 assay, genotoxicity is evaluated by induction in GFP expression quantified using the mean sample fluorescence and cytotoxicity using the propidium iodide uptake assay described above. The statistically defined threshold for a positive genotoxicity result is 1.3, i.e. 30% induction over and above the baseline for the vehicle-treated control and the result is reported as positive or negative. Cytotoxic compounds are those that show an observed decrease in relative population survival below a significance threshold set at 90% compared to vehicle-treated control, at one or more test concentrations.

Stably transfected reporter cell lines were derived from the p53-competent human lymphoblastoid TK6 cell line. The reporter cell line carries an episomally replicating plasmid bearing the upstream promoter region and other regulatory sequences of the human GADD45a gene linked to a human optimised Green Fluorescent Protein (GFP) gene. The control cell line carries an identical plasmid except for the removal of 4 base pairs at the start of the EGFP gene, such that GFP is not produced. Both plasmids also carry a gene conferring resistance to hygromycin B to the cell line, allowing continued selection for plasmid presence (200 µg/mL hygromycin B; Invitrogen Corporation, Carlsbad, Calif.). Both cell lines were maintained in complete culture medium (RPMI 1640 with GlutaMAX™ and 25 mM N-2-hydroxyethylpiperazine-N-2-ethanesulfonic acid (Invitrogen Corporation) supplemented with 10% (v/v) heat-inactivated donor horse serum (Lonza Wokingham Ltd, Wokingham, UK), 10 mM sodium pyruvate (Invitrogen Corporation) and 5000 U/ml penicillin G sodium with 5000 µg/ml streptomycin sulphate (Invitrogen Corporation)) at 37° C. with 5% $CO_2$ in a humidified atmosphere.

Each assay plate is prepared to assess each test compounds across nine serial 2-fold dilutions, with both the reporter strain and a control cell line which contains the same genetic modifications as the test strain, but does not produce GFP because of a minor change to the sequence at the beginning of the inserted GFP gene. Forty-eight hour exposures were performed in sterile black walled, optically clear, flat-bottomed polystyrene 96-well microplates. Duplicate wells of both 'high' (50 µg/mL) and 'low' (10 µg/mL) concentrations of methyl methanesulfonate were included as intra-plate positive controls to provide data acceptance. Other control wells included vehicle-treated (1% v/v DMSO) cells as a negative control, assay medium alone to check for contamination, and test compound with assay medium to determine any inherent fluorescence and/or optical absorbance due to colour or precipitation.

Breathable membranes (BreathEasy, Diversified Biotech, USA) were applied to the microplates prior to their vigorous shaking (20 seconds). This was followed by static incubation for 48 hours at 37° C. and 5% $CO_2$ in a humidified atmosphere. After 48 hours, the microplates were vigorously shaken for 10 seconds to resuspend cells prior to spectrophotometric data acquisition. Fluorescence data were normalized to absorbance data to give a 'brightness' value relative to the average of vehicle-treated controls and plotted against compound concentration. A brightness increase of ≥50% was classified as a positive result for genotoxicity: this reflects an increase of greater than three times the standard deviation in fluorescence data from vehicle-treated and non-genotoxin-treated cells. The absorbance data were normalized to the vehicle-treated control and plotted as cytotoxicity. Cytotoxicity of 90% reflects a statistically significant fall in cell yield and is recorded as a growth inhibitory toxic effect.

Raw data collected from GreenScreen HC assay microplates, using the microplate were automatically analysed using a GreenScreen HC software template to produce a result summary for the following parameters: lowest effective concentrations (LECs) that cause positive results in the propidium iodide exclusion assay (i.e., loss of cell viability) at 24 hours and 48 hours in the presence and absence of S9 fraction; negative or positive effects on genotoxicity.

The results are summarised in the following table.

TABLE 10

Cytotoxicity and Genotoxicity

| Compound | Cytotoxicity, LEC (µM) | | | Genotoxicity |
|---|---|---|---|---|
| | 24 h | 48 h, −S9 | 48 h, +S9 | |
| ABD735 | 0.31 | 0.31 | 5 | Negative |
| ABD836 | 0.04 | 0.01 | 40 | Positive |
| ABD899 [1] | <0.001 | <0.001 | 0.32 | Positive |
| ABD899 [2] | 0.64 | 0.08 | 81.9 | Negative |
| ABD900 | 0.29 | 0.07 | 74.1 | Negative |
| REF001 | 0.039 | 0.039 | 0.63 | Positive |
| HMC-C-01-A | 0.47 | 0.12 | 60 | Negative |
| HMC-C-02-A | >1000 | 60 | 120 | Negative |
| HMC-C-03-A | 0.24 | 0.06 | 15 | Negative |
| HMC-N-01-A | 0.94 | 0.12 | 60 | Negative |
| HMC-N-02-A | 0.94 | 0.47 | 120 | Negative |
| HMC-N-03-A | 0.94 | 0.24 | 30 | Negative |
| HMC-N-04-A | 0.47 | 0.12 | 30 | Negative |
| HMC-C-01-B | 0.08 | 0.005 | 4.82 | Negative |
| HMC-C-03-B | 0.17 | 0.08 | 10.8 | Positive |
| HMC-N-01-B | 0.01 | 0.05 | 5.85 | Negative |
| HMC-N-02-B | 0.04 | 0.01 | 10.2 | Negative |

[1] A lab scale batch was tested in the range 1.3 mM to 0.3 pM.
[2] A mid scale batch was tested in the range 164 µM to 0.003 µM.

These data indicate that the HMC compounds described herein show enhanced or at least similar cytotoxicity and genotoxicity to the reference compounds and are markedly better than ABD836 and REF001 in particular.

The data also demonstrate that the changes required to improve the cytotoxicity or genotoxicity profile is neither trivial nor predictable. This is particularly highlighted by the profiles of the closely related compounds ABD836 and HMC-N-02-A.

Furthermore, the data show the exceptional safety with respect to general cytotoxicity of compounds HMC-C-02-A, HMC-C-01-A, HMC-N-02-A, and HMC-N-01-A.

Biological Study 9 hERG Ion Channel Assay

Inhibition of the human Ether-à-go-go-Related Gene (hERG) ion channel mediates the repolarizing IKr current in the cardiac action potential, thereby indicating that it contributes to the electrical activity that coordinates the beating of the heart. When the ability of hERG to conduct electrical current across the cell membrane is inhibited or compromised it can result in a potentially fatal disorder called long QT syndrome. This association between hERG and long QT syndrome has made hERG inhibition an important anti-target that must be avoided during drug development.

The activity of the compounds against the hERG ion channel was tested. The assay was conducted using the automated path-clamp, Q-patch method using stably transfected Chinese Hamster Ovary cells (hERG-CHO). hERG-CHO cells were cultured in F-12 Kaighn's Nutrient Mixture medium (Invitrogen)+10% FBS at 37° C. for 1-3 days. Cells were kept at 30° C. for 24 to 48 hours prior to patch clamping in order to increase the hERG current amplitude. Subsequently, the cells were harvested by trypsinisation, and kept in Serum Free Medium (SFM) in the Q-patch cell preparation state for up to 6 hours at room temperature before being washed and re-suspended in extracellular solution and applied to the patch clamp sites for data recording.

Patch-clamp voltage protocol: After whole cell configuration was achieved, the cell was held at −80 mV. A 50 millisecond pulse to −40 mV was delivered to measure the leaking current, which was subtracted from the tail current on-line. Then the cell was depolarized to +20 mV for 2 seconds, followed by a one second pulse to −40 mV to reveal hERG tail current. This paradigm was delivered once every 5 seconds to monitor the current amplitude.

Extracellular solution: 137 mM NaCl, 4 mM KCl, 1.8 mM $CaCl_2$, 1 mM $MgCl_2$, 10 mM D(+)-glucose, 10 mM HePES buffer (pH adjusted to 7.4 with NaOH).

After the whole cell configuration was achieved, the extracellular solution (control) was applied first and the cell was stabilized for 2 minutes in extracellular solution. The test compound was then applied from low concentrations to high concentrations cumulatively. The cell was incubated with each test concentration for 5 minutes. During each incubation, the cell was repetitively stimulated using the voltage protocol described above, and the tail current amplitude was continuously monitored.

Acceptance Criteria:
(1) Peak tail current >100 pA in control.
(2) Initial run-down <30% and the run-down stops before first application of the test compound.
(3) Leak currents <50% of the control peak tail currents at any time.
(4) rs<20 M4 throughout the experiment.

The degree of inhibition (%) was obtained by measuring the tail current amplitude, induced by a one second test pulse to −40 mV after a two second pulse to +20 mV, before and after incubation with the test compound. The difference in current was normalized to control and multiplied by 100 in order to obtain the percent inhibition.

Concentration (log) response curves were fitted to a logistic equation (three parameters assuming complete block of the current at very high test compound concentrations) to generate estimates of the 50% inhibitory concentration ($IC_{50}$). The concentration-response relationship of each compound was constructed from the percentage reductions of current amplitude by sequential concentrations.

The results are summarised in the following table.

TABLE 11 hERG Ion Channel Inhibition

| Compound | IC$_{50}$ (μM) [1] | % inhibition @ 30 μM |
|---|---|---|
| ABD599 | 4.9 | 85 |
| ABD735 | — | 62.5 |
| ABD836 | — | 50 |
| ABD899 | 2.9 | 100 [2] |
| ABD899 | | 53 [3] |
| ABD900 | | 51 |
| REF001 | — | 60 |
| HMC-C-01-A | 19.3 | 79 |
| HMC-C-02-A | 25 | 57 |
| HMC-C-03-A | >30 | 45 |
| HMC-C-04-A | | 69 |
| HMC-N-01-A | 183 | 2 |
| HMC-N-02-A | 231 | 31 |
| HMC-N-03-A | >30 | 13 |
| HMC-N-04-A | >30 | 26 |
| HMC-C-01-B | | 74 |
| HMC-C-02-B | | 94 |
| HMC-C-03-B | | 36 |
| HMC-N-01-B | | 27 |
| HMC-N-02-B | | 23 |
| HMC-N-03-B | | 47 |
| HMC-N-04-B | | 60 |

[1] IC50s were calculated using a four parameter logistic equation calculated automatically in Grafit version 6.0.12 (Erithacus Software Ltd., by Dr Robin Leatherbarrow).
[2] A lab-scale batch was tested.
[3] A mid-scale batch was tested.

The data demonstrate that the HMC compounds described herein have cardiac safety properties required for an orally active drug, and have safety advantages as compared to the reference compounds, such as ABD599 and ABD899, with HMC-N-01-A, HMC-N-02-A and HMC-N-03-A showing a particularly positive profile.

Biological Study 10

Human Primary Leucocyte Studies

The human immune system involves a complex set of cells and organs that can be adversely affected by drugs or chemicals. This results in increased susceptibility to infections, tumours, allergic responses, autoimmune reactions or other forms of immune system diseases. The assessment of immunotoxicity is, therefore, an important component of safety evaluation of new pharmaceuticals, and the ideal profile for a potential anti-inflammatory drug that acts via modulating the immune system is one that demonstrates selectively for certain subsets of immune-system cells with no effects on others, thereby avoiding general immune activation or suppression. For example, a drug that reduces the viability or activity of monocytes with no effects on neutrophils would be expected to possess anti-inflammatory properties with application in a number of diseases without compromising the ability of a patient to respond to, and clear, infections.

The ability of a reference compound (ABD735) to influence the viability of human white blood cells was investigated using cells derived from human whole blood. The effects of a reference compound (ABD735) were tested on the following human white blood cell types: neutrophils, monocytes, B-lymphocytes, and T-lymphocytes, comprising both the CD4 positive (T-helper) and CD8-positive (T-cytotoxic) populations. Each of these cell types has a different function in the human immune system.

Neutrophils are also known as granulocytes. They are the most abundant white blood cells in man and form part of the innate immune system. Neutrophils act as the primary response to the acute phase of inflammation caused by bacteria infection.

Monocytes are part of the innate immune system found in the circulation. Peripheral blood monocytes differentiate to form macrophages, which are the precursors of a number of cells involved in modulating the immune response, including dendritic cells. The primary function of monocyte-macrophages is to act as immune effector cells. They are heavily involved in the pathogenesis of several chronic inflammatory conditions including rheumatoid arthritis and multiple sclerosis.

T-lymphocytes are part of the adaptive immune system and play a central role in immunity. There are several subsets of T-lymphocytes, each of which possess a different function in the immune system. T-cytotoxic lymphocytes are also known as CD8+ T-cells due to the presence of a molecule called CD8 on their surface. Their role is to destroy infected cells and tumour cells, but under inflammatory conditions, they can also act to exacerbate disease. T-helper lymphocytes are also known as CD4+ T-cells due to the presence of a molecule called CD4 on their surface. The function of T-helper cells is to assist in maturing B-lymphocytes and to activate cytotoxic T-cells.

B-lymphocytes are part of the adaptive immune system. Their principal functions are to make antibodies and act as antigen-presenting cells, which allow T-lymphocytes to recognise foreign antigens.

The effects of the reference compound (ABD735) on the viability of neutrophils, monocytes, CD4+ and CD8+ T-cells and B-lymphocytes was assessed under both resting and stimulated conditions. Resting conditions were used to assess likely effects on normal cells found in human blood, and stimulated conditions were used to assess the effects of the compound under disease conditions.

Effects on cell viability were assessed using flow cytometry. Flow cytometry is a laser-based, biophysical technology employed in cell counting, cell sorting, and biomarker detection, by suspending cells in a stream of fluid and passing them by an electronic detection apparatus. It allows simultaneous multi-parametric analysis of the physical and chemical characteristics of up to thousands of particles per second. The sorting of cells using flow cytometry requires the use of specific cell markers. To quantify cell numbers, counting beads are used as an internal standard. Counting beads are a calibrated suspension of microbeads which are added to a known volume of sample so the sample volume per bead is known. This allows the absolute determination of cell number in a sample. In addition, for B- and T-lymphocytes, cell proliferation was measured using a dye known as Cell Proliferation Dye (eFluor® 450). eFluor® 450 is an organic dye which can be conjugated to cell-specific markers. It fluoresces when excited by a laser in a manner proportional to the number of cells bound by the conjugate. Its signal therefore provides an indication of the proliferation of specific cell types.

Neutrophil Isolation and Assessment of Impact on Survival:

Neutrophils were isolated from whole blood (collected from healthy donors) by two-step density gradient Histopaque® 1077 and Histopaque® 1119. Polymorphonuclear cells were washed in RPMI media supplemented with antibiotics (penicillin 100 U/mL, streptomycin 100 μg/mL) and resuspended at $2 \times 10^6$ cells/mL in RPMI supplemented with 10% foetal calf serum (FCS) and antibiotics (penicillin 100 U/mL, streptomycin 100 μg/mL). Then 50 μL of the cell suspension was added to a 96 well plate, with or without reference compound (ABD735) (at 30, 10, 3, 1, or 0.3 μM) or control (0.3% DMSO), with or without dexamethasone (1 μM) and incubated at 37° C./5% $CO_2$ for 24 hours.

Following incubation, the cells were fixed and an exact volume of counting beads was added to each tube to calculate the number of live cells.

Monocyte Isolation and Assessment of Impact on Survival:

PBMCs (peripheral blood mononuclear cells) were collected from healthy donors (all male) and isolated by centrifugation on a layer of Ficoll Paque (GE Healthcare, UK). Cells were then resuspended ($3\times10^6$ cells/mL) in RPMI supplemented with 10% FCS and antibiotics (penicillin 100 U/mL, streptomycin 100 μg/mL) and 1 mL of cell suspension was added to a 48-well plate, which was then incubated for 1 hour at 37° C./5% $CO_2$. Subsequently, the supernatant was aspirated to remove non-adherent cells, which was followed by two washing steps to ensure removal of non-adhered cells. Adhered cells (monocytes) were then stimulated with either LPS (10 ng/mL), TNFα (10 ng/mL) or macrophage colony stimulating factor (M-CSF) (10 ng/mL) in the absence (control) or presence of reference compound (ABD735) (at 30, 10, 3, 1, or 0.3 μM) for 48 hours at 37° C./5% $CO_2$. Subsequently, the plates were centrifuged and the monocytes washed in PBS before addition of PBS plus EDTA (10 mM) and incubation at 4° C. for 20 minutes to help detach the cells, which was facilitated by pipetting. The monocytes were added to Falcon tubes and washed by centrifugation with PBS before an exact volume of counting beads was added to each tube to calculate the number of live cells.

B-Lymphocyte Isolation and Assessment of Impact on Survival:

PBMCs (peripheral blood mononuclear cells) were collected from healthy donors (all female) and isolated by centrifugation on a layer of Ficoll Paque (GE Healthcare, UK). The cells were then resuspended in RPMI supplemented with 10% FCS and antibiotics (penicillin 100 U/mL, streptomycin 100 μg/mL). Cell suspension was added to a 96-well plate with or without reference compound (ABD735) (at 30, 10, 3, 1, or 0.3 μM) or control (0.3% DMSO) with or without a combination of *Staphylococcus aureus* Cowan I (SAC) and interleukin-2 (SAC/IL-2) (1:10,000 and 2 ng/mL) and incubated at 37° C./5% $CO_2$ for 48 hours. Following incubation, the cells were stained with anti-human CD19 before an exact volume of counting beads was added to each tube to calculate the number of live cells.

B-Cell Isolation and Assessment of Impact on Proliferation:

PBMCs (peripheral blood mononuclear cells) were collected from healthy donors (all female) and isolated by centrifugation on a layer of Ficoll Paque (GE Healthcare, UK).

The cells were then stained with Cell Proliferation Dye, which measures the proliferation of cells (eFluor® 450) and re-suspended in RPMI supplemented with 10% FCS and antibiotics (penicillin 100 U/mL, streptomycin 100 μg/mL). Cell suspension was added to a 96 well plate with or without reference compound (ABD735) (at 30, 10, 3, 1, or 0.3 μM) or control (0.3% DMSO) with or without a combination of *Staphylococcus aureus* Cowan I (SAC) and interleukin-2 (SAC/IL-2) (1:10,000 and 2 ng/mL) and incubated at 37° C./5% $CO_2$ for 5 days. Following incubation, the cells were stained with anti-human CD19, a marker of B-lymphocytes, before being analysed on a flow cytometer. Cells that were e450 low were deemed to have proliferated.

T-Cell Isolation and Assessment of Impact on Survival:

PBMCs (peripheral blood mononuclear cells) were collected from healthy donors (all female) and isolated by centrifugation on a layer of Ficoll Paque (GE Healthcare, UK). The cells were then resuspended to $2\times10^6$ cells/mL in RPMI supplemented with 10% FCS and antibiotics (penicillin 100 U/mL, streptomycin 100 μg/mL). Cell suspension was added to a 96-well plate with or without reference compound (ABD735) (at 30, 10, 3, 1, or 0.3 μM) or control (0.3% DMSO) with or without phytohaemagglutinin (PHA, 5 μg/mL) and incubated at 37° C./5% $CO_2$ for 48 hours. Following incubation, the cells were stained with anti-human CD8 or CD4 before an exact volume of counting beads was added to each tube to calculate the number of live cells.

T-Cell Isolation and Assessment of Impact on Proliferation:

PBMCs (peripheral blood mononuclear cells) were collected from healthy donors (all female) and isolated by centrifugation on a layer of Ficoll Paque (GE Healthcare, UK).

The cells were then stained with Cell Proliferation Dye (eFluor® 450) and re-suspended in RPMI supplemented with 10% FCS and antibiotics (penicillin 100 U/mL, streptomycin 100 μg/mL). Cell suspension was added to a 96-well plate with or without reference compound (ABD735) (at 30, 10, 3, 1, or 0.3 μM) or control (0.3% DMSO) with or without phytohaemagglutinin (PHA, 5 μg/mL) and incubated at 37° C./5% $CO_2$ for 5 days. Following incubation, the cells were stained with either anti-human CD8 or CD4 before being analysed on a flow cytometer. Cells that were e450 low were deemed to have proliferated.

The average results (n=3) for the reference compound (ABD735) were expressed as a fold change versus the average control value. The data were then plotted graphically using software from Grafit (Erithacus Software). Each experiment was repeated three times and the data are presented as the mean from all experiments.

The results are summarised in the following tables.

TABLE 12

Cell Viability in the presence of ABD735 (3 μM)

| Cell type | Stimulation | Fold change in viability |
|---|---|---|
| Neutrophils | — | 1.0 |
|  | Dexamethasone | 0.8 |
| B-lymphocytes | — | 0.9 |
|  | SAC/IL-2 | 1.1 |
| CD4+ T-lymphocytes | — | 0.9 |
|  | phytohaemagglutinin | 0.6 |
| CD8+ T-lymphocytes | — | 0.8 |
|  | phytohaemagglutinin | 0.7 |
| Monocytes | — | 0.7 |
|  | M-CSF | 1.1 |
|  | LPS | 1.0 |
|  | TNFα | 0.5 |

TABLE 13

Cell Proliferation in the presence of ABD735 (3 μM)

| Cell type | Stimulation | Fold change in proliferation |
|---|---|---|
| B-lymphocytes | — | 0.9 |
|  | SAC/IL-2 | 0.6 |

TABLE 13-continued

Cell Proliferation in the presence of ABD735 (3 μM)

| Cell type | Stimulation | Fold change in proliferation |
|---|---|---|
| CD4+ T-lymphocytes | — | 1 |
|  | phytohaemagglutinin | 0.6 |
| CD8+ T-lymphocytes | — | 0.7 |
|  | phytohaemagglutinin | 0.3 |

The results from a single high concentration (3 μM) of the reference compound (ABD735) across the leucocyte types are shown above. In this assay, a fold-change of 0.5 or lower is significant for loss of viability, and a fold-change of 0.6 or lower is significant for reductions in proliferation.

It can be seen from these data that the reference compound (ABD735) selectively reduces the viability of monocytes in the presence of TNFα only, and not in the presence of either M-CSF or LPS. In addition, the reference compound (ABD735) has very little effect on the viability of the other leucocyte populations indicating that compounds from this series are not generally immunosuppressive. The reference compound (ABD735) is also shown to reduce the proliferation of lymphocytes, with the most profound effects seen in stimulated CD8+T-lymphocytes. A profile such as this, with selective reduction in the proliferation of lymphocyte subpopulations is an attractive mechanistic profile for the treatment of diseases of inflammation such as rheumatoid arthritis, systemic lupus erythematosus, Crohn's disease, and multiple sclerosis, as well as for the treatment of leukaemias including: T-cell lymphoma, such as extranodal T-cell lymphoma, cutaneous T-cell lymphoma, anaplastic large cell lymphoma, and angioimmunoblastic T cell lymphoma; B-cell lymphoma, such as Hodgkin's and non-Hodgkins lymphomas, including diffuse large B-cell lymphoma, follicular lymphoma, mucosa-associated lymphatic tissue lymphoma, small cell lymphocytic lymphoma, mantle cell lymphoma, and Burkitt's lymphoma; and other leukaemias, such as chronic lymphocytic leukaemia and multiple myeloma.

Biological Study 11

Rat Pristane-Induced Arthritis Study

Female Lewis rats were used for all procedures. Animals were housed in groups of 5, and were maintained at 21° C.±2° C. on a 12-hour light/dark cycle with food and water ad libitum. Arthritis was induced by the administration of 0.3 mL pristane intra-dermally at the base of the tail. The rats started to develop signs and symptoms of arthritis approximately seven days after the pristane injection.

For macroscopic assessment of arthritis, the following signs were monitored in each paw of each mouse three times per week and summed to generate the Arthritic Index (AI) (the maximum AI for one animal is 16):
 0=no visible effects of arthritis.
 1=oedema and/or erythema of 1 digit.
 2=oedema and/or erythema of 2 digits.
 3=oedema and/or erythema of more than 2 digits.
 4=severe arthritis of entire paw and digits including limb deformation and ankylosis of the joint.
Animals were sorted into treatment groups prior to pristane administration and dosed once daily for 28 days with test compound at doses of 3 and 10 mg/kg/day by oral gavage, or by intraperitoneal injection at a dose of 0.05 mg/kg for the positive control, methotrexate. After completion of the experiment, the rats were sacrificed.

The data were analysed by generating an average of the arthritic index across each treatment group. The mean arthritic index was then compared to the arthritic index of control (untreated) animals using the following formula to generate a percentage inhibition of disease.

$$\% \text{ inhibition of disease} = 100 - \left[\frac{\text{average arthritic index: treated animals}}{\text{average arthritic index: untreated animals}} * 100\right]$$

The data summarised in the following table.

TABLE 14

Inhibition of Arthritis

| Compound | Dose (mg/kg/day) | % inhibition of disease |
|---|---|---|
| ABD899 | 3 | 21 |
| ABD899 | 10 | ND[(1)] |
| HMC-C-01-A | 3 | 40 |
| HMC-C-01-A | 10 | 67 |
| HMC-N-01-A | 3 | 39 |
| HMC-N-01-A | 10 | 60 |

[(1)]Dosing was terminated on day 10 due to adverse effects.

Figure 3:
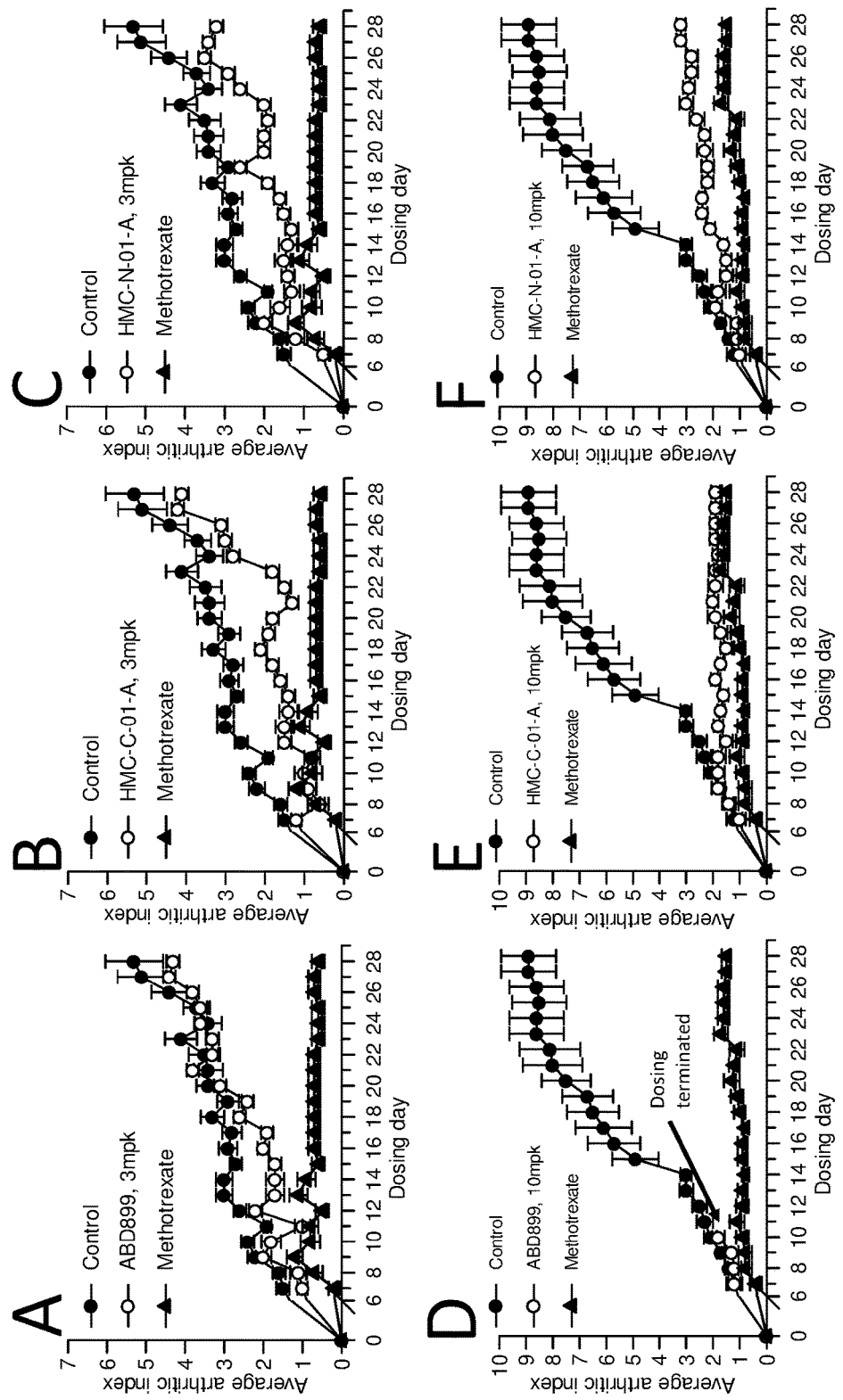
FIG. 3 shows six graphs, each of average arthritic index as a function of time (dosing day) for test compound (open circles), control (solid circles), and positive control, methotrexate (triangles) for each of: (A) ABD899 dosed at 3 mg/kg/day (top left), (B) HMC-C-01-A dosed at 3 mg/kg/day (top middle), (C) HMC-N-01-A dosed at 3 mg/kg/day (top right), (D) ABD899 dosed at 10 mg/kg/day (bottom left), (E) HMC-C-01-A dosed at 10 mg/kg/day (bottom middle), and (F) HMC-N-01-A dosed at 10 mg/kg/day (bottom right), as described in Biological Study 11 below.

The data for several of the compounds are also illustrated in FIG. 3.

FIG. 3 shows six graphs, each of average arthritic index as a function of time (dosing day) for test compound (open circles), control (solid circles), and positive control, methotrexate (triangles) for each of: (A) ABD899 dosed at 3 mg/kg/day (top left), (B) HMC-C-01-A dosed at 3 mg/kg/day (top middle), (C) HMC-N-01-A dosed at 3 mg/kg/day (top right), (D) ABD899 dosed at 10 mg/kg/day (bottom left), (E) HMC-C-01-A dosed at 10 mg/kg/day (bottom middle), and (F) HMC-N-01-A dosed at 10 mg/kg/day (bottom right).

These data indicate that the HMC compounds described herein show excellent oral in vivo activity in preventing the progression of pristane induced arthritis, whilst compound ABD899 had limited effect on disease in this model, in spite of good activity in Biological Study 6. In addition, compounds HMC-C-01-A and HMC-N-01-A were tolerated well by the animals during extended dosing, whilst ABD899 was poorly tolerated such that it was necessary to terminate dosing and remove the animals receiving it from the study (shown in FIG. 3, panel D). Furthermore, compound HMC-C-01-A showed particularly good efficacy in the model, which was equivalent to that of the marketed first-line therapy for rheumatoid arthritis, methotrexate.

The data further show that the identification of compounds with superior efficacy is neither trivial nor predictable.

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these publications are provided below. Each of these publications is incorporated herein by reference in its entirety into the present disclosure, to the same extent as if each individual publication was specifically and individually indicated to be incorporated by reference.

Akahoshi et al., 2008, "Promoter polymorphisms in the IRF3 gene confer protection against systemic lupus erythematosus", *Lupus*, Vol. 17 pp. 568-574.

Astry et al., 2011, "A cytokine-centric view of the pathogenesis and treatment of autoimmune arthritis", *J Interferon Cytokine Res.*, Vol. 31, pp. 927-940.

Bahmanyar et al., 2010, "Aminotriazolopyridines and their use as kinase inhibitors", international patent publication number WO 2010/027500 A1 published 11 Mar. 2010.

Baud et al., 1999, "Signalling by proinflammatory cytokines: oligomerization of TRAF2 and TRAF6 is sufficient for JNK and IKK activation and target gene induction via an amino-terminal effector domain", *Genes Dev.*, Vol. 13, pp. 1297-1308.

Baud et al., 2009, "Is NFκB a good target for cancer therapy? Hopes and pitfalls", *Nat. Rev. Drug Disc.*, Vol. 8, pp. 33-40.

Billiau, 2010, "Etanercept improves linear growth and bone mass acquisition in MTX-resistant polyarticular-course juvenile idiopathic arthritis", *Rheumatology (Oxford)*, Vol. 49, pp. 1550-1558.

Bladh et al., 2006, "Novel sulphonamide derivatives as glucocorticoid receptor modulators for the treatment of inflammatory diseases", international patent publication number WO 2006/046916 A1 published 4 May 2006.

Brennan et al., 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Brennan et al., 1996, "Cytokines in autoimmunity", *Curr. Opin. Immunol.*, Vol. 8, pp. 872-877.

Chen et al., 2012, "High-affinity and selective dopamine $D_3$ receptor full agonists", *Bioorg. & Med. Chem. Lett.*, Vol. 22, pp. 5612-5617.

Childs, L. M., et al., 2001, "Efficacy of etanercept for wear debris-induced osteolysis", *Journal of Bone and Mineral Research*, Vol. 16, No. 2, pp. 338-347.

Dallas et al., 2011, "Osteoimmunology at the *nexus* of arthritis, osteoporosis, cancer, and infection", *J. Clin. Invest.*, Vol. 121, pp. 2534-2542.

Dimitris et al., 1998, "The Pathophysiologic Roles of Interleukin-6 in Human Disease", *Ann Intern Med.*, Vol. 128, No. 2, pp. 127-137.

Dvorak et al., 1996, "Comparative ultrastructural morphology of human basophils stimulated to release histamine by anti-IgE, recombinant IgE-dependent histamine-releasing factor, or monocyte chemotactic protein-1", *Journal of Allergy and Clinical Immunology*, Vol. 98, pp. 355-370.

Feldmann et al., 1994, "TNF alpha as a therapeutic target in rheumatoid arthritis," *Circ. Shock*, Vol. 43, pp. 179-184.

Feldmann et al., 1996, "Rheumatoid arthritis", *Cell*, Vol. 85, pp. 307-310.

Feldmann et al., 2001, "The role of TNF alpha and IL-1 in rheumatoid arthritis," *Curr. Dir. Autoimmun.*, Vol. 3, pp. 188-199.

Firestein, 2005 "Immunologic mechanisms in the pathogenesis of rheumatoid arthritis", *J. Clin. Rheumatol.*, Vol. 11. pp. S39-S44.

Fu et al., 2011, "Association of a functional IRF7 variant with systemic lupus erythematosus", *Arthritis Rheum.*, Vol. 63, pp. 749-754.

Gabay, 2006, "Interleukin-6 and chronic inflammation", *Arthritis Research & Therapy*, Vol. 8 (Suppl 2), S3.

Galli et al., 1989, "IgE, Mast Cells and the Allergic Response", *Ciba Foundation Symposium*, Vol. 147, pp. 53-73.

Gottlieb, 2005, "Psoriasis: Emerging Therapeutic Strategies", *Nat. Rev. Drug Disc.*, Vol. 4, pp. 19-34.

Greig et al., 2006, "Development and characterization of biphenylsulfonamides as novel inhibitors of bone resorption", *J. Med. Chem.*, Vol 49: pp 7487-7492.

Greig et al., 2008, "Biphenyl-4-yl-sulfonic acid arylamides and their use as therapeutic agents", international patent publication number WO 2008/114022 A1 published September 2008.

Greig et al., 2010a, "Aryl-phenyl-sulfonamido-cycloalkyl compounds and their use", international patent publication number WO 2010/032009 A1 published March 2010.

Greig et al., 2010b, "Aryl-phenyl-sulfonamido-phenylene compounds and their use", international patent publication number WO 2010/032010 A1 published March 2010.

Greig et al., 2013, "Development of triarylsulfonamides as novel anti-inflammatory agents", *Bioorq. & Med. Chem. Lett.*, Vol. 23, pp. 816-820.

Hadida et al., 2007, "Heterocyclic modulators of ATP-binding cassette transporters", international patent publication number WO 2007/056341 A1 published 18 May 2007.

Hu et al., 2011, "A meta-analysis of the association of IRF5 polymorphism with systemic lupus erythematosus International", *Journal of Immunogenetics*, Vol. 38, pp. 411-417.

Jimi et al., 2004, "Selective inhibition of NF-kappa B blocks osteoclastogenesis and prevents inflammatory bone destruction in vivo", *Nat. Med.*, Vol. 10, pp. 617-624.

Joosten et al., 1996, "Anticytokine treatment of established type II collagen-induced arthritis in DBA/1 mice. A comparative study using anti-TNF alpha, anti-IL-1 alpha/beta, and IL-1Ra," *Arthritis Rheum.*, Vol. 39, pp. 797-809.

Karsenty et al., 2002, "Reaching a genetic and molecular understanding of skeletal development", *Dev. Cell.*, Vol. 2, pp. 389-406.

Klareskog et al., 2006, "Mechanisms of disease: Genetic susceptibility and environmental triggers in the development of rheumatoid arthritis," *Nat. Clin. Pract. Rheumatol.*, Vol. 2, pp. 425-433.

Korzenik et al., 2006, "Evolving knowledge and therapy of inflammatory bowel disease," *Nat. Rev. Drug Disc.*, Vol. 5, pp. 197-209.

Krausgruber et al., 2011, "IRF5 promotes inflammatory macrophage polarization and TH1-TH17 responses", *Nat. Immunol.*, Vol. 12, pp. 231-238.

Li et al., 2008, "A tumor necrosis factor-α-mediated pathway promoting autosomal dominant polycystic kidney disease", *Nature Medicine*, Vol. 14, No. 8, pp. 863-868.

Liu, 2005, "Molecular mechanism of TNF signalling and beyond," *Cell Res.*, Vol. 15, pp. 24-27.

Long, 2012, "Osteoimmunology: the expanding role of immunoreceptors in osteoclasts and bone remodeling", *Bone Key Rep.*, Vol. 1, p. 59.

Malemud et al., 2010, "Myeloid-related protein activity in Rheumatoid Arthritis", *International Journal of Interferon, Cytokine and Mediator Research*, Vol. 2, pp. 97-111.

Mantovani, 2009, "Inflaming metastasis", *Nature*, Vol. 457, pp. 36-37.

Mazzucchelli et al., 1996, "Differential in situ expression of the genes encoding the chemokines MCP-1 and RANTES in human inflammatory bowel disease", *J. Pathol.*, Vol. 178, No. 2, pp. 201-206.

McInnes et al., 2007, "Cytokines in the pathogenesis of rheumatoid arthritis", *Nat. Rev. Immunol.*, Vol. 7, pp. 429-442.

Minamino et al., 2012, "IRF-2 regulates B-cell proliferation and antibody production through distinct mechanisms", *Int Immunol.*, Vol. 24, pp. 573-581.

Mount et al., 2005, "Rheumatoid arthritis market", *Nat. Rev. Drug Disc.*, Vol. 2, pp. 11-12.

O'Shea et al., 2013, "Janus kinase inhibitors in autoimmune diseases", *Annals of Rheumatic Disease*, Vol. 72, Supplement 2, pp. 111-115.

Ogata et al., 2012, "Safety and Efficacy of Tocilizumab for the Treatment of Rheumatoid Arthritis", *Clin Med Insights Arthritis Musculoskelet Disord.*, Vol. 5, pp. 27-42.

Parameswaran et al., 2010, "Tumor necrosis factor-α signaling in macrophages", *Crit. Rev. Eukaryot. Gene Expr.*, Vol. 20, pp. 87-103.

Philchenkov et al., 2004, "Caspases and cancer: mechanisms of inactivation and new treatment modalities", *Exp. Oncol.*, Vol 26, pp 82-97.

Pisetsky, 2012, "Advances in the treatment of inflammatory arthritis", *Best Pract. Res. Clin. Rheumatol.*, Vol. 26. pp. 251-261.

Ralston et al., 2005, "Aryl alkyl sulfonamides as therapeutic agents for the treatment of bone conditions", international patent publication number WO 2005/118528 A2 published 15 Dec. 2005.

Rincon, 2012 "Interleukin-6: from an inflammatory marker to a target for inflammatory diseases", *Trends in Immunology*, Vol. 33, No. 11, pp. 571-577.

Roodman, 2006, "Regulation of osteoclast differentiation", *Ann. N. Y. Acad. Sci.*, Vol. 1068, pp. 100-109.

Scott et al., 2010, "Rheumatoid Arthritis", *Lancet*, Vol. 376, pp. 1094-1108.

Sharif et al., 2012, "IRF5 polymorphism predicts prognosis in patients with systemic sclerosis", *Annals of the Rheumatic Diseases*, Vol. 71, pp. 1197-1202.

Smolen et al., 2003, "Therapeutic Strategies for Rheumatoid Arthritis", *Nat. Rev. Drug Disc.*, Vol. 2, pp. 473-488.

Steger et al., 2011, "Denosumab for the treatment of bone metastases in breast cancer: evidence and opinion", *Ther. Adv. Med. Oncol.*, Vol. 3, pp. 233-243.

Sugiyama et al., 1995, "Chemokines in bronchoalveolar lavage fluid in summer-type hypersensitivity pneumonitis", *Eur. Respir. J.*, Vol. 8, pp. 1084-1090.

Sun, 2010, "Mechanical loading, cartilage degradation and arthritis", *Annals of the New York Academy of Sciences*, Vol. 1211, pp. 37-50.

Takaoka et al., 2005, "Integral role of IRF-5 in the gene induction programme activated by Toll-like receptors", *Nature*, Vol. 434, pp. 243-249.

Takayanagi, 2009, "Osteoimmunology and the effects of the immune system on bone", *Nature Reviews Rheumatology*, Vol. 5, pp. 667-676.

Tanaka et al., 2003, "Signal transduction pathways regulating osteoclast differentiation and function", *J. Bone Miner. Metab.*, Vol. 21, pp. 123-133.

Tsutsumi et al., 2005, "Dipeptidyl peptidase IV inhibitor", international patent publication number WO 2005/025554 A2 published 24 Mar. 2005.

van den Berg et al., 1999, "Pathogenesis of joint damage in rheumatoid arthritis: evidence of a dominant role for interleukin-I", *Baillieres Best Pract. Res. Clin. Rheumatol.*, Vol. 13, pp. 577-597.

van den Berg, 2002, "Is there a rationale for combined TNF and IL-1 blocking in arthritis?", *Clin. Exp. Rheumatol.*, Vol. 20, pp. S21-S25.

Volejnikova et al., 1997, "Monocyte recruitment and expression of monocyte chemoattractant protein-1 are developmentally regulated in remodeling bone in the mouse", *Am. J. Pathol.*, Vol. 150, No. 5, pp. 1711-1721.

Wang et al., 2010, "Selective ligands for the dopamine 3 ($D_3$) receptor and methods of using same", international patent publication number WO 2010/025235 A1 published 4 Mar. 2010.

Zhang et al., 2012 "Regulation of T helper cell differentiation by interferon regulatory factor family members", *Immunol. Res.*, Vol. 54 pp. 169-176.

Zheng et al., 1998, "Gene expression of monocyte chemoattractant protein-1 in giant cell tumors of bone osteoclastoma: Possible involvement in CD68[+] macrophage-like cell migration", *Journal of Cellular Biochemistry*, Vol. 70, No. 1, pp. 121-129.

The invention claimed is:

1. A method of treatment of rheumatoid arthritis comprising administering to a patient in need of treatment a therapeutically effective amount of a compound selected from compounds of the following formulae, or a pharmaceutically acceptable salt thereof:

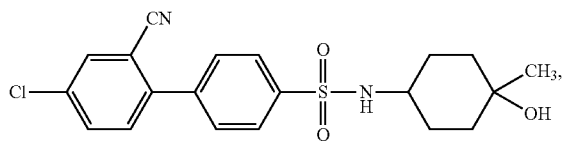

(HMC-C-01)

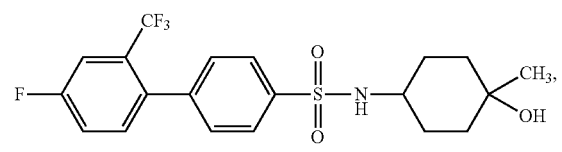

(HMC-C-02)

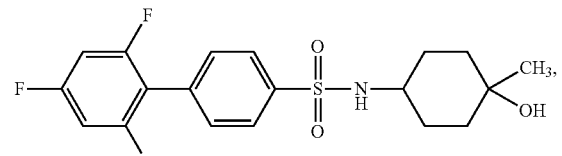

(HMC-C-03)

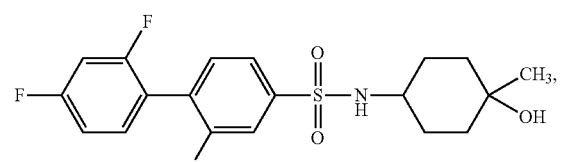

(HMC-C-04)

-continued (HMC-C-05)
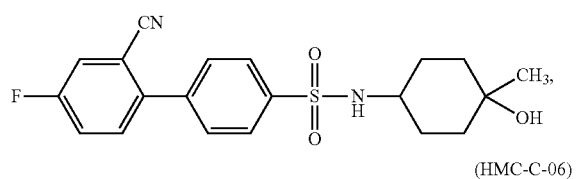

(HMC-C-06)
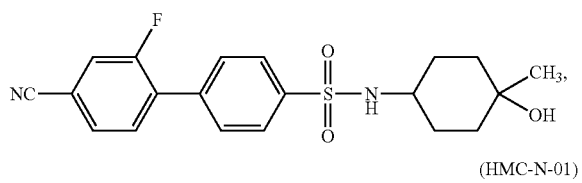

(HMC-N-01)
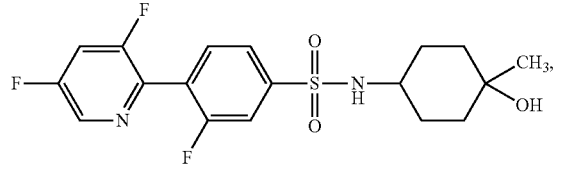

(HMC-N-02)
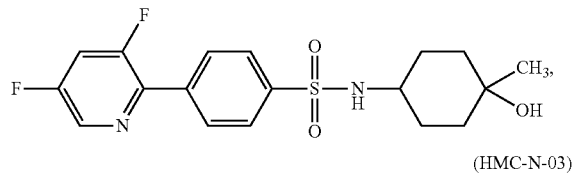

(HMC-N-03)
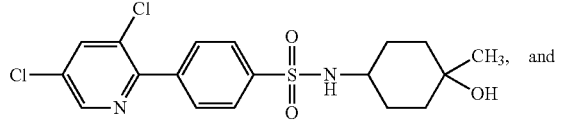

and (HMC-N-04)
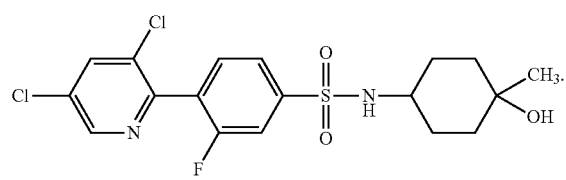

2. A method according to claim 1, wherein the compound is a compound of the following formula, or a pharmaceutically acceptable salt thereof:

(HMC-C-01)
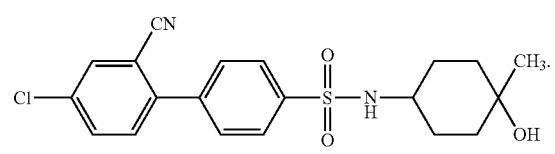

3. A method according to claim 1, wherein the compound is a compound of the following formula, or a pharmaceutically acceptable salt thereof:

(HMC-C-02)

4. A method according to claim 1, wherein the compound is a compound of the following formula, or a pharmaceutically acceptable salt thereof:

(HMC-C-03)

5. A method according to claim 1, wherein the compound is a compound of the following formula, or a pharmaceutically acceptable salt thereof:

(HMC-C-04)

6. A method according to claim 1, wherein the compound is a compound of the following formula, or a pharmaceutically acceptable salt thereof:

(HMC-C-05)

7. A method according to claim 1, wherein the compound is a compound of the following formula, or a pharmaceutically acceptable salt thereof:

(HMC-C-06)
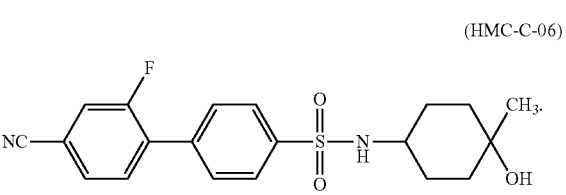 [SMILES: CC1(O)CCC(NS(=O)(=O)c2ccc(-c3ccc(C#N)cc3F)cc2)CC1]

8. A method according to claim 1, wherein the compound is a compound of the following formula, or a pharmaceutically acceptable salt thereof:

(HMC-N-01)

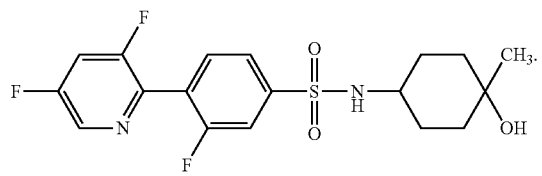

(HMC-C-02-A)

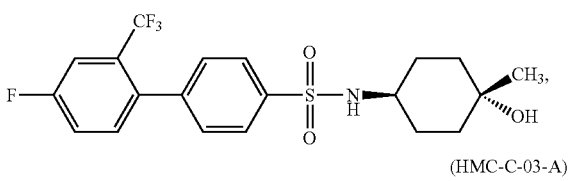

9. A method according to claim 1, wherein the compound is a compound of the following formula, or a pharmaceutically acceptable salt thereof:

(HMC-N-02)

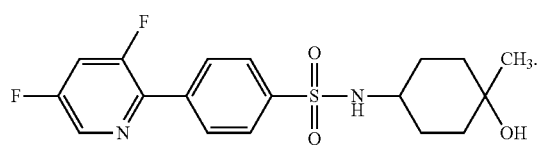

(HMC-C-03-A)

(HMC-C-04-A)

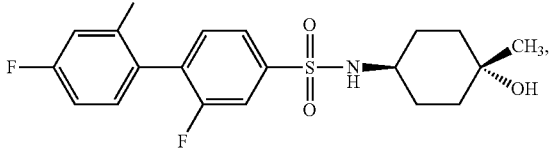

10. A method according to claim 1, wherein the compound is a compound of the following formula, or a pharmaceutically acceptable salt thereof:

(HMC-N-03)

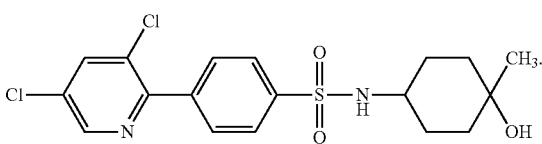

(HMC-C-05-A)

(HMC-C-06-A)

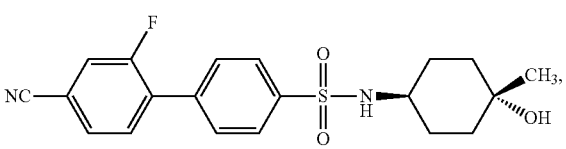

11. A method according to claim 1, wherein the compound is a compound of the following formula, or a pharmaceutically acceptable salt thereof:

(HMC-N-04)

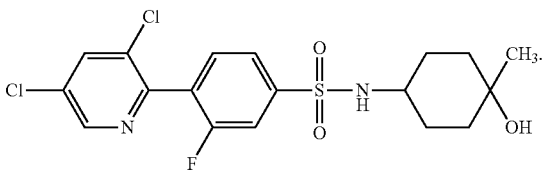

(HMC-N-01-A)

(HMC-N-02-A)

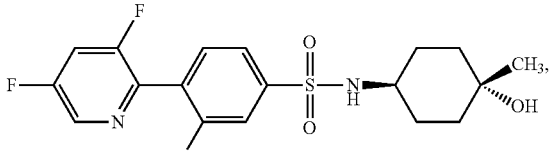

12. A method of treatment of rheumatoid arthritis comprising administering to a patient in need of treatment a therapeutically effective amount of a compound selected from compounds of the following formulae, or a pharmaceutically acceptable salt thereof:

(HMC-C-01-A)

(HMC-N-03-A)

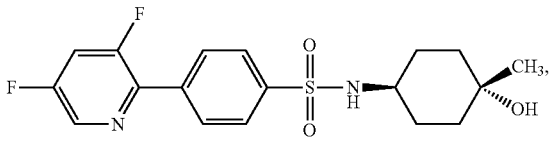

-continued (HMC-N-04-A)
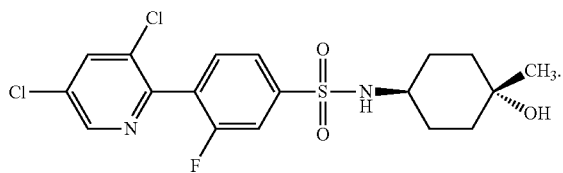

13. A method according to claim 12, wherein the compound is a compound of the following formula, or a pharmaceutically acceptable salt thereof:

(HMC-C-01-A)
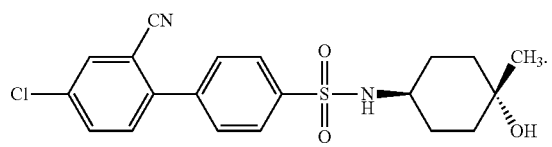

14. A method according to claim 12, wherein the compound is a compound of the following formula, or a pharmaceutically acceptable salt thereof:

(HMC-C-02-A)
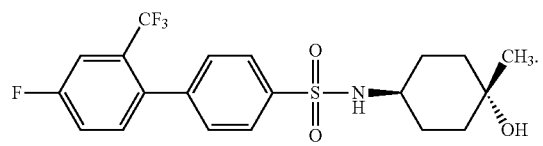

15. A method according to claim 12, wherein the compound is a compound of the following formula, or a pharmaceutically acceptable salt thereof:

(HMC-C-03-A)
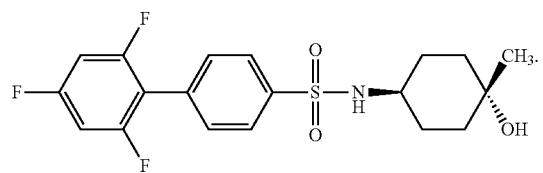

16. A method according to claim 12, wherein the compound is a compound of the following formula, or a pharmaceutically acceptable salt thereof:

(HMC-C-04-A)
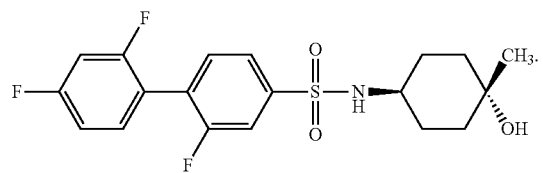

17. A method according to claim 12, wherein the compound is a compound of the following formula, or a pharmaceutically acceptable salt thereof:

(HMC-C-05-A)
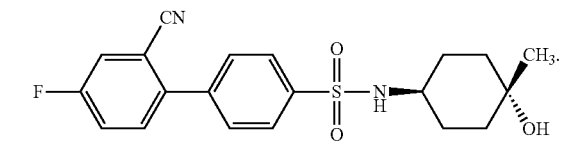

18. A method according to claim 12, wherein the compound is a compound of the following formula, or a pharmaceutically acceptable salt thereof:

(HMC-C-06-A)
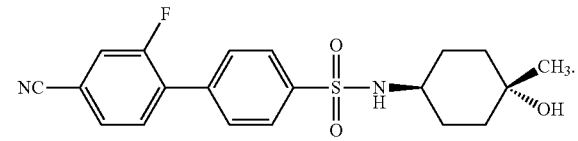

19. A method according to claim 12, wherein the compound is a compound of the following formula, or a pharmaceutically acceptable salt thereof:

(HMC-N-01-A)
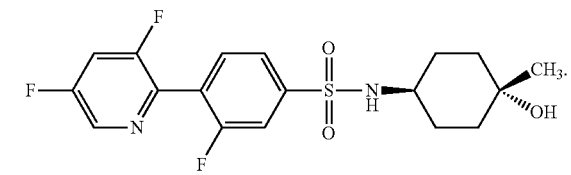

20. A method according to claim 12, wherein the compound is a compound of the following formula, or a pharmaceutically acceptable salt thereof:

(HMC-N-02-A)
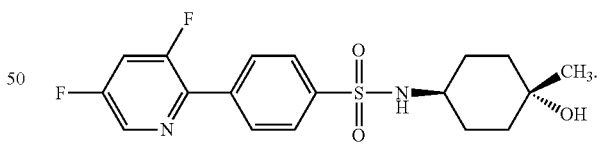

21. A method according to claim 12, wherein the compound is a compound of the following formula, or a pharmaceutically acceptable salt thereof:

(HMC-N-03-A)
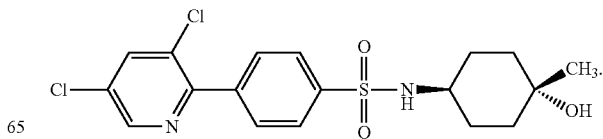

22. A method according to claim 12, wherein the compound is a compound of the following formula, or a pharmaceutically acceptable salt thereof:

(HMC-N-04-A)

23. A method of treatment of rheumatoid arthritis comprising administering to a patient in need of treatment a therapeutically effective amount of a compound selected from compounds of the following formulae, or a pharmaceutically acceptable salt thereof:

(HMC-C-01-B)

(HMC-C-02-B)

(HMC-C-03-B)

(HMC-C-04-B)

(HMC-C-05-B)

(HMC-C-06-B)

(HMC-N-01-B)

(HMC-N-02-B)

(HMC-N-03-B)

and (HMC-N-04-B)

24. A method according to claim 23, wherein the compound is a compound of the following formula, or a pharmaceutically acceptable salt thereof:

(HMC-C-01-B)

25. A method according to claim 23, wherein the compound is a compound of the following formula, or a pharmaceutically acceptable salt thereof:

(HMC-C-02-B)

26. A method according to claim 23, wherein the compound is a compound of the following formula, or a pharmaceutically acceptable salt thereof:

(HMC-C-03-B)

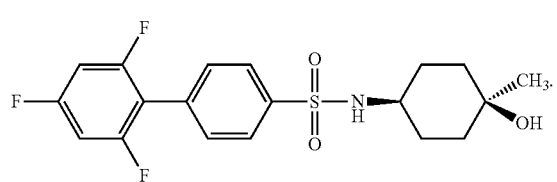

27. A method according to claim 23, wherein the compound is a compound of the following formula, or a pharmaceutically acceptable salt thereof:

(HMC-C-04-B)

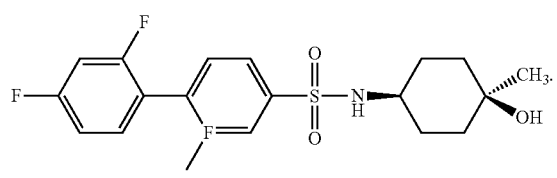

28. A method according to claim 23, wherein the compound is a compound of the following formula, or a pharmaceutically acceptable salt thereof:

(HMC-C-05-B)

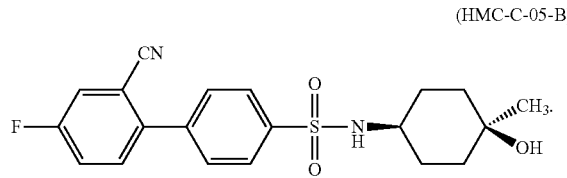

29. A method according to claim 23, wherein the compound is a compound of the following formula, or a pharmaceutically acceptable salt thereof:

(HMC-C-06-B)

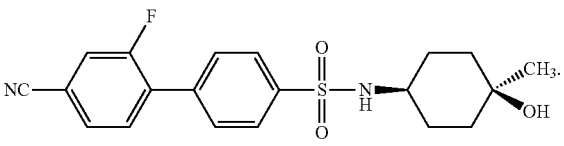

30. A method according to claim 23, wherein the compound is a compound of the following formula, or a pharmaceutically acceptable salt thereof:

(HMC-N-01-B)

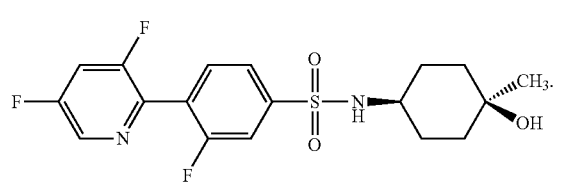

31. A method according to claim 23, wherein the compound is a compound of the following formula, or a pharmaceutically acceptable salt thereof:

(HMC-N-02-B)

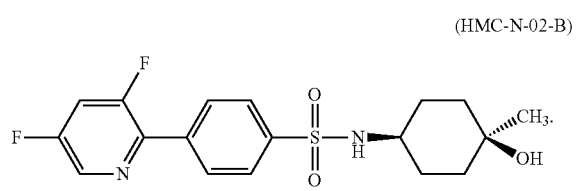 [SMILES: C[C@]1(O)CC[C@@H](NS(=O)(=O)c2ccc(-c3ccc(F)cc3C#N)cc2)CC1]

32. A method according to claim 23, wherein the compound is a compound of the following formula, or a pharmaceutically acceptable salt thereof:

(HMC-N-03-B)

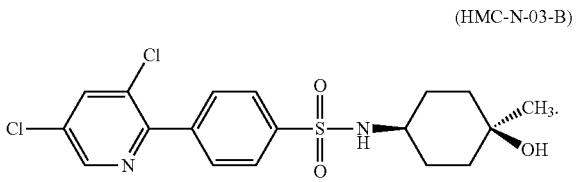 [SMILES: C[C@]1(O)CC[C@@H](NS(=O)(=O)c2ccc(-c3ncc(Cl)cc3Cl)cc2)CC1]

33. A method according to claim 23, wherein the compound is a compound of the following formula, or a pharmaceutically acceptable salt thereof:

(HMC-N-04-B)

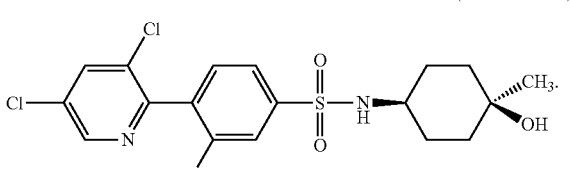

\* \* \* \* \*